United States Patent [19]
Durzan

[11] Patent Number: 5,840,567
[45] Date of Patent: Nov. 24, 1998

[54] SIMPLIFIED HYBRID SEED PRODUCTION BY LATENT DIPLOID PARTHENOGENESIS AND PARTHENOTE CLEAVAGE

[75] Inventor: Don J. Durzan, Davis, Calif.

[73] Assignee: The Regents of the University of California, Oakland, Calif.

[21] Appl. No.: 362,188

[22] Filed: Dec. 21, 1994

[51] Int. Cl.⁶ .................. A01H 4/00; C12H 5/04
[52] U.S. Cl. .................. 435/240.49; 435/240.45; 435/240.5; 435/172.1; 47/58; 800/200; 800/DIG. 49
[58] Field of Search ............... 435/172.1, 172.3, 435/240.4, 240.45, 240.49, 240.5; 800/200, DIG. 49; 47/58

[56] References Cited

PUBLICATIONS

Pramod K. Gupta, et al., "Forestry in the 21st Century", Bio/Technology, vol. 11, 454–459, Apr. 11, 1993.
Don J. Durzan, et al., "Latent Diploid Parthenogenesis and Parthenote Cleavage in Egg-equivalents of Norway Spruce", Int. J. Plant Sci., 155(6):677–688, 1994.
Durzan and Ggupta "Somatic embryogenesis and polyembryogenesis in Douglas–fir cell suspension cultures" Plant Science, 52 pp. 229–235, 1987.

Primary Examiner—Gary Benzion
Attorney, Agent, or Firm—Hana Verny

[57] ABSTRACT

A method for simplified hybrid seed production by latent diploid parthenogenesis and parthenote cleavage. Latent diploid parthenogenesis and subsequent parthenote cleavage is induced by controlled artificial conditions that activate latent apomictic behavior and result in a transition from sexual seed production to diploid asexual parthenogenesis. The method is useful for production of apomictic hybrid seeds.

37 Claims, 23 Drawing Sheets

FIG. 5
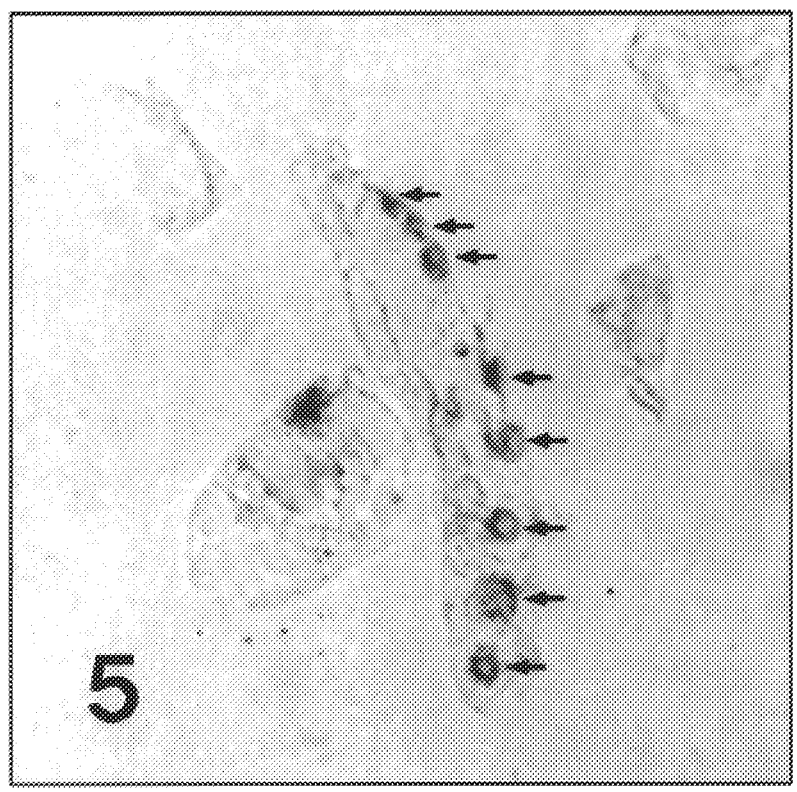
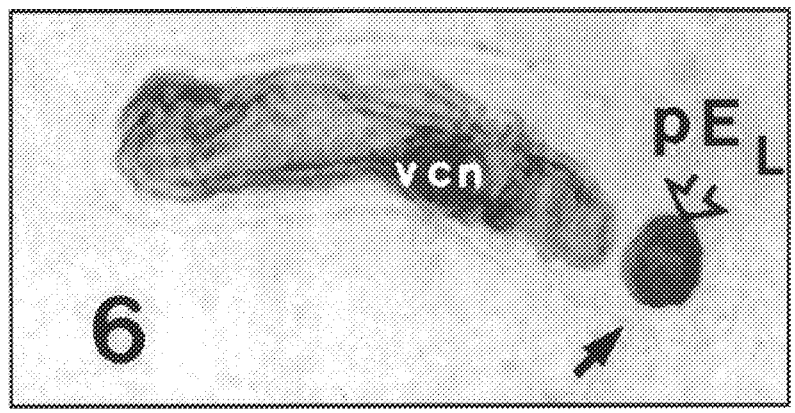
FIG. 6

Recovery Rate

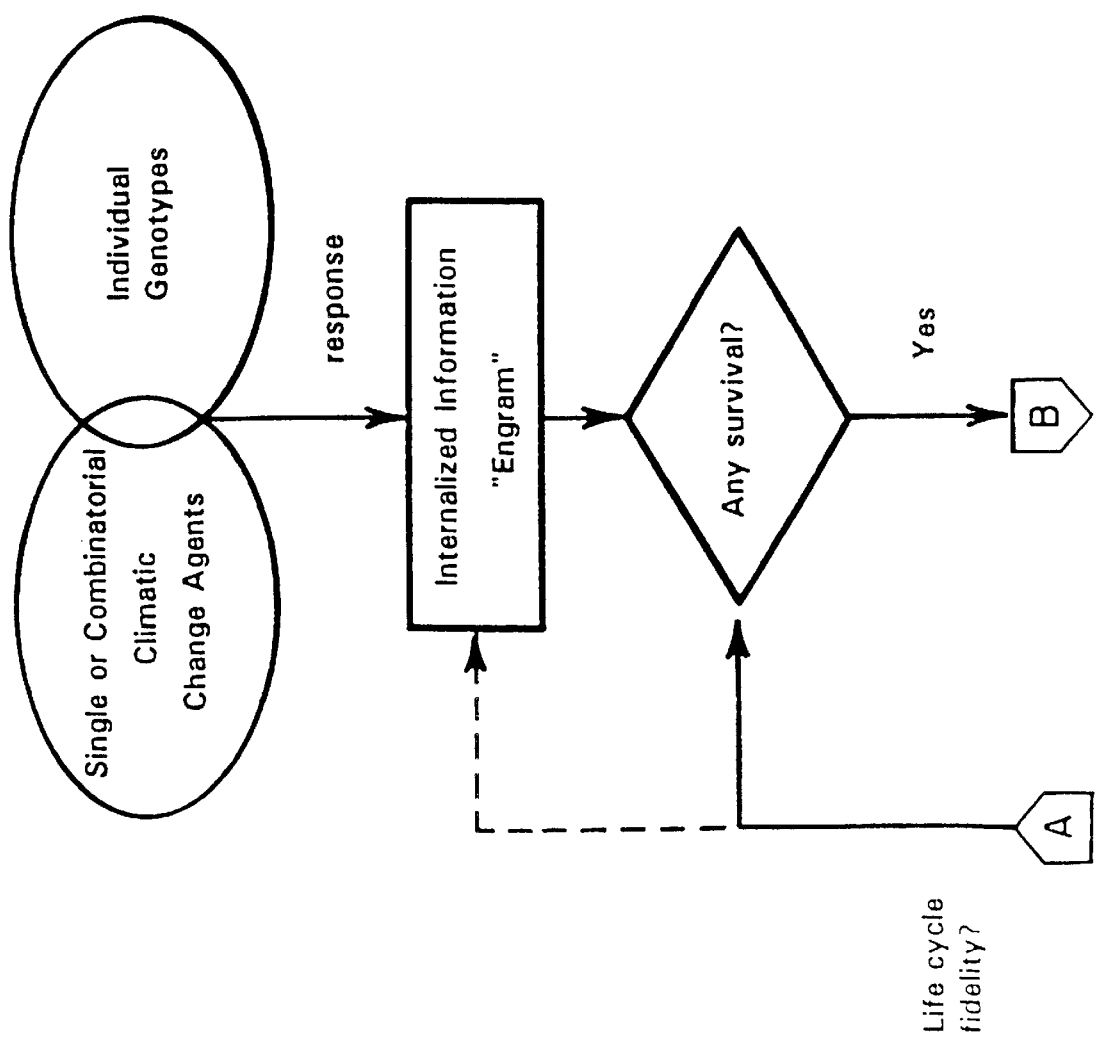
FIG. 21-A

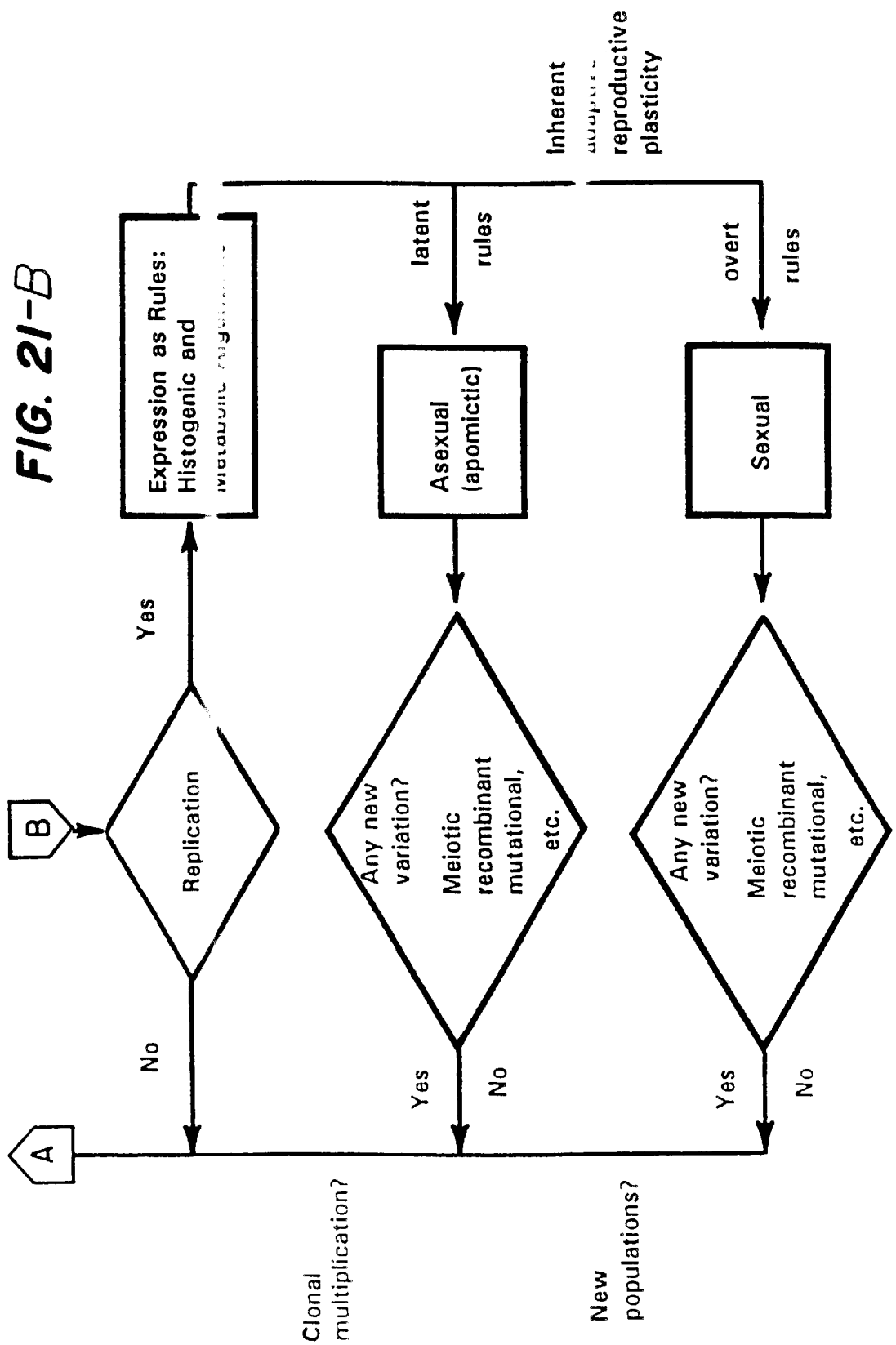
FIG. 21-B

SIMPLIFIED HYBRID SEED PRODUCTION BY LATENT DIPLOID PARTHENOGENESIS AND PARTHENOTE CLEAVAGE

BACKGROUND OF THE INVENTION

Field of Invention

The current invention concerns simplified hybrid seed production by latent diploid parthenogenesis and parthenote cleavage. In particular, this invention concerns a method for latent diploid parthenogenesis and subsequent parthenote cleavage induced by controlled conditions that activate latent apomictic behavior and result in a transition from sexual seed production to diploid nonsexual parthenogenesis. The method is useful for production of apomictic hybrid seeds.

BACKGROUND ART AND RELATED ART DISCLOSURES

In recent years, the demand for wood increased to a point that the demand far exceeds the regenerative ability of the forest and consequently, constant wood harvesting leads to the forest devastation. Additionally, the diversity and extent of the world's forests are declining. Since the demand for wood worldwide is expected to continue, to accommodate this demand, the forest productivity of remaining lands will have to be increased.

Somatic embryogenesis, automated micropropagation systems, and other method for simple and rapid reproduction have the potential for rapidly multiplying high-value genotypes for reforestation which could help to increase forest productivity.

Diploid parthenogenesis represents an asexual escape from sterility through meiosis that is guided in one or several steps by natural selection (*Evolution of Genetic Systems,* 157–168, Oliver, Boyd, Edinburgh, 1958). Such diploid parthenogenesis is generally considered to be absent in gymnosperms (*The Evolution of Asexual Reproduction in Plants,* at 276, Chapman Hall, London, 1992). The diploid parthenogenetic state would make it possible for progeny to forego fertilization without exposing too many undesirable recessive combinations that often occur through introgression. However, such diploid parthenogenesis in gymnosperms has not been successfully achieved.

It would, therefore, be advantageous to provide a method for induction of diploid parthenogenic state in gymnosperms in order to provide asexual reproduction of hybrid seeds and in this way to eliminate or avoid recessive combinations that often occur during sexual hybrid seed production.

Monozygotic cleavage polyembryony, i.e, the subdivision of a single embryo into a group of competing embryos, appears to have little genetic significance in selection, since all embryos are believed to have the same genotype (*Mutations, Developmental Selection, and Plant Evolution,* at 373, Columbia Univ. Press, New York, 1988). In contrast to this view, at the beginning of the century it was postulated that genetic selection among embryos could occur through activities of the suspensors, thereby accounting for fact that usually only one embryo develops to maturity in the ripe seed. In the seed, differences in nutritive tissue and spatial relationships in the corrosion cavity may also contribute to preterminal embryo selection as described in *Am. J. Botany,* 49:327, 1962.

A genetic propensity for polyembryony is one of several conditions leading to the expression of nonrecurrent parthenogenesis. Polyembryony is considered to be a recessive hereditary trait controlled by multiple genes, or by one or more recessive genes, which come together in suitable recombinations after hybridization (*Polyembryony,* 445 in Embryology of Angiosperms, Springer-Verlag, New York, 1984). Cleavage polyembryony would greatly increase the probability that an ovule has at least one surviving embryo. However, until now, such cleavage polyembryony was not described or achieved.

Activation of the latent apomictic behavior requires four conditions that must be met before a transition from sexual reproduction to diploid parthenogenesis can be achieved in cosexual heterosporous plants (*The Evolution of Asexual Reproduction in Plants,* 1992, supra). First, the capacity for parthenogenesis must be present. According to *Int. J. Plant Sci.,* 153:5123 (1992), the apomictic cycle involves a Mendelian gene. Second, this capacity must be expressed by preventing the fertilization of eggs or egg-equivalents. Third, eggs must exhibit the same ploidy level as the mother, i.e., meiotic reduction is avoided. Fourth, all of these conditions must be met simultaneously or almost simultaneously. Otherwise, each is deleterious if expressed in the absence of others.

Removals of the constraints on activation of the latent apomixis could restore parthenogenetic apomixis and result in diploid parthenogenesis and production of F1 hybrids grown as a single line.

It is therefore, a primary objective of this invention to provide conditions which would allow activation of the latent apomixis leading to diploid parthenogenesis, resulting in a convenient method for a simplified production of hybrid seeds by latent diploid parthenogenesis and parthenote cleavage.

All publications, patents and patent application cited in the specification are hereby incorporated by reference in their entirety.

SUMMARY

One aspect of the current invention is a method for simplified production of hybrid seeds by diploid parthenogenesis.

Another aspect of the current invention is a method for production of hybrid seeds by diploid parthenogenesis resulting from environmental activation of latent apomictic behavior.

Still another aspect of the current invention is a method providing conditions for activation of apomictic behavior, wherein the conditions results in diploid parthenogenesis.

Still yet another aspect of the current invention is a method for restoration of early developmental ancestral characteristics combined with new developmental cenogenesis not found in the ancestral forms.

Still yet another aspect of the current invention is a method for diploid parthenogenesis that also leads to the normal expression of embryo development and cleavage.

DEFINITIONS

As used herein:

"Parthenogenesis" means reproduction by the development of an unfertilized egg, seed or spore or their equivalent. Replacing an egg cell or its equivalent with another cell is an efficient and parsimonious way of introducing the capacity for parthenogenesis. Examples of parthenogenesis are haploid genotypes with meiosis, diploid genotypes without meiosis or by variations in meiosis, such as restitutional meiosis to give a diploid.

"Parthenote" means embryo equivalent.

"Aposporous" means formed from a sporophyte cell which has not undergone reduction division, that is apomixis without spore formation.

"Apomixis" means nonsexual reproduction.

"Diploid" means having twice a number of chromosomes normally occurring in mature germ cells.

"Sporophyte" means the spore-bearing generation that is diploid and reproduces the spores.

"Archegonium" means the flask-shaped reproductive organ in mosses, ferns, gymnosperm, etc.

"Transdifferentiation" means flexibility in cell differentiation. The term has been adopted from Okada, *Transdifferentiation,* Claredon Press, Oxford, (1991) to represent a switch after cell differentiation from one cell type into another.

"Diploid parthenogenesis" means the formation of eggs or egg-equivalent cells that regenerate diploid plants without fertilization while mimicking the features of reproductive development.

"Pycnotic" means becoming dense.

"Neocytoplasm" means formation of a new cytoplasm around the nucleus of a zygote and/or parthenote.

"Coenocytic stage" means the free nuclear state in reproductive development.

"Leader cell" means a type of cell ($pE_1$) that imitates growth and a developmental program.

"Fate-mapping" means following the fate of cells by time-lapse according to a model reference.

"Cenogenesis" means the development of structures or new expressions in the embryonic of the organism that are adaptive and do not appear in the evolutionary history of the organism.

"Proembryo" means the early developmental stages of the zygote or its equivalent before the elongation of the axial tier of cells in the early embryo.

"Early embryo" means development from the proembryo and is characterized by an axial tier of cells that elongate to form the characteristic structure of the species before embryo differentiation with meristems and cotyledons appears.

"Progenesis" means the initiation that is brought to an earlier stage of development when referenced to phylogeny.

"Cleavage polyembryony" means the reconstitution of new embryos from a single embryo by cleavage of the early embryo into two or more identical embryos.

"Somatic polyembryogenesis" or "SPE" means the origin of the cell as being somatic as opposed to reproductive cells, such as, for example, gametes, egg, and sperm. The origin of the cell is by cleavage of the embryo to reconstitute a new embryo as is typical in conifers. The origin as defined in this pattern does not involve a callus stage or phase.

"DCR" means and represents a code for a basal DCR culture medium of specific formulation as listed in medium section that can be varied and supplemented to sustain growth and development of plant cells under aseptic conditions. Basal DCR is defined culture medium distinctly different from Murashige/Skoog formulations. The basal DCR medium can be modified and supplemented with factors that improve embryonic growth. These factors are reconstituted from analyses of seeds and used as supplements to the DCR formulation especially if genotypes are recalcitrant to the DCR or MS or any other formulation.

"MS" means Murashige-Skoog medium.

"Totipotent capacity" means the potential to recapitulate and express the full life cycle of the genotype in question.

"BAP" means benzylaminopurine.

"ABA" means abscisic acid.

"2,4-D" means 2,4-dichlorophenoxyacetic acid.

"KN" means kinetin.

"NAA" means naphthalene-2-acetic acid.

"BA" means $N^6$-benzyladenine.

"DMH" means one of several possible specific medium modifications for diploid parthenogenesis in genotypes of Douglas-Fir.

"BMH" means one of several possible specific medium modifications for diploid parthenogenesis in *Picea Abies*.

"LDH" means one of several possible specific medium modifications for diploid parthenogenesis in Loblolly Pine.

"BO4" means one of several possible specific medium modifications for expression of *Picea Abies* embryos.

BRIEF DESCRIPTION OF DRAWINGS

FIG. 5 shows a photograph of an acetocarmine cytochemical staining of nuclei formed within central cells.

FIG. 6 is a photograph of a nucleus, a new cytoplasm and cell wall released as $pE_L$ double-stained with acetocarmine and Evan's Blue.

FIG. 21 is a model with postulates for climate induced adaptive plasticity in sexual and latent asexual reproduction.

DETAILED DESCRIPTION OF THE INVENTION

Figure 1:
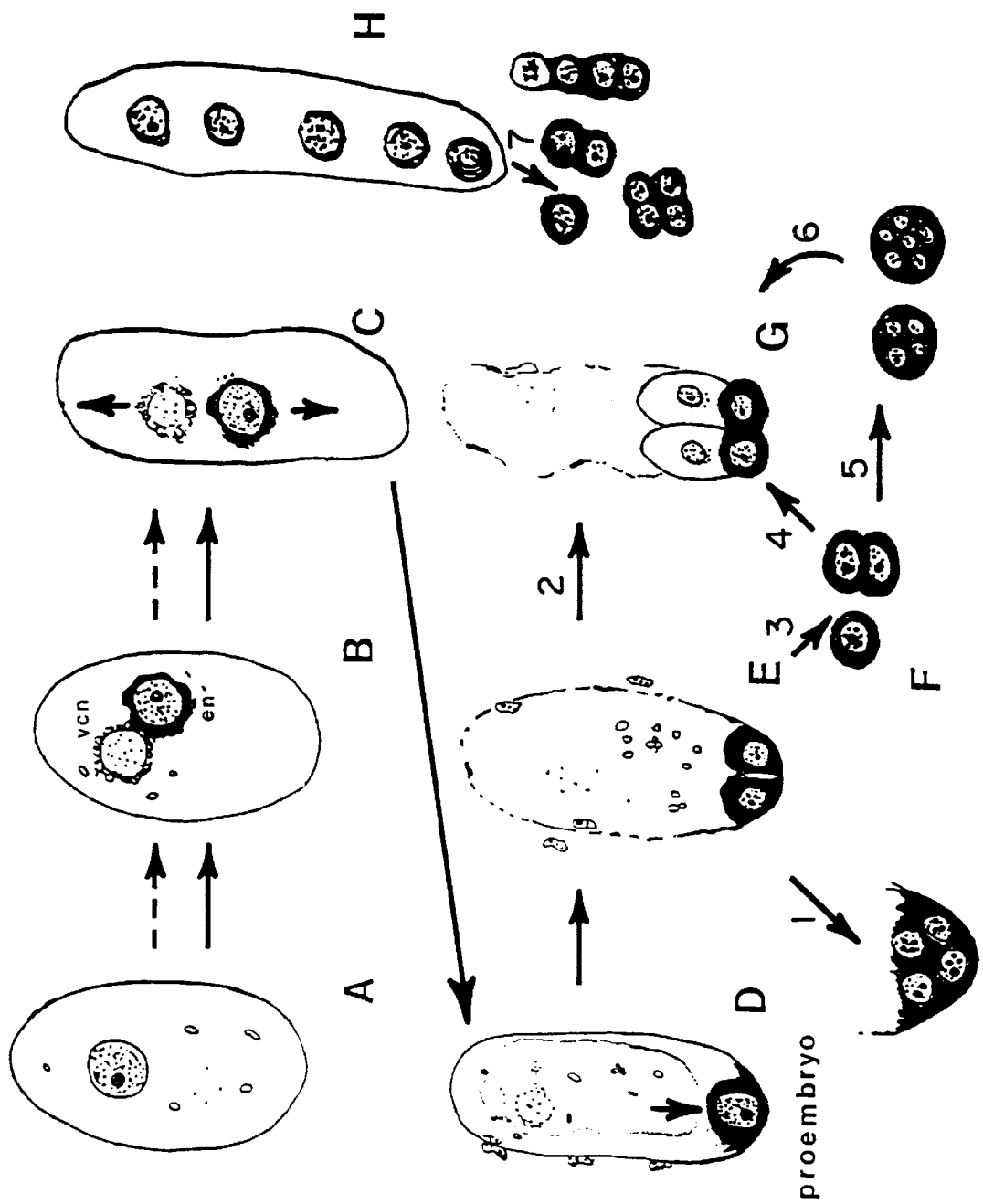
FIG. 1 is a scheme illustrating variations in the expression of diploid parthenogenesis in cell suspension.

The current invention concerns a method for hybrid seed production by asexual diploid parthenogenesis. The method involves environmental manipulation of the gymnosperms reproduction by inducing asexual reproduction by artificially controlling environmental conditions. Consequently, the invention concerns the discovery that manipulation of environmental conditions alone induces a diploid somatic cell of gymnosperms to behave as a central cell in the archegonium of the same species.

Until this discovery, apomixis involving asexual diploid parthenogenesis in gymnosperms has been regarded as absent (*The Evolution of Asexual Reproduction in Plants*, Supra) and under the normal conditions asexual reproduction has rarely been shown to extend beyond polyembryony. The current invention discovered and subsequently confirmed, for the first time, that the potential to deviate from the normal sexual cycle is present in conifers, provided that appropriate environmental conditions are present.

Briefly, it has been now shown that in gymnosperm single cell cultures, obtained from cleaving embryonal-suspensor masses, given appropriate environment, individual cells can behave in a way that shows a remarkable parallel to events in the archegonium. The nucleus of the initially uninucleate cell divides. One nucleus degenerates but the other accumulates an organized cytoplasm (neocytoplasm) and develops a thin cell wall and organization of the leader cells. When released into the medium these leader cells display free-nuclear division and initiate renewed embryo formation. The isolated leader cell is thus behaving in a manner almost identical with that of the central cell in the archegonium of the female gametophyte, despite its having a diploid nucleus. The divergence from the normal cycle lies in the surviving nucleus, which is analogous to the egg nucleus in normal sexual reproduction of the conifer, developing without fertilization.

These events occur due to induced artificial environmental conditions initiating asexual reproduction by promoting the latent apomictic behavior. These conditions include among others, high temperatures, specific media containing among others low organic nitrogen and high interstitial levels of carbon dioxide. In these conditions, a gymnosperm has been found to be capable of behavior which is similar to the formation of an aposporous embryo sac in an angiosperm (e.g., *Ranunculus auricomus*), in that the diploid pseudo-egg nucleus become capable of parthenogenesis.

In the system of the invention, the parthenogenesis behavior of the product of the division of the psedocentral cell revealed that it was not a true egg cell, but a totipotent cell equivalent to those which initiate embryogenesis in single cell cultures.

I. Method of the Invention

The method according to this invention involves induction of diploid parthenogenesis by providing specific environmental conditions leading to nonsexual diploid parthenogenesis resulting in asexual production of gymnosperm seeds and plants having the identical genetic traits. The cell and tissue culture technology indicates that genotypes inherent in the selected tree can be cloned by apomictic parthenogenesis under normal circumstances and environmental conditions, most gymnosperms throughout their life cycle are highly recalcitrant to changes in their normal sexual reproduction.

The first problem to overcome this recalcitrance was to identify cells in the life cycle of gymnosperms that do not show this recalcitrance. Such cells were found to be present in the early embryonic stages. These early embryonic stages are normally present in the developing seeds on mature trees. The most suitable embryos can be rescued from the developing seed but cells having the capacity for expressing totipotency may be recovered also from cones, shoots or roots provided that the embryonal state enabling totipotency can be restored. Normally, the best time to rescue these embryos is from immediately after the seed fertilization on the trees to up to 3 months after fertilization. In the seeds obtained during this time-frame, it is easy to induce growth and to achieve diploid parthenogenesis. When such embryos are harvested, afterwards, it is harder to induce the rescued embryonic tissues to grow. The genotype and identification of totipotent capacity of cells that are used in this method are the very first important steps.

Rescue of the earliest stages involves recognition of an embryonal-suspensor mass (ESM) and identification whether it will or will not show monozygotic cleavage polyembryony. Recognition of this stage is important in order to distinguish it later on from a callus, because at this stage there is no callus. When properly grown on the culture medium and maintaining contact of ESM with original explant, ESM grows into proliferating totipotent mass of cells. Under these conditions, ESM does not form an embryogenic callus but continues to proliferate by the cleavage process. This process is called somatic polyembryogenesis. In somatic polyembryogenesis, clones are generated not from a callus that is induced to form clones, but from the inherent cleavage process.

The subject matter of this invention involves still another cloning process than somatic polyembrogenesis. The new process called diploid parthenogenesis is latent and inherent in the embryonal-suspensor mass. In diploid parthenogenesis, clonal embryos (parthenotes) are also recovered from cells of the embryonal-suspensor mass. Cells capable of diploid parthenogenesis are released from the embryonal-suspensor mass into the culture medium and by variation in the standard meiotic process produce offsprings that are diploid rather than haploid. Offsprings are genetically similar to the genotype of the original embryonal-suspensor mass but their origination is distinct because they pass through an egg-equivalent stage and release offspring without fertilization. During diploid parthenogenesis, the embryonal-suspensor mass, when rescued and cultured according to the invention, as opposed to being excised as part of a tissue, comprises proembryonal and early embryonal stages of development.

The second problem to overcome is to provide and promote conditions and environment which suppress sexual reproduction and initiate the asexual diploid parthenogenesis. This is done primarily by providing specific nutrients medium and by changing temperature. Once the embryonal-suspensor mass and its equivalents, such as protodermal cells excised in early embryonic stage from ripening or ripe embryos, are rescued, a culture medium to support the growth of the cells is defined. Because of the very large genetic heterogeneity and range of gymnosperms, there is not a one culture medium formulation that can be applied to all genotypes, and specific medium for each genotype must be identified. The choice of media is done by screening the isolated cells against a variety of common culture media. Often the existing culture media screen gives inadequate results so that the culture media needs to be modified. For example, various supplements to the culture media are needed depending on the gymnosperm genotype. These broad supplements comprise the common minerals such as calcium, magnesium, nitrate and other organic factors such as urea, amino acids, amides ranging from trace to 1 or 2 g per liter of medium depending on the explant, genotype and dilution of the culture medium. Supplements also comprise plant growth regulators such as 2,4-D, ABA, BAP, KN, thidiazuron, and indolebutyric acid. Screening of the media determined, for example, that the addition of organic nitrogen sources, such as the free amino acids in the form of a modified casein hydrolysate, and the addition of cyclitols, such as myo-inositol, improve the cleavage process in Norway spruce. Addition of plant growth regulators promote growth of the proembryo and their eventual removal facilitates the transition from dependency of embryos on the culture medium for heterotrophic growth to simpler medium forcing photoautotrophic growth so that plants can be planted in their natural environment.

Because of the great genetic variability of gymnosperm and their historical recalcitrance to diploid parthenogenesis, there is a need for modified culture media. A general screening process to find optimal medium for each genotype is undertaken to find the best supplemented nutrient formulation. This is done by taking into account the nutrition present around the developing embryo based on chemical analyses of soil, water, and designing the medium containing the same or similar nutrients and assaying various permutations and combinations of the nutritious media with plant growth regulators added to the culture medium. Typically, cells are assayed against concentration gradients of the factor under question whether the nutrient or growth regulator, that is the cells are assayed against the log concentrations of the certain nutrient and/or plant growth regulator and any other supplemental factors, such as amino acid supplement. The response to this latin square type of supplement and type of additive gives a general idea of what are the supplement's best concentrations and what supplements and additives ratios are needed to give optimal responses and conditions. Best concentrations are determined empirically for each genotype as appropriate by the following steps.

Explant is selected from genotype, response of genotype to variety of common culture media is assayed and the best medium is chosen. If the medium does not contain optimal levels of supplements and additives, then the selected medium is modified. For example, response to increasing levels of calcium vs. potassium in the culture medium are determined and best response is selected. The formulation that gives the best response is then used. This process is repeated with other nutrients or plant growth regulators so that the response that is closest to normal embryonic growth is determined. The selected best formulation is used for this genotype. Similarly, other genotypes are tested and medium for these genotypes is modified. Medium formulations are changed usually by simplification of the medium formula to encourage full embryo development. This process is empirical and is used by those skilled in this art.

When the general range of media supplements and additives is obtained, a narrow range of concentrations is defined which meets requirements of each individual species. The important step is to obtain a medium formulation that is best suited to the genetic diversity for the particular species. The studied range of concentrations and ratios should be as wide as possible. For example, a medium such as 1/2 LP has been adjusted to a genotype to a modification which gives better response with double the calcium salt concentration. To this medium, a standard level of 200 mg/L of amino acids mix or as a casein hydrolysate might be added. A quick test may show that this level is not optimal and the test results show that 2× levels of amino acid mix is better. Again the medium formulation becomes modified. For plant growth regulators concentrations starting with nil, 0.01, 0.1, 1.0 or 10 mg per liter would be used and if it is found that the best response is at 1 mg/l then the work is repeated to see if the level can be further optimized between 0.1 and 10 mg/l. The results, for example, could indicate that 2 mg/l is best. Now interactions with other growth regulators are looked at and the process is repeated until the desired results are obtained. For these reasons, the formulations are usually always modified. Because of the great genetic variability in most gymnosperm populations the world over, the media has always to be modified to optimize the responses for polyembryogenesis and diploid parthenogenesis. A final modified formulation is so different from the starting formulation, that it is given a new designation for simplicity. For example, basal DCR becomes the new formulation. But because other genotypes in the species from other geographic location do not have the same requirements, the DCR medium may have to be modified again and again to determine what the optimal concentration of nutrients and growth regulation is. Modifications are sought first at a broad level, for example, log concentrations. At one log concentration, a more specific level is sought, for example nil to 10 mg/L. Nil levels are always used because it is a control and sometimes it is better than any level of additive. Hence ranges are first nil, 0.01 mg/L to 20 mg/L for plant growth regulators but for amino acids and inorganic salts the range can be from nil to 1 or 2 grams per liter. In this way, all supplements and additives concentration is determined.

This process has resulted in the formulation of several generic media, such as media designated as MS, DMH, DCR, 0.5×MS, LP, etc. as per definition, that serve the above general purpose. These basic media are used in all initial studies to determine the optimal medium because within a species, the genotypes may require different formulations, such as, DCR medium modified to B5 medium. The best and optimal media for each gymnosperm species must be individually determined. One reason for this specific medium requirement relates to the local site adaptation of individual trees. For example, spruce may grow on calcareous or non-calcareous soils. Tissues taken from the trees for culture grown of the two types of soil requires different levels of calcium in the medium for optimal growth even though the tree is the same spruce species.

Following the choice of culture media, the steps are taken needed to unlock the expression of developmental potential against a model reference for that species. Model reference is a response to a predefined mode, such as zygotic embryo development or products of meiotic development. Obtained results are evaluated and it is determined whether they are in accordance with the model, that is, the obtained data are always model referenced to be sure results are true-to-genotype or arbitrary type by inference. In sexual reproduction, most cell culture and propagation are related to globular, torpedo stage in somatic embryogenesis or to stages 1, 2, or 3 for shoot induction or root induction in micropropagation. The current invention finds this approach unsuitable for gymnosperms because they have primitive characteristics usually not found in angiosperms. Gymnosperms are characterized by free nuclear proembryos, axial tier development of suspensors, and cleavage polyembryony. This means that in the cloning process, the results are model-referenced to what is known specifically for the species of interest. In the absence of such model reference, as often very little is known about gymnosperms, another approach is needed. Therefore, the current studies had to be model-referenced to the phylogeny and evolutionary ontology of the gymnosperms.

Model referencing can be done not only for embryogenesis or any developmental stage sought by the investigator but also to their phylogeny and evolutionary history. The model is obtained from the literature on comparative evolution. For example, Norway spruce's ancestors 200 million years ago are now extinct but some primitive gymnosperms are still living and show a specific pattern of development. This pattern becomes one of several models to which experimental results with Norway spruce can be matched. Experiments take into consideration the climatic and nutritional conditions of distant past ancestors and these conditions are included in the medium and culture formulations. Food supply of ancestral forms, such as Ginkgo, Araucaria are chemically analyzed and reconstituted for feeding back to Norway spruce a new supplement, that is they are added to DCR medium and the levels for best response to match the model are sought. Where data for ancestral species or climates are not available, these are inferred from what is already known, such as for example, the Cretaceous, where the carbon dioxide levels and temperatures are known to be higher than today. The gas and temperature levels that Norway spruce cell are exposes to are increased and the development of cells is fate-mapped to see if they behave like normal spruce or if they show new responses. If the responses are new, it is determined if these responses match any of the known ancestral developmental patterns, often called basal plan in early embryony. If so, then it is clear that these patterns, while not expressed in seeds found in Finland still can be expressed by the genotype under the current artificial conditions, that is the expression of new or old pattern in the evolutionary chain are latent and actually exist in Norway spruce.

The model referencing of experimental data may be based on a model that is inferred from the literature or actual observations because not all data are available. This is not an exact model to base results upon. If very good data are available for early development, as in Norway spruce, Douglas fir, etc., this data serves as a model to use its parameters, such as for example amino acid supply to the embryo, and these parameters are then adapted or introduced into the medium formulation, such as DCR, resulting in a modified DCR medium comprised of amino acids that are commonly found in the genotype of species of choice. If, for example, the choice is a fir, then Douglas fir amino acid components are added as a supplement to a DCR medium for the culture of fir cell. When this was done for various species, the model-referencing, inferential and adaptive revealed more clearly the inherent and latent expressions that other methods have not been able to achieve or appreciate.

Unlocking the expression of developmental potential is achieved through several stages where the ESM is separated from zygotic embryos and proliferated by repeated subculture on the chosen medium, preferably in the presence of plant growth medium at a temperature from 22°–28° C., preferably from 23°–26° C. in darkness. The EMS derived proembryos and embryos cultured on the selected optimal medium at temperature between 23°–26° C., in darkness, for 3–4 weeks, one time or repeatedly, give rise to diploid parthenogenesis, the asexual reproduction according to the invention. After proliferation, ESM types suitable for diploid parthenogenesis develop into embryos and parthenotes with shoot and root meristems. These embryos and parthenotes are identified by selective staining with stains staining embryos or parthenote nucleus.

Using a model reference for diploid parthenogenesis and a model for meiosis in the target species which can be found in the literature, a search is made for a source of cells from the tree's life cycle that show parthenogenic behavior by fate-mapping and initially with diagnostic aids. The aids are various cytochemical methods, morphological methods, such as determination of a number of free nuclei at a given stage of cell development, and ontogenetic methods, such as those measured by fate-mapping, that is, watching what happens to cells when they develop.

By observation, the responses are identified in the cell population and cell types showing the desired expressions are isolated mechanically or by lifting off a culture medium so that this cell type can be scaled up for production. Scaling up is done by standard culture methods using the best available culture formulations derived by empirical study and model-referencing the results, as described above. Cells that do not fate-map according to the model-references are discarded.

In somatic polyembryogenesis, the best cell source is the embryonal-suspensor mass, followed by protodermal cells of the embryo. Cells from old stages of the life cycle can also be used but they have to be rejuvenated and/or invigorated before embryony can be restored. The selected embryonal-suspensor mass for cells that reconstitute new embryos, not by induction of callus cells to become and embryo, but by cleavage polyembryony, is then cultured. In cleavage polyembryony cells are derived from a single zygote, that is, not from a mix of cells from fraternal twins. Cleavage polyembryony is well-described for most conifers and this serves as a model reference. Results are matched to the model reference to ensure that the true to type polyembryony is achieved.

Before this invention, some conifer seeds such as spruce and fir did not show and were believed not to possess cleavage polyembryony. During the development of this invention it was found that rescue of the embryonal-suspensor mass onto an artificial medium elicited cleavage processes to multiply the embryos, that is, that species previously considered as noncleavage in seeds in fact had the capacity for cleavage in vitro. This cleavage is distinct from inducing single cells from a callus to become embryonic in terms of genotype and can be distinguished microscopically and cytochemically by reference to models for cleavage polyembryony and callus or tissue having embryonic cells. The result of cleavage polyembryony is the mass clonal propagation of the genotype with opportunities to enhance the robustness of the early stages by increased food supply and by preconditioning treatments that could strengthen survival in the field. This is a considerable improvement over the callus cells which can give more variable genotypes because of the nondeterminate growth and genotype changes well known to cause genotypic aberrations in the propagation literature.

The mass clonal propagation captures the products of meiosis, that is, of a controlled cross in a breeding orchard or in nature. Diploid parthenogenesis influences the process several steps earlier because cells can be isolated that recapitulate variations in the meiotic process. The cells are isolated that behave like eggs or the products of meiosis and/or their progenitors sporogenic cell. In gymnosperms, the progenitor of the egg is a central cell that may or may not be present but can be distinguished by the number of nuclei in the cell and by following their fate to the production of an egg cell. Isolated populations of somatic cells behaving like meiotic products are equivalents and the term egg-equivalent is used for a cell that behaves like an egg but which is out of place in normal development, that is, as would occur in a tree branch as opposed to in a population of somatic cells that normally become embryos. Cells showing diploid parthenogenesis rather than becoming embryos from the start, revert and recapitulate the meiotic variation so they behave like egg according to the natural model. Since there is no fertilization in vitro, their nuclei (egg-equivalent nuclei) can become embryos. The term parthenotes is used to distinguish egg-equivalent products from zygotic products, that is, from embryos or somatic embryos. In both cases, cleavage polyembryony is expressed and the multiplication of embryos or parthenotes is traced back to the number of free nuclei in egg-equivalents and to the cleavage process. The cleavage process is very distinct from the induction of callus model.

Typically, the method for diploid parthenogenesis consists of several general steps.

Step 1 comprises rescue or excision of tissue or ESM from a single archegonium to keep genotypes from not being fraternal twins.

Step 2 comprises aseptic culture and sorting and searching for cell mass types according to models for diploid parthenogenesis, SPE and callus.

Figure 20:
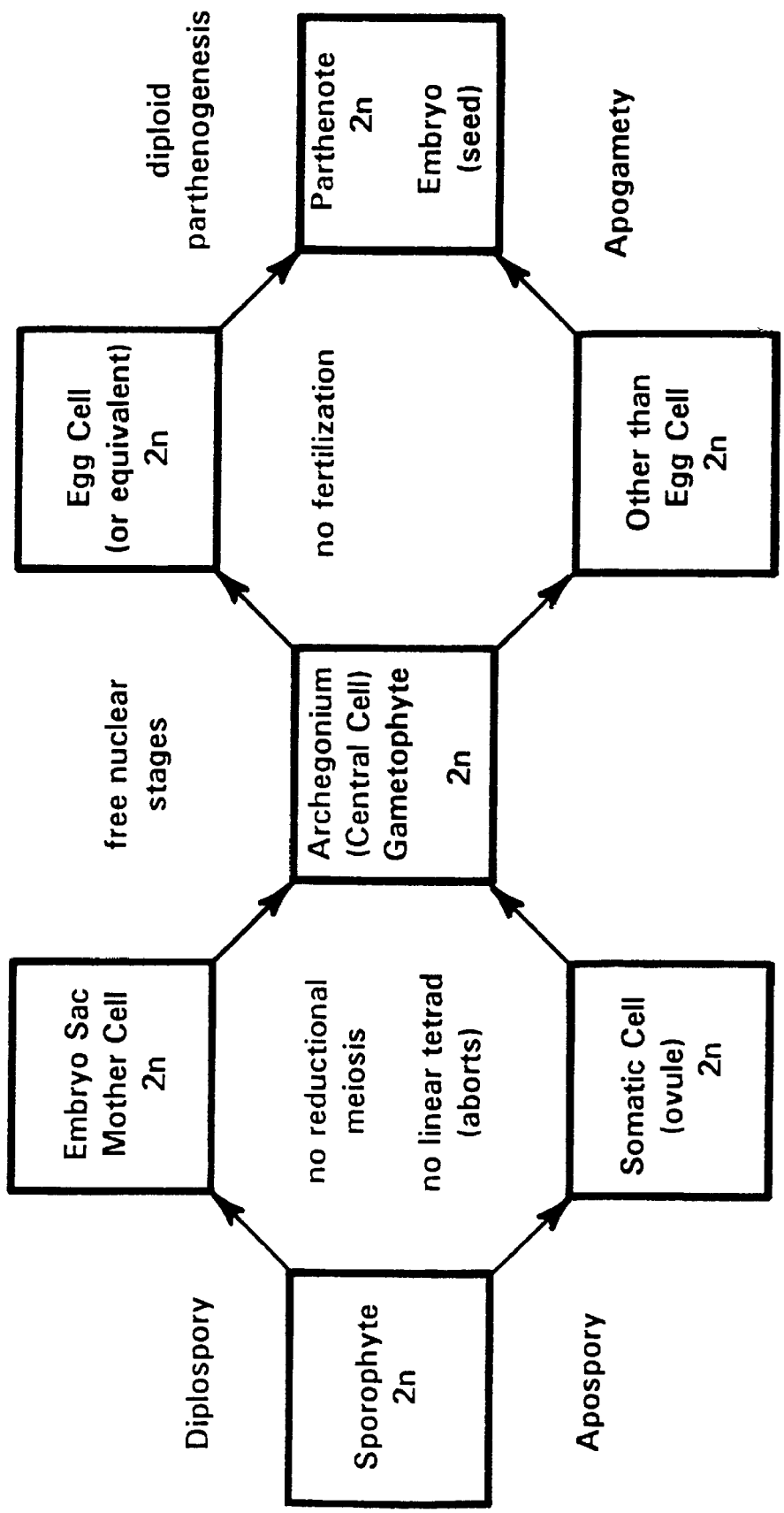
FIG. 20 shows the origin of diploid parthenogenesis as steps and stages.

Step 3 comprises selection of cells enabling diploid parthenogenesis according to FIG. 1 and FIG. 20.

Step 4 comprises selection of cell masses enabling somatic polyembryogenesis and cleavage without the intervention of a callus phase, for example, without cell passing through a nondescript phase of cell division using microscopy and fate mapping if needed.

Step 5 comprises optional search for or against callus. Callus is not useful for diploid parthenogenesis except for the recovery of variable new genotypes introduced by the callusing process. Typically, the same genotype is wanted as the starting genotype with development that is normal or true to genotype. Callus is only useful if the daughter cells retain the capacity to revert to diploid parthenogenesis and SPE but this is an extra step that is not needed and requires additional time and money.

Step 6 comprises continued development of cell types in 3 and 4, above, to parthenotes or proembryos, early embryos, etc. In both cases further embryo multiplication occurs by a distinctive cleavage of the proembryo or early embryo. The capacity for cleavage can be traced back to the divisions of the free nuclei in the egg-equivalent state in diploid parthenogenesis.

Step 7 comprises reaching proembryonal stages of diploid parthenogenesis or SPE, once these stages are reached, the further developmental processes are autocatalytic, provided that the nutrition fed to cells during subsequent subculture are simplified from the original medium formulations with amino acid, sugars, etc. to basically the same nutrients found outside the test tube. These nutrients are mainly inorganic and this simplification of medium coincides with the emergence of photoautotrophic expressions enabling the plant to live outside the test tube. The simplification formula can vary widely depending on the practitioner and genotype but the same basic principle of simplification of the initially heterotrophic food supply always holds up. The initial food supply in the medium also contributes to robust plants for planting in the soil, for example, the plants can be preconditioned.

In summary the method of the invention involves the detection of cell type, isolation and scaling up cells, and imposing quality control according to model reference for meiotic and early embryonal development for that genotype. Standard culture methods are used where appropriate. When standard methods are not useful, parameters from the model reference in culture conditions are used and the sequence of developmental events is manipulated to get the results sought. Often once the cell type is detected and cultured with designed culture conditions, the process continues spontaneously and later steps are subject to routine methods. In any case, quality control is imposed to verify that the cells are not callus cells or that the process does not involve a callus phase.

A. Culture Media

Because of the diversity of gymnosperm species, their soil conditions and their general recalcitrancy to be asexually reproduced, the media for diploid parthenogenesis must be specifically designed and almost custom made for each individual species. Each gymnosperm species specific media is derived from a modified basic media of which examples are listed below. It is to be understood that given basic and/or specific media are exemplary only and that different species or the same species embryos removed from different site may require otherwise modified media and these media are intended to be within a scope of this invention.

A. Basal Media

1. Basal Murashige-Skoog Medium

Basal Murashige-Skoog (MS) medium is according to *Physiol. Plant*, 15:473 (1962).

The following represent modifications of basal MS medium:

Murashige-Skoog-1 Medium

Murashige-Skoog-1 medium represents modification 1, half-strength basal MS medium with added casein hydrolysate, (500 mg/l), L-glutamine (450 mg/l), myo-inositol (1000 mg/l), sucrose 3%.

Murashige-Skoog-2 Medium

MS-1 with added 2,4-D ($15 \times 10^{-5}$M), kinetin and $N^6$-benzyladenine ($2 \times 10^{-5}$M) each.

Murashige-Skoog-3 Medium

MS-1 with added 2,4-D ($15 \times 10^{-6}$M), kinetin and $N^6$-benzyladenine ($2 \times 10^{-6}$M) each.

Murashige-Skoog-4 Medium

MS-1 with added NAA ($1 \times 10^{-6}$), kinetin and $N^6$-benzyladenine ($2 \times 10^{-5}$M) each.

2. Basal DCR Medium

Basal DCR medium is distinctively different from MS and has the composition cited in *Plant Cell Reports* 4: 177 (1985).

| | mg/L |
|---|---|
| NH$_4$NO$_3$ | 400 |
| KNO$_3$ | 340 |
| Ca(NO$_3$)$_2$.4H$_2$O | 556 |
| KH$_2$PO$_4$ | 170 |
| MgSO$_4$.7H$_2$O | 370 |
| CaCl$_2$.2H$_2$O | 85 |
| H$_3$BO$_3$ | 6.2 |
| MnSO$_4$.H$_2$O | 22.3 |
| ZnSO$_4$.7H$_2$O | 8.6 |
| CuSO$_4$.5H$_2$O | 0.25 |
| KI | 0.83 |
| FeSO$_4$.7H$_2$O | 27.8 |
| Na$_2$EDTA | 37.3 |
| CoCl$_2$.6H$_2$O | 0.025 |
| NiCl$_2$ | 0.025 |
| NaMoO$_4$.2H$_2$O | 0.25 |
| Thiamine.HCl | 1.0 |
| Pyridoxine.HCl | 0.5 |
| Nicotinic Acid | 0.5 |
| Glycine | 2.0 |
| myo-Inositol | 200 |
| Sucrose | 30 g/L |

The following represent modification of a basal DCR medium:

DCR-1 Medium

Half-strength basal DCR medium with added casein hydrolysate (500 mg/l), L-glutamine (450 mg/l), myo-inositol (1000 mg/l) and sucrose 3%.

DCR-2 Medium

DCR-1 medium with added 2,4-D ($5\times10^{-5}$M), kinetin and N$^6$-benzyladenine ($2\times10^{-5}$M) each.

DCR-3 Medium

DCR-1 medium with added 2,4-D ($5\times10^{-6}$M), kinetin and N$^6$-benzyladenine ($2\times10^{-6}$M) each.

DCR-4 Medium

DCR-1 medium with added NAA ($1\times10^{-6}$M), kinetin and N$^6$-benzyladenine ($2\times10^{-5}$M).

MS or DCR medium is adjusted to pH 5.7 or 6.0, respectively with KCl and KOH, Bacto agar 0.6% is added (w/v) and autoclaved (1●1 kg cm$^{-2}$) at 121° C. for 20 minutes.

These solutions represent the preferred concentrations of nutrients and growth regulators. However, the concentrations of growth regulators may be varied so long as diploid parthenogenesis is maintained. For example, certain auxins and cytokinins may be substituted for each other, various amino acids may be used as a nitrogenous source and different cyclitols may be substituted for myo-inositol.

b. Specific Media

Douglas Fir-DMH Media

For preparation of 1 liter of DMH media, which is based on DCR modified medium diluted 1:1,v/v.

| DCR Media (0.5%) | | |
|---|---|---|
| Nitrate | (50% Stock) | 10 ml |
| Sulfate | (50% Stock) | 10 ml |
| PBM0 | (50% Stock) | 10 ml |
| Halide | (50% Stock) | 10 ml |
| FeEDTA | (1000% Stock) | 5 ml |
| Vitamin | (1000% Stock) | 1 ml |
| Sucrose | (3%) | 1 ml |
| Inositol | | 1000 mg |
| Casein Hydrolysate | | 500 mg |
| L-glutamine | | 450 mg |
| 2,4-D (1 µmole/ml stock) | | 5 ml |
| Kinetin (1 µmole/ml stock) | | 2 ml |
| BAP (1 µmole/ml stock) | | 2 ml |
| Agar | | 0.6% |
| pH 5.75 | | |

Water up to 1000 ml. DMH media is adjusted to pH 5.75 before autoclaving.

Loblolly Pine-LPH Media

For the Preparation of 1 liter of LPH media which is LP media diluted 1:1,v/v. LP Media (0.5%)

| | | |
|---|---|---|
| LP Medium | 10% Stock | 50 ml |
| FeEDTA | 100% Stock | 5 ml |
| Vitamin | 1000% Stock | 1 ml |
| Sucrose | | 3% |
| Inositol | | 1000 mg |
| Casein acid hydrolysate | | 500 mg |
| L-glutamine | | 450 mg |
| 2,4-D 1 µmole/ml Stock | | 5 ml |
| Kinetin 1 µmole/ml Stock | | 2 ml |
| BAP 1 µmole/ml Stock | | 2 ml |
| Agar | | 0.6% |
| pH 5.7 | | |

Water up to 1000 ml. LPH media is adjusted to pH 5.70 before autoclaving.

*Picea Abies*-BMH Media

For the preparation of 1 liter of BMH media which is based on the original MS medium that is diluted 1:1,v/v.

| (0.5% MS Media) | | |
|---|---|---|
| Macro Salt | 4% Stock | 125 ml |
| FeEDTA | 100% Stock | 5 ml |
| Vitamin | 1000% Stock | 1 ml |
| Micro Salts | 1000% Stock | 0.5 ml |
| Sucrose | | 3% |
| Inositol | | 1000 mg |
| Casein Hydrolysate | | 500 mg |
| L-glutamine | | 450 mg |
| 2,4-D 1 µmole/ml stock | | 5 ml |
| Kinetin 1 µmole/ml stock | | 2 ml |
| BAP 1 µmole/ml stock | | 2 ml |
| Agar | | 0.6% |
| pH 5.7 | | |

Water up to 1000 ml. BMH media is adjusted to pH 5.7 before autoclaving.

Stock Solutions

Macro Salts-4% Stock

For the preparation of 4 liters of 4% macro salt stock solution.

| | |
|---|---|
| NH$_4$NO$_3$ | 8.812 g |
| KNO$_3$ | 74.784 g |
| MgSO$_4$—7H$_2$O | 5.920 g |
| KH$_2$PO$_4$ | 2.720 g |

Water up to 4000 ml.

Micro Salts-1000% Stock

For the preparation of 100 ml of 1000% micro salt stock solution.

| | |
|---|---|
| H$_3$BO$_3$ | 0.620 g |
| MnSO$_4$—H$_2$O | 1.690 g |
| ZnSO$_4$—7H$_2$O | 0.860 g |
| Potassium iodide (KI) | 0.083 g |
| NaMoO$_4$—H$_2$O | 0.025 g |
| CuSO$_4$—5H$_2$O | 0.0025 g |
| CaCl$_2$—6H$_2$O | 0.0025 g |

Water up to 100 ml. Store as a filter sterilized solution.

Nitrate 50%-Stock

To prepare 1 liter of 50% sulfate stock solution.

| | |
|---|---|
| NH$_4$NO$_3$ | 20.0 g |
| Ca(NO$_3$)$_2$—4H$_2$O | 27.8 g |
| KNO$_3$ | 17.0 g |

Water up to 1000 ml.

Sulfate 50%-Stock

To prepare 1 liter of 50% sulfate stock solution.

| | |
|---|---|
| MgSO$_4$—7H$_2$O | 18.5 g |
| MnSO$_4$—H$_2$O | 1.115 g |
| ZnSO$_4$—7H$_2$O | 0.43 g |
| CaSO$_4$—5H$_2$O | 0.0125 g |

Water up to 1000 ml.

Halide 50% Stock

To prepare 1 liter of 50% halide stock solution.

| | |
|---|---|
| CaCl—2H$_2$O | 5.5 g |
| KI | 0.0415 g |
| CaCl—6H$_2$O | 0.00125 g |
| NiCl | 0.00125 g |

Water up to 1000 ml.

PBMO Stock 50% Stock

To Prepare 1 liter of 50% phosphate, borate, molybdenate stock solution.

| | |
|---|---|
| KH$_2$PO$_4$ | 8.5 g |
| H$_3$BO$_4$ | 0.31 g |
| Na$_2$MoO$_4$ | 0.0125 g |

BAP Stock-1 µmole/ml

To prepare 100 ml of BAP:

| | |
|---|---|
| BAP | 22.25 mg |
| HCl 0.1 N | 2 ml |

Dissolved BAP in 2 ml of 0.1N HCl. Water up to 100 ml.

Kinetin Stock

To prepare 100 ml of kinetin stock solution:

| | |
|---|---|
| Kinetin | 22.54 mg |
| KOH | 2 ml |

Dissolve kinetin in 2 ml of 0.1N KOH. Water up to 100 ml.

2,4-D Stock-1 µmole/ml

To prepare 100 ml of 2,4-D stock solution.

| | |
|---|---|
| 2,4-D | 22.1 mg |
| Ethanol | 70% |

Dissolve 2,4-D in 2 ml of 70% ethanol, add water up to 100 ml.

NAA Stock Solution

To prepare 100 ml of stock NAA solution:

| | |
|---|---|
| NAA | 20 mg |
| Ethanol | 5 ml |

Add water to 100 ml.

Douglas Fir and Loblolly Pine

Media for Subculture of Shoots

To prepare 500 ml of media:

| | | |
|---|---|---|
| PBMO | 50% Stock | 10 ml |
| Halide | 50% Stock | 10 ml |
| Nitrate | 50% Stock | 10 ml |
| Sulfate | 50% Stock | 10 ml |
| Myo-inositol | | 0.10 g |
| FeEDTA | 100% Stock | 5.0 ml |
| Vitamins | 1000% Stock | 0.5 ml |
| Sucrose | | 2.0% |
| Agar | | 0.6% |
| BAP | 0.2 mg/ml stock | 0.25 ml |
| NAA | 0.1 mg/ml stock | 0.10 ml |
| pH 5.8–5.9 | | |

Add water up to 500 ml. Adjust pH before autoclaving. Subculture every 5 to 6 weeks.

BO4 Media

Modified BMH Medium For Expression of *Picea Abies* Embryos

Supplements to the BMH medium:

| | |
|---|---|
| Arginine | 40 mg |
| Asparagine | 100 mg |

Water up to 1000 ml. The modification also includes a change in eh macro salt to contain only 0.5% $KNO_3$.

Nutrient Medium (DMH)

For Rescued Embryonal-Suspensor Masses of Douglas-Fir

| | mg/1000 ml |
|---|---|
| Nitrates | |
| $NH_4NO_3$ | 220 |
| $Ca(NO_3)_3 \cdot 4H_2O$ | 278 |
| $KNO_3$ | 170 |
| Sulfates | |
| $MgSO_4 \cdot 7H_2O$ | 185 |
| $MnSO_4 \cdot H_2O$ | 11.2 |
| $ZnSO_4 \cdot 7H_2O$ | 4.3 |
| $CuSO_4 \cdot 5H_2O$ | 0.013 |
| Halides | |
| $CaCl \cdot 2H_2O$ | 55 |
| KI | 0.41 |
| $CoCl_2 6H_2O$ | 0.012 |
| NiCl | 0.012 |
| Phosphate, Borate, Molybdenate | |
| $KH_2PO_4$ | 85 |
| $H_3BO_3$ | 3.1 |
| $NaMnO_4$ | 0.12 |
| Fe.EDTA | |
| $FeSO_4 \cdot 7H_2O$ | 13.96 |
| $Na_2EDTA \cdot 2H_2O$ | 18.62 |
| Vitamins | |
| Thiamine.HCl | 1.00 |
| Nicotinic acid | 0.5 |
| Pyridoxine.HCl | 0.50 |
| Carbon and Nitrogen Sources | |
| Sucrose | 30,000 |
| myo-inositol | 1,000 |
| Casein hydrolysate | 500 |
| L-glutamine | 450 |
| Glycine | 2 |
| L-tryptophan* | 1 |

*Tyrptophan is added optionally if required.

Nutrient medium (DMH) for the culture of rescued embryonal-suspensor masses of Douglas fir is formulated in g/l and adjusted to pH 5.8 before autoclaving.

FeEDTA 100% stock

To prepare 1 liter of 100% FeEDTA stock:

| | |
|---|---|
| $FeSO_4$—$7H_2O$ | 2.780 g |
| $Na_2EDTA$—$2H_2O$ | 3.723 g |

Heat (but do not boil) for about 1 to 2 hours. Not to be stored for more than a month.

Vitamin Stock 1000% stock

To prepare 100 ml of 1000% vitamin stock:

| | |
|---|---|
| Thiamine-HCl | 0.10 g |
| Nicotine Acid | 0.05 g |
| Pyridoxine-HCl | 0.05 g |
| Glycine | 0.20 g |

LP Medium Stock (10×)

To prepare 1 liter LP medium stock:

| | |
|---|---|
| $NH_4NO_3$ | 16.5 g |
| $KNO_3$ | 19.0 g |
| $MgSO_4$—$7H_2O$ | 18.5 g |
| $KH_2PO_4$ | 3.4 g |
| $CaCl$—$2H_2O$ | 0.22 g |
| $H_3BO_4$ | 0.31 g |
| $MnSO_4$ | 0.21 g |
| $ZnSO_4$ | 0.43 g |
| $Na_2MoO_4$ | 0.0125 g |
| $CuSO_4$—$H_2O$ | 0.005 g |
| $CoCl_2$—$H_2O$ | 0.00125 g |
| KI | 0.0415 g |
| FeEDTA Stock | 5.0 ml/l |
| Vitamin Stock | 1.0 ml/l |
| Water up to | 1000 ml. |

B. General Process for Diploid Parthenogenesis

The general process for diploid parthenogenesis begins with identifying the explant and obtaining a tissue of a selected genotype.

After identifying the explant or rescued tissue source from the selected genotype and establishing aseptic cultures, that is steps 1 to 6 below, the search for potentially parthenogenetic cells begins. This process may already be expressed and inherent in the explant or rescued embryonal suspensor mass. This is verifiable by recovering cells from the explant or embryonal suspensor mass that behave as egg-equivalents or their progenitors, that is central cell equivalents and premeiotic cells, and which multiply embryos (parthenotes) without fertilization. Behavior is traced cytochemically and morphologically by following free nuclear development in these cells. Where diploid parthenogenesis is not apparent or overt, the capacity for this process is sought by searching for cells that have the features of egg cells, for example tubular, large nuclei, tubular megakaryocytes, isolating and scaling these up for fate-mapping and recovery of embryos. Quality control is established by matching the stages of cellular development through classical meiosis, oogenesis, fertilization, and embryony. Because parthenogenesis is rare or considered absent in gymnosperms, the diagnostic steps in the attached chart are important as a model reference.

Explant selection, rescue and culture establishment for diploid parthenogenesis comprises steps 1–6.

1. Cones, seeds, shoots or roots are surface sterilized.

2. Cleaving embryonal-suspensor masses are rescued from mature or immature seeds or obtained by transdifferentiation of cells from cones, shoots or roots or other responsive stages of the life cycle.

3. Embryonal-suspensor mass (ESM) is isolated by maintaining contact of ESM with original explant and culture medium. ESM is characterized as a white, slimy, proliferating totipotent mass of cells emerging from the zygotic proembryo or protodermal cells of shoots and roots. ESM is distinct from nonembryonic callus because callus cells show unorganized growth and must be induced to become embryonic. Moreover, products may vary genotypically because of the callus stage. A callus may be induced to become embryogenic and even polyembryonic but this is not the same as recovering directly an embryonal-suspensor mass.

4. Zygotic embryos may be optionally removed and separated from ESM.

5. The ESM is proliferated with or without zygotic embryos by subculture on agar every nine to ten days. ESM can be transferred to the liquid medium of the same formulation to establish cell suspension cultures. Adjustment of inoculation density (approximately 10 g per 100 ml) and aeration (flask shake rate: 1–50 rpm) are required.

6. ESM types are selected by light microscopic inspection and single or double-staining methods for evidence of somatic polyembryogenesis referenced to cleavage polyembryony and proembryony. Such referencing serves as a quality control to assure that there is no callus or another process other than diploid parthenogenesis. The preferred method is to first stain the cells with a chromatic or glycoprotein stain and then with a viability test stain. The preferred chromatin or glycoprotein stains are acetocarmine or Feulgen but others such as Orcin may be used. The preferred viability test stain is Evan's blue but others, such as neutral red, fluorescein diacetate and janis green B can be used.

7. Diploid parthenogenesis is sought among cells of the established cultures. Cells of the established cultures are examined for egg-equivalent characteristics and behavior as reference to FIGS. 1 and 20. Cells having the attributes of a tubular megakaryocyte, that is, slightly to moderately elongated cell of approximately 80 to 380 microns length with a large nucleus, or their progenitors, that is, small less than 80 micron diameter cells with large nuclei and little cytoplasm, are isolated and fate mapped by microscopic examination to see if a binucleate stage is reached. If the binucleate stage is reached, then the behavior of the free nuclei determines if the cell is an egg-equivalent. One or both of the free nuclei should divide to produce other free nuclei that produce a thin outer layer of cytoplasm (neocytoplasm) and a cell wall. These cells are called parthenote leader cells if they are released from the egg-equivalent cytoplasm to produce new embryos (parthenotes) via a proembryo and early embryo state characteristic of the genotype. The egg-equivalent has 2 nuclei (egg and ventral canal equivalents) one of which (egg nucleus) migrates and divides to produce cells that are released from the egg cytoplasm into the culture medium as parthenotes. This is distinct from the free nuclear stage migration in the proembryo.

8. In the next stage, the parthenote that is somatic embryo equivalent develops. The stages and terminology to describe parthenote development are the same as for zygotic and somatic embryos, that is the common stages are spontaneously developed as the culture medium is simplified from a heterotrophic to photoautotrophic nutrition.

9. Prospective somatic proembryos give rise to basal plan from primary embryonal cells in the ESM. A basal plan is the sequential pattern expressed by cells in early ontogeny. This plan is often characteristic of the species and genotype so that it serves as a useful marked in fate mapping of cells. Embryonal cells are maintained by mitosis in a growth regulator, such as 2,4-D, and arise by intranuclear mitosis with production of a free-nuclear stage with a variable number of nuclei that stain differentially with acetocarmine or Feulgen and Evan's blue.

10. The very early proembryonal stages of the parthenote, that is before the early embryo with its axial tier of cells develops, are characterized by a free nuclear stage. Nuclei migrate as in the ontogenetic basal plan for the genotype. This pattern is characteristic of various conifers and sometimes referred to as conifer-type proembryogenesis. Nuclei that contribute to the formation of the proembryo stain red with acetocarmine and Feulgen reaction. Other nuclei which stain more intensely blue with Evan's blue contribute to the formation of the suspensor or callus.

11. The proembryonal free nuclear migration stage can also occur in the parthenote that is released into the culture medium during the reconstitution of embryony. This is why a fate-mapping is performed to sort out all of the characteristic stages to comply with the model references of steps that normally occur in nature.

12. Parthenote development and cleavage leads to the visible formation of a new ESM. Within the ESM some suspensor cells contain red-staining nuclei. These are the source of the repetitive mitotic process that contributes to the development of polyembryonic clusters normally produced by cleavage during the in situ development of the zygotic seed.

13. As multiple embryos cleave and develop within the ESM, the primary embryonal cells proceed through true-to-type proembryonal stages of development and the nuclei (often staining blue) contribute to the formation of the suspensor in a pattern approximating that described as the primary upper tier.

14. The ESM and its proembryonal potential has been maintained for over 8 years in darkness by subculture. This process is referred to as the repetitive establishment cycle. The quality of cells and potential for embryonal-suspensor mass development can be monitored by single or double diagnostic staining methods.

15. Upon demand and at will, early embryonic spontaneous development is launched by transfer of cells as a ESM or in cell suspension to subsequent media. Media needs to be adjusted and simplified for appropriate levels of plant growth regulators or promotory growth regulators. Media-ESM or cell suspension is maintained in darkness or weak diffuse light till the late embryo stages of development by subculture, for approximately one to two week intervals.

16. When the embryonic masses (ca. 0.5 to 1.0 mm embryo diameter) are obtained their suspensors are already elongated. In some species, this ESM shows signs of lignification of somatic polyembryonic clusters. This imposes some rigidity to the ESM that facilitates subculture especially in cell suspensions. If such a mass develops in prolonged suspension culture, a fabric of ESM is formed that may be difficult to separate. Early embryos and suspensors retain their affinity for red and blue stains.

17. The embryonic masses are launched into late embryogeny by transfer in medium or its appropriate modifications. Cultures are grown in the presence of diffuse white light (e.g., 2, 8, 2.0 and 0.5 $\mu W$ $cm^{-1}$ in the red, blue and far-red spectrum).

18. Each embryo completes its development in three-four weeks and develops a variable number of cotyledons. Conversion of individual embryos is accomplished by several means, e.g., embryos can be encapsulated at this or at an earlier stage (globular (U.S. Pat. No. 4,217,730) for storage at 4° C. or in liquid or until further use. Encapsulated embryos can be converted to plantlets or fed back into the establishment cycle for cloning. The latter is important if potentially useful somaclonal aberrations arise.

19. Converted embryos are planted in soil and grown into plantlets that represent the new generation.

20. Initial process control is achieved by fine tuning culture parameter and by adjusting levels of promotory growth regulators 2,4-D auxins, cytokinins, myo-inositol or another cyclitol(s) and nitrogenous supplements.

Diploid Parthenogenesis Specific Process

1. Explant (a) The seeds are removed from a female cone and collected immediately after and up to three months after fertilization.

(b) The seeds are sterilized- (1) by treatment with 0.1% (w/v) a detergent, such as Linbro, tween, tide, etc. for five minutes and washing with distilled water three–four times;

(2) by treatment with 30% (v/v) $H_2O_2$ for ten minutes, washing with distilled $H_2O$ three–four times;

(3) by sterilization with 0.1% (w/v) $HgCl_2$ for ten minutes and washing with sterile water eight–ten times while maintaining aseptic conditions.

(c) The seed coat is removed, female gametophyte with proembryo, embryo and suspensor is dissected-out and inoculated on MS-2 or DCR medium modified for individual gymnosperm species and the culture is incubated in dark at 23° C. for 3–6 weeks.

(d) After about 3–6 weeks, a white slimy embryonal-suspensor mass (ESM) will develop around the female gametophyte.

(e) Cells from the ESM are examined for egg-equivalent characteristics and behavior. Characteristics and behavior is based on a model of what is known about early reproductive stages. This information can be obtained from the literature or directly by study of the donor or mother trees. Cells having the attributes of a tubular megakaryocyte, that is those slightly to moderately elongated cell of approximately 80 to 380 microns length with a large nucleus, or their progenitors, that is, small less than 80 micron diameter cells with large nuclei and little cytoplasm are isolated and fate-mapped by microscopic examination to determine if a binucleate stage is reached. If the binucleate stage is reached, then the behavior of the free nuclei determines if the cell is an egg-equivalent. One or both of the free nuclei should divide to produce other free nuclei that produces a thin outer layer of cytoplasm (neocytoplasm) and a cell wall. These are parthenote leader cells released from the egg-equivalent cytoplasm to produce new embryos (parthenotes) via a proembryo and early embryo stage characteristic of the genotype. The number of free nuclei giving rise to parthenotes can be increased by exposure of the cells to colchicine of varying concentration from 1 to 200 ml L.

(f) The recovery of embryos and plants are according to protocol in *Plant Cell Reports*, 7: 134 (1988). Some genotypes will require a simpler protocol because of the spontaneous nature of subsequent development and the robustness of the genotype, that is some genotypes become better self-organized and use the simplified formulations and modifications more efficiently than others. Typically, the ESM desired by diploid parthenogenesis, somatic embryogenesis and cleavage polyembrogenesis is transferred to MS-3, or DCR-3 medium.

(g) After three–four more weeks, the stages of early embryony will become dominant. Each early embryo now has elongated cells at one end to form an axial tier with a suspensor and a group of cells called the embryonal group that will form the ripe embryo. Embryonal cells are round with large nuclei and a thin layer of dense cytoplasm.

(h) These early embryos are subcultured every ten–twelve days on MS-3 or DCR-3 medium.

(i) These early embryos are transferred to MS-4 or DCR-4 medium. At this stage, abscisic acid in MS-1 or DCR-1 may be optionally added and used to encourage the complete development of individual somatic embryos.

(j) After subculture three–four times on MS-4 or DCR-4 medium, early embryos develop.

(k) Early embryos are transferred again to a MS-1 or DCR-1 medium with a filter paper support. The concentration of inositol is lowered to about 100 mg/l and embryos are incubated in continuous light (2.8, 2.0, 0.5 $\mu W\ cm^{-2}\ nm^{-1}$ in the blue, red and far-red spectrum) at about 24° to 25° C. At this stage, the temperature and light specifications may vary somewhat but they should be regulated so as to maintain the further development of the embryos.

(l) After seven–eight weeks somatic embryos will elongate and develop multiple cotyledons.

(m) Developed embryos are transferred to MS-1 or DCR-1 basal medium with 0.25 (w/v) activated charcoal 7% sucrose, 100 mg/l inositol without casein hydrolysate and glutamine.

Early embryos develop from the proembryonal stage of parthenotes or somatic embryos. The process starts in section (g). The proembryonal stage comprises of a cell with varying numbers of free nuclei depending on supply of nutrients in the medium and genotype. It is here where the basal plan for the development axial tier of cells of the early embryo is established. The basal plan is considered common to all gymnospersm. The basal plan has variations that are characteristic of genotypes and this information can be used to verify quality control. The free nuclei may migrate in the proembryo before axial tier development of the early embryo. Hence early embryo development starts immediately after the proembryonal stage. Since cells are continually producing embryos, early embryonic development is seen as a continual process and individual early embryos are detected by the formation of a cellular axial tier of cells.

2. Conversion to Plantlets (n) Within five–six weeks complete plantlets develop from somatic embryos.

These plantlets are transferred to plastic pots containing sterile peat moss, vermiculite and perlite (1:2:1 w/w/w) with full light.

3. Diagnostic Techniques

Nonembreyogenic and embryogenic cells can be differentiated by double-staining method. Cells contributing to the various stages of diploid parthenogenesis, embryogenesis or cleavage polyembryony can be differentiated not only by following their fates in preliminary assays with reference to models in FIGS. 1 and 20, but also by cytochemical methods. Double-staining methods have the advantage of identifying two or more cell types in a population so that a good fit to the models can be ascertained. For example, acetocarmine differentiates various type of nuclei so that they can be counted at a free-nuclear stage. First, the cells are excised and stained with 1% (w/v) acetocarmine, heated for few seconds over a flame and washed with medium. Acetocarmine can be replaced by Feulgen reaction. Egg-equivalents are binucleate, and one nucleus may be permeable to Evan's blue. If so, the blue nucleus indicates the occurrence of a ventral canal nuclear equivalent. This can be verified by examining the fates of similar cells in the remaining population to see if this nucleus deteriorates. The other nucleus is the egg-equivalent nucleus which stains strongly with acetocarmine. Similar nuclei in other cells will divide to produce parthenote leader cells before release into the culture medium. Acetocarmine can be replaced by other stains such as Feulgen, Giemsa, and DAPI. Double-staining with acetocarmine and Evan's blue is useful to show the development of the axial tier of the early embryo. First, acetocarmine is used as above. Second, the ESM is stained with 0.5% Evan's blue for few seconds and washed with medium. Embryonic cells stain bright red, suspensors and nonembryogenic cells stain blue. These techniques may also be used to follow organogenesis or just observe plant cells.

A parthenote is distinguished from a somatic embryo by a developmental process. The parthenote develops from a somatic cell that differentiates or transdifferentiates into an egg-equivalent cell or its progenitors with the production of multiple nuclei that become cell walled to produce new embryo equivalents (parthenotes). This is accomplished without meiotic reduction to a haploid and without fertilization. Parthenotes then pass through all of the stages of somatic embryos, that is, proembryo, early embryo, ripe embryo etc. A somatic embryo originates from a parthenote or zygote (fertilized egg) that develops into an embryonal-suspensor mass. This mass contains multiple cells as potential embryos that arise by cleavage polyembryony cells and in cells of the early embryo as a survival process to reconstitute new embryos. In callus, the daughter cells must be induced to become embryonic and historically none of the early embryonal stages have been reported according to a model reference for that genotype or species. This differs from callus, where multiple embryos are formed not by cleavage but by individual induction events that may or may not change to genotype because of the callus phase that is susceptible to aberrations.

Simple polyembryogenesis is very common in conifer species because of fertilization of several eggs. This must be distinguished from cleavage polyembryogeny. Cleavage polyembryony is distinguished from simple polyembryony by definition and origin. Cleavage to reconstitute new clonal embryos derives from a single embryo or parthenote. Simple polyembryony represents the production of multiple embryos as the results of the fertilization of different eggs, that is, it originates from different eggs and the products may be described as being fraternal as with fraternal twins. Hence there is an original and genetic difference between these types of polyembryony. Double-staining of the explant preparation helps to differentiate cells and supported the origin of the ESM in seed tissues and in slimy embryogenic callus from other sources.

II. Asexual Reproduction in Gymnosperms

Under the normal circumstances, conifers do not asexually reproduce by haploid or diploid parthenogenesis. However, it has now been shown that when cells of gymnosperm, such as Finnish Norway spruce genotypes, are grown in a bioreactor under environmental conditions such as high temperatures, carbon dioxide, humidity, abundant food supply, etc., more typical of the Mesozoic period, the barriers to asexual reproduction are removed and the genes for apomictic reproduction are expressed in cells of the rescued early embryo. This signifies that under current climatic conditions, asexual gene expression is latent and suppressed at the seed sources.

Therefore, the following conditions are important and necessary for the release and expression of apomictic parthenogenesis as a general phenomenon.

1. The genotype must have the capacity for parthenogenesis.

2. Fertilization of eggs or egg-equivalents must be prevented. In the current invention, fertilization is avoided and is not possible under the artificial cultural conditions because no pollen is present and nuclear fusion is not seen.

3. Eggs must be of the same ploidy level as the mother or donor, they must be either diploid or polyploid. Cytogenetic verification of diploid or polyploids is done with a Feuglen-Giemsa stain.

4. All of the above must occur more or less simultaneously. This is possible in vitro but in nature where there are long intervals between each step it is difficult or impossible to achieve.

Figures 1, 19:
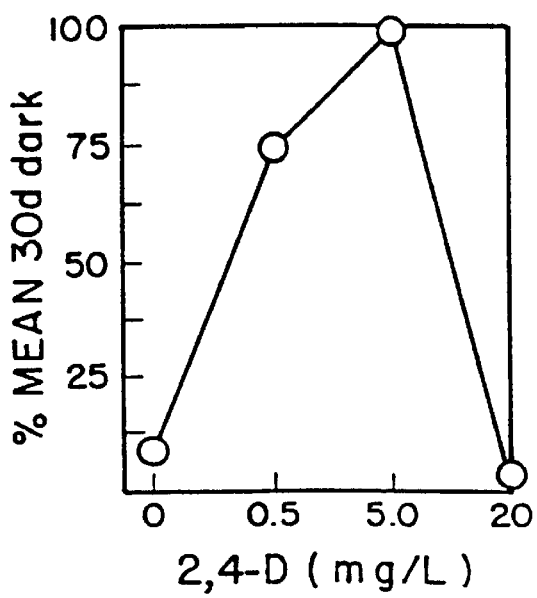
FIG. 19 illustrates recovery rate of early embryo in the presence of various additives.
Figures 2, 19:
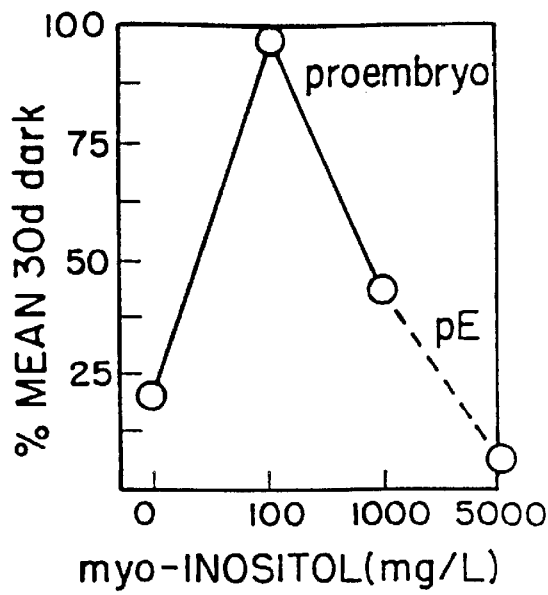
Figures 3, 19:
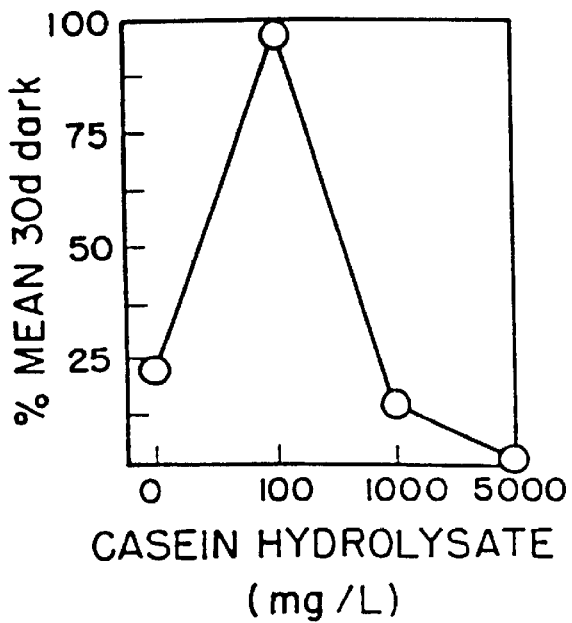
Figures 4, 19:
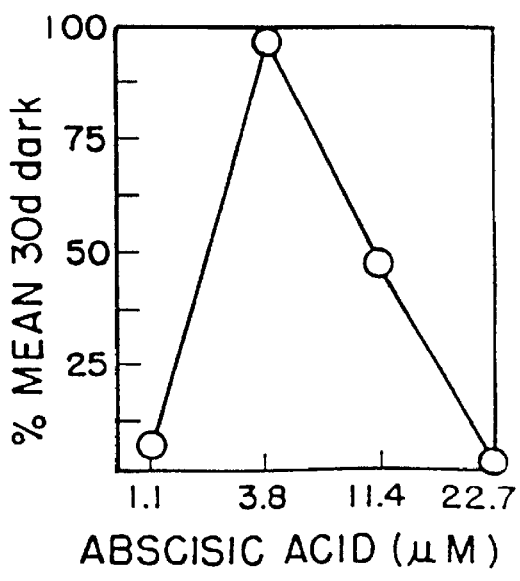

Discovery of latent adaptive plasticity in the reproductive phase of Norway spruce cell suspensions challenged by Cretaceous period climatic variables under bioreactor conditions (as seen in FIG. 19) confirms the ability of somatic cells to behave and mimic reproductive cell behavior with the asexual generation of multiple embryo-equivalents or parthenotes to ensure survival. Current invention utilizes new climatic variables and the genomic fitness of parthenotes for the new environment. The reproductive cloning process described herein serves as a new tool in biotechnology of tree improvement.

The invention described herein relates to the fact that these plants sometime in the past were subjected to different environmental conditions and had to adapt to the current conditions. The invention is based in discovery that when such prior conditions are substituted for the current conditions, a latent asexual reproduction can be revived and advantageously utilized for asexual reproduction of hybrid seeds which produce apomictic hybrid seeds. Such asexual reproduction simplifies hybrid seed production by eliminating need for isolated planting to produce F1 hybrids because fertilization, and therefore genetic cross contamination, is eliminated. Additionally, the need to maintain and increase parents of the F1 is eliminated. Such apomictic hybrid can be grown as a single line. Furthermore, obligate apomixis, having less than 1% off-type of the desired genotype, eliminates outcross contamination and minimizes the need for mechanical mixtures since fewer lines need to be handled. Finally, male sterility and fertility restoration systems are not needed to produce commercial hybrids. In this way, by utilizing this invention, the development of superior gene combinations is possible. Such superior apomicts where fertility problems are eliminated are ready for immediate performance testing and mass seed production.

In the development of this invention, studies were performed when cell from rescued early embryos in immature seeds were cultured in vitro under artificial conditions that enable experimental tests of adaptation to more or less predictable environments and the underlying mechanisms that help to ensure survival and fitness. The elite Norway spruce genotypes were selected as seeds from central Finland when the reproductive process annually occurs at temperature of about 16° C.–17° C. The current Norway spruce did not exist in the Cretaceous. Its putative ancestor living in Cretaceous conditions, is now extinct. While cool temperatures existed at north polar regions in the middle Cretaceous, it is most probable that the ancestor of Norway spruce could have been exposed to temperatures averaging 24° C.–26° C., high humidity, and at least four fold higher carbon dioxide levels. In reproducing conditions which existed in Cretaceous, the Finish Norway spruce seeds were exposed to temperatures between 24°–26°, that is to 8° C.–10° C. higher temperature than the current normal temperature for the Finish Norway spruce. Additionally, appropriate medium was used, high humidity and high levels of carbon dioxide were induced in the bioreactor. Conditions for carbon dioxide can be introduced at the start of the process. The carbon dioxide level can also build up in the flask by tight sealing the culture vessel. This is sufficient to enhance the process of diploid parthenogenesis.

These studies showed that apomictic parthenogenesis is latent and can be induced as an adaptive process in Norway spruce cell suspensions by removing four constraining variables based on comparative evolutionary considerations. In the current case, apomixis was evident as diploid parthenogenesis and the products were diploid parthenotes, that undergo cleavage polyembryony to further multiply the new generation.

A. Modelling of Adaptive Reproductive Changes

Experimental methods utilized were the origin of genotypes, their rescue, bioreactor culture, cytochemical methods and recovery of parthenotes, as described above and below. The 1.5 liter batch tank Multigen bioreactor served as an artificial ovule to which nutrients can be added and environmental parameters controlled. Cells removed from the bioreactor were fate-mapped by light microscopy and cytochemistry. Results were model-referenced to the reproductive processes known for Norway spruce, extant gymnosperms and other apomictic organisms. For the bioreactor, the process controls were inferentially model-referenced to the known physiological and heterotrophic biochemical events around the environment of the zygote. From this data, the four models have been formulated.

1. Environmentally Induced Adaptive Reproductive Plasticity

Climatic variables affect survival and the rules that determine asexual alternatives are a function of variables at the geographic seed source, as illustrated in FIG. 21. The FIG. 21 is a model with postulates for climate induced plasticity in sexual and latent asexual reproduction.

The specific combination of variables that comprises the change from sexual to asexual reproduction at the seed source have been simulated in the bioreactor. Recombinations occur spontaneously under the conditions in the artificial ovule or in bioreactor, providing a specific temperature requirement. Other factors contributing to plasticity relate to the addition of an artificially reconstituted heterotrophic nutrition to the culture medium in the bioreactor. Response to this food supply adds to the robustness and survival of asexual parthenotes when removed from the bioreactor.

2. Paths in Expressing Latent Apomictic Plasticity

A path for apomictic expressions leading to diploid parthenogenesis starts with a sporophyte and leads to various expression of apomixis resulting in diploid parthenotes or seed embryos, as seen in FIG. 20.

In most gymnosperms, this path includes variable free-nuclear stages that serve as useful cytochemical and morphological markers for the mapping of the early ontogenetic fates of cell populations. Results show that under bioreactor conditions, freely suspended cells derived from rescued early embryos behave as egg-equivalents.

Since neither fertilization nor nuclear fusion (karyogamy) occurs under the bioreactor conditions, the development of multiple free nuclei in the egg-equivalent into parthenotes that are released into the culture medium comprises the second phase of the apomictic process.

3. Continual Recycling of Apomictic Potential by Specialized Cells

Figure 22:
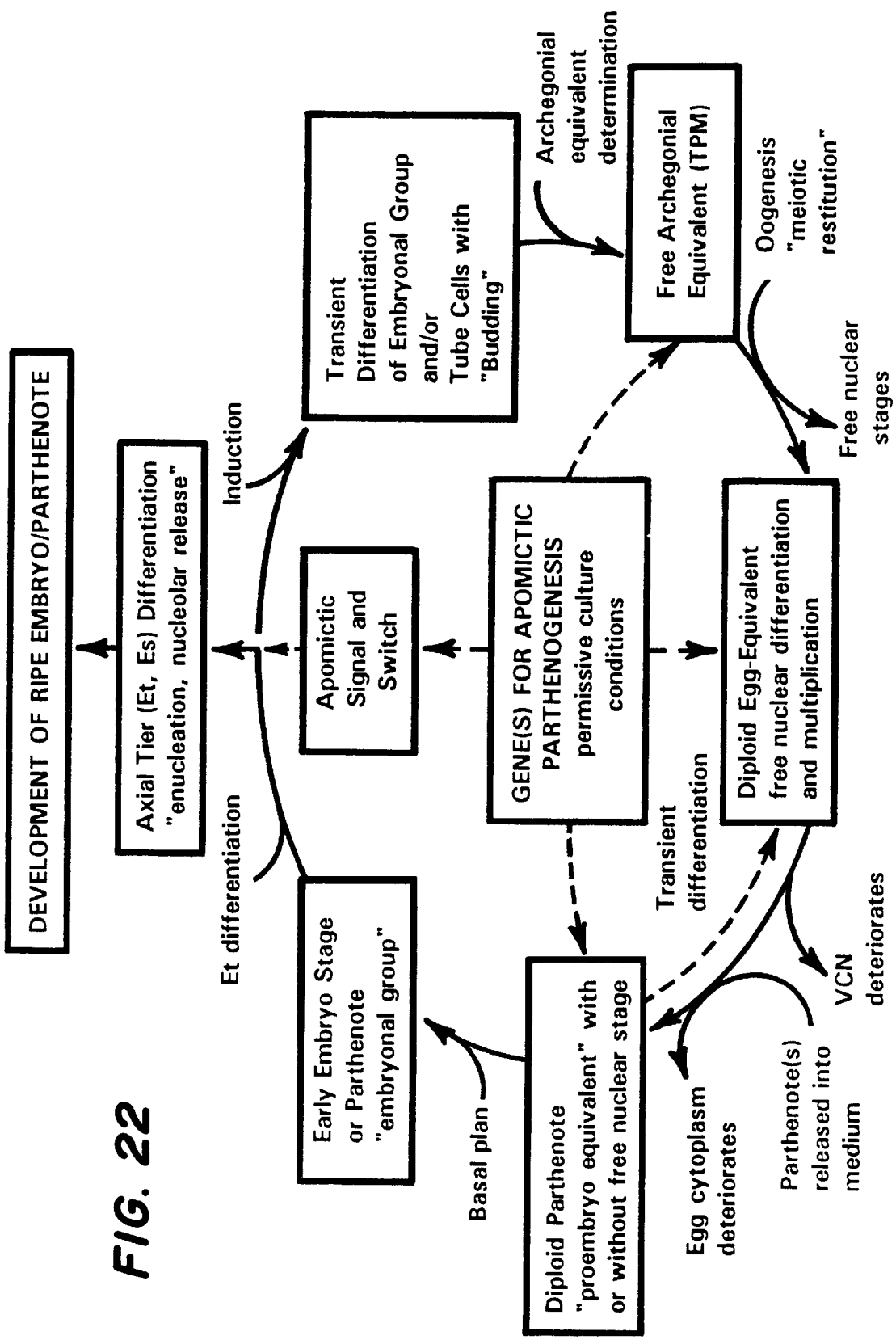
FIG. 22 is a scheme illustrating diploid parthenogenic multiplication cycle.

The expression of latent apomict genes during reproductive adaptation suggests a potential for diploid parthenogenesis, as seen in FIG. 22. Once the signal and switch to apomictic expression occurs, a sub-population of cells in the bioreactor are induced to become free archegonial initials (central cells) and then asexual egg-equivalents. This sequence leads to the formation of diploid parthenotes with a basal plan for axial tier formation.

The expression of genes for apomictic parthenogenesis is shown to affect not only the switch and signal for the process but also the formation of archegonial equivalents, diploid egg-equivalents, and diploid parthenotes.

Diploid parthenogenesis is characterized by specialized cells and markers, such as embryonal tubes, embryonal-suspensor, tubular proembryonal megakaryocyte, and ventral cell nucleus. Cells of the early embryo slough off into the culture medium and a small proportion repeats the cycle. The remaining cells develop into an embryo equivalent or parthenote after axial tier differentiation. A reversible step appears to occur at the proembryo stage. Here cells may recycle to form a more diploid egg-equivalents.

4. Adaptive Plasticity in Cells of the Early Embryo and Parthenote

Figure 23:
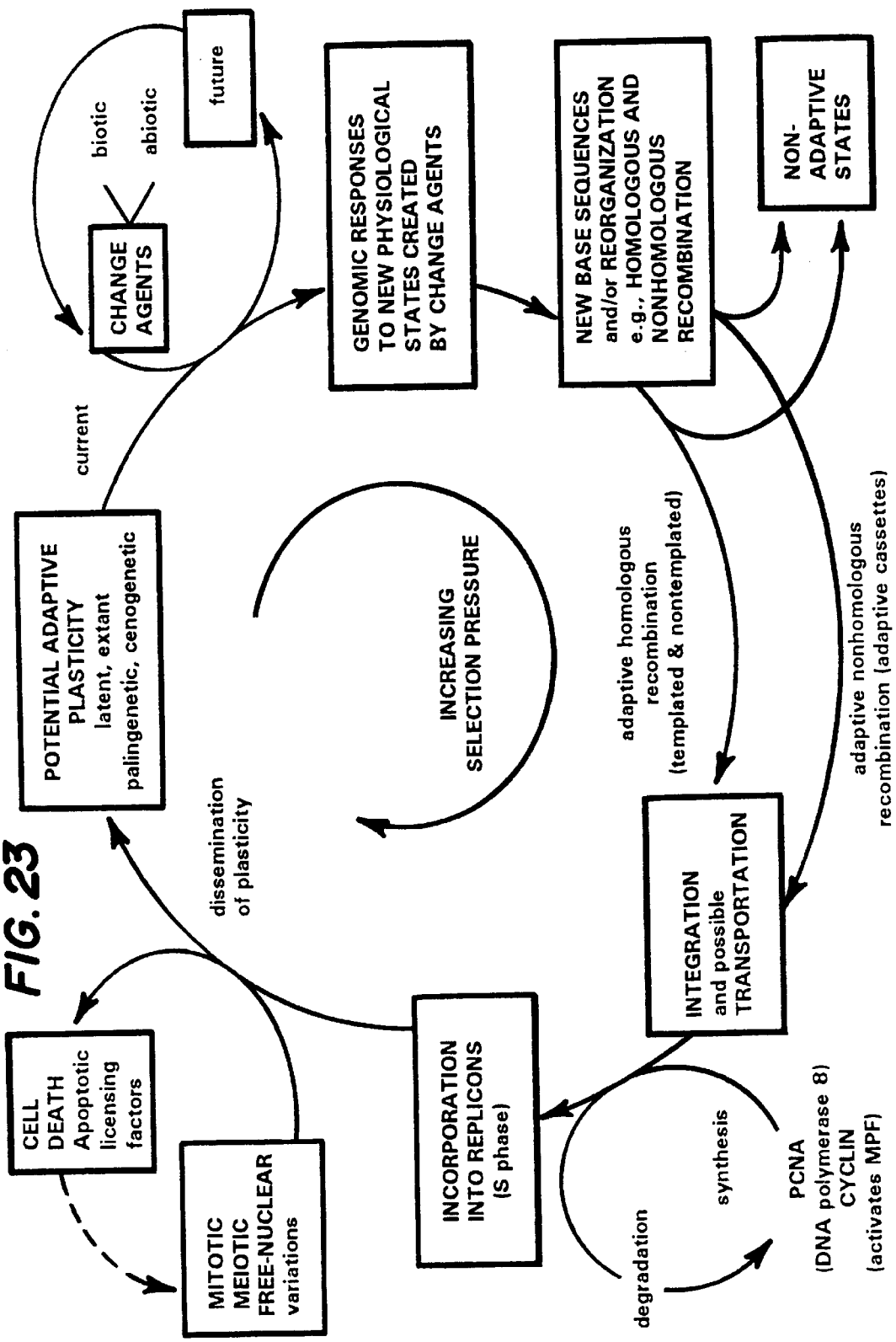
FIG. 23 shows templated or nontemplated recombination in response to increasing selective pressure as a function of climatic change agents.

While this invention comprises the clonal production of hybrid seeds, the cells enabling this process show latent and remarkable adaptive plasticity. This plasticity, as seen in FIG. 23, can lead to modifications in the expression of the ontogenetic programs with the result that the clonal products are more fit and viable under the current environmental and nutritional conditions. The outcome of the new diploid parthenogenesis is a more robust hybrid clone that has been imprinted by the culture conditions. The culture conditions, therefore, become an important determinant in enabling the preconditioning of germplasm for completing the life cycle in a wider range of field environments. The potential for expressing adaptive plasticity is a function of several change agents that elicit genomic responses leading to new physiological states. For example, an adaptive mutation or other genomic changes may occur only in the presence of selection for those changes and even in the absence of significant cell or free nuclear cycling.

III. Diploid Parthenogenesis

Diploid parthenogenesis, that is the regeneration of diploid plants asexually, which is the basis of the method of the invention, has been now discovered to exist in gymnosperms. Until this invention, such asexual means of reproduction was not known to exist in gymnosperm.

Diploid parthenogenesis which is illustrated in FIGS. 1–23, appears to start with unspecialized embryonal tube cells (free tubular proembryonal megakaryocytes) from rescued early zygotic embryos that are cultured in a bioreactor. When these cells are exposed to climatic variables simulated after the Cretaceous period and to primitive food supplies, they mimic the general ontogeny of conifer archegonial initials or central cells, eggs, and zygotes. These free cells substitute as archegonial central cells giving unreduced binucleate egg-equivalents that regenerate parthenotes (early embryos) without fertilization. In nature, replacing an egg cell that may not be capable of dividing unless it is fertilized, with another cell that can divide without fertilization, is an efficient way of introducing the capacity for parthenogenesis. The same now appears to hold true under bioreactor conditions.

Culture variables and heterotrophic nutrients imposed on cells grown in total darkness in the bioreactor are as follows: temperatures from 20° C.–30° C., preferably 23° C.–26° C., high humidity, preferably about 70% of saturation under bioreactor conditions, aeration with increased carbon dioxide to levels 2–10 times, preferably about 4 times, of those found in normal air, darkness, and a culture medium containing essential macro and micronutrients, vitamins, plant growth regulators, carbon and nitrogen sources, as described in medium section. The nitrogen sources and amino acid supplements are formulated and reconstituted based on the amino acid composition of primitive gymnosperms, that is the source is rich in amides and arginine and low in other hexone bases.

The key point is to reconstitute the nutrition given to the zygotic embryo for use by cells of the species in question.

To do this, one analyzes the composition of food supply around the zygotic embryo. This is done by chemical analysis, for example, amino acid analysis. Once the composition is defined (and there are wide variations because of mother tree nutrition, site, genotype, etc.), the concentrations and ratios of compounds are reconstituted with off-the-shelf chemicals to formulate an approximate supplemental nutritional medium. Approximate in this context means one to two figure accuracy. This formulation then becomes a component of the culture medium. Care must be taken to find the right overall concentration of the supplement, i.e., to make sure the supplement is not too strong or not too weak.

This step is one that a person skilled in the art can easily do by assaying the response of cells to the supplemented medium and finding the best overall concentration and ratios as described above. For example, an analysis of some gymnosperms shows the presence of large concentration of asparagine than glutamine in the free amino acid pool. The ratio of glutamine to asparagine, the two most dominant amino acids, can be adjusted in the supplement. One starts with the most dominant amino acids then introduces changes in their ratios to enhance the growth and development of the cells. The same process is done for sugars providing carbon source and other nutrients. The trade-off is the cost-effectiveness of how far does the practitioner need to go to obtain the cell performance that is sought as determined by fate-mapping of the cells.

In the current case, amino acid analyses of the water are obtained and alcohol soluble components are extracted from the developing seed of the genotype in question. This is then used as a model reference for the reconstitution of the supplement that is added to the culture medium. Casein hydrolysate can serve as a substitute for the above procedure, if access to chemical analyses is not available. Although the casein hydrolysate does not contain some amino acids and amides, glutamine, asparagine and other amino acids are added that make up for this deficiency. The concentrations and ratios are those found in nature and characteristic of the genotype. The ranges of concentrations and ratios of all additives can be very wide, when adapted for use as an additive to the culture medium. For example, these concentrations for glutamine and/or asparagine may be from 100 to 600 mg/l with a ratio of 2 to 1, respectively. Some genotypes can do well on glutamine alone, or arginine 100 to 400 mg/l alone, or on lysine or histidine at zero to 10 mg/l per liter of culture medium.

Until this discovery, it was believed that the absence of asexuality in the gymnosperms results from difficulties in evolving asexual reproduction. These difficulties have now been overcome under artificially controlled conditions. Specialized cells from suspension cultures of early embryos are shown to combine aposporous diploid parthenogenesis with cleavage. These latent and plastic sequential ontogenetic pathways are traced from isolated embryonal tubes that become initiated as putative central cells and produce binucleate egg-equivalents. In the absence of fertilization or fusion, egg-equivalent nuclei undergo parthenogenesis by forming a neocytoplasm and a thin cell wall. These are released as numerous diploid parthenotic leader cells into the culture medium. Parthenote development from leader cells occurs with a variable free-nuclear stage characteristic of zygotic and somatic proembryos. Parthenote development comprises a cleavage process that reconstitutes new individuals to further multiply a clonal population. The multiplication of free nuclei in egg-equivalents is stimulated by colchicine and directly contributes, through a homokaryotic advantage, to increased numbers of parthenotes and to parthenoclonal variations. The division and multiplication of free nuclei represents an early and latent form of classical cleavage polyembryony in Norway spruce and other gymnosperms.

The invention involves the initiation and recovery of transdifferentiating cells of the early embryo that express latent central cell and binucleate egg-equivalent behaviors leading to diploid parthenogenesis. These processes enable the cloning of parthenotes, that is, embryo-equivalents, from egg-equivalents and without fertilization. Diploid parthenogenesis creates opportunities to develop new, more flexible breeding strategies.

Diploid parthenogenesis results in cleavage polyembryony, that is in the subdivision of a single embryo into a group of competing embryos. Cleavage polyembryony greatly increases the probability that an ovule has at least one surviving embryo. In cell suspensions from rescued early embryos of Norway spruce, during parthenote multiplication, it was observed that the parthenotes continue to multiply by the classical cleavage process. This continuation of parthenotes represents a monoparthenotic cleavage process, yielding multiple parthenotes analogous to monozygotic cleavage polyembryony.

As described in the Background of the Invention, activation of the latent apomictic behavior requires four conditions (constraints) that must be met before there is transitions from sexual reproduction to diploid parthenogenesis in asexual heterosporous plants.

First, there must be the capacity for parthenogenesis.

Second, such capacity must be expressed by preventing the fertilization of eggs or egg-equivalents.

Third, eggs must exhibit the same ploidy level as the mother so that meiotic reduction can be avoided.

Fourth, all of these conditions must be met simultaneously or almost simultaneously so that the deleterious effect of each of these conditions which appears in the absence of the other conditions is avoided.

The invention is based on three basic findings.

First finding confirms that the removal of the four constraints cited above restore parthenogenic apomixis. Second finding is that colchicine simplifies parthenogenesis through perturbations in free nuclear stages of oogenesis and proembryogenesis of egg-equivalents. Third finding is that other latent variations in apomictic expression exist under artificial culture conditions.

During determination whether or not the removal of four constraints restore parthenogenetic apomixis, the cytological examination of individual cells and mapping of their fates, amplification of diploid parthenogenesis of colchicine, and variation in free-nuclear expression studies were performed.

1. Fate-Mapping of Cell Types

Cytological examination of individual cells and their facets in fractionated cell suspension cultures in multiwell plates according to Example 2 revealed a wide range of types and behaviors of cells that are summarized in FIG. 1.

Figure 3:
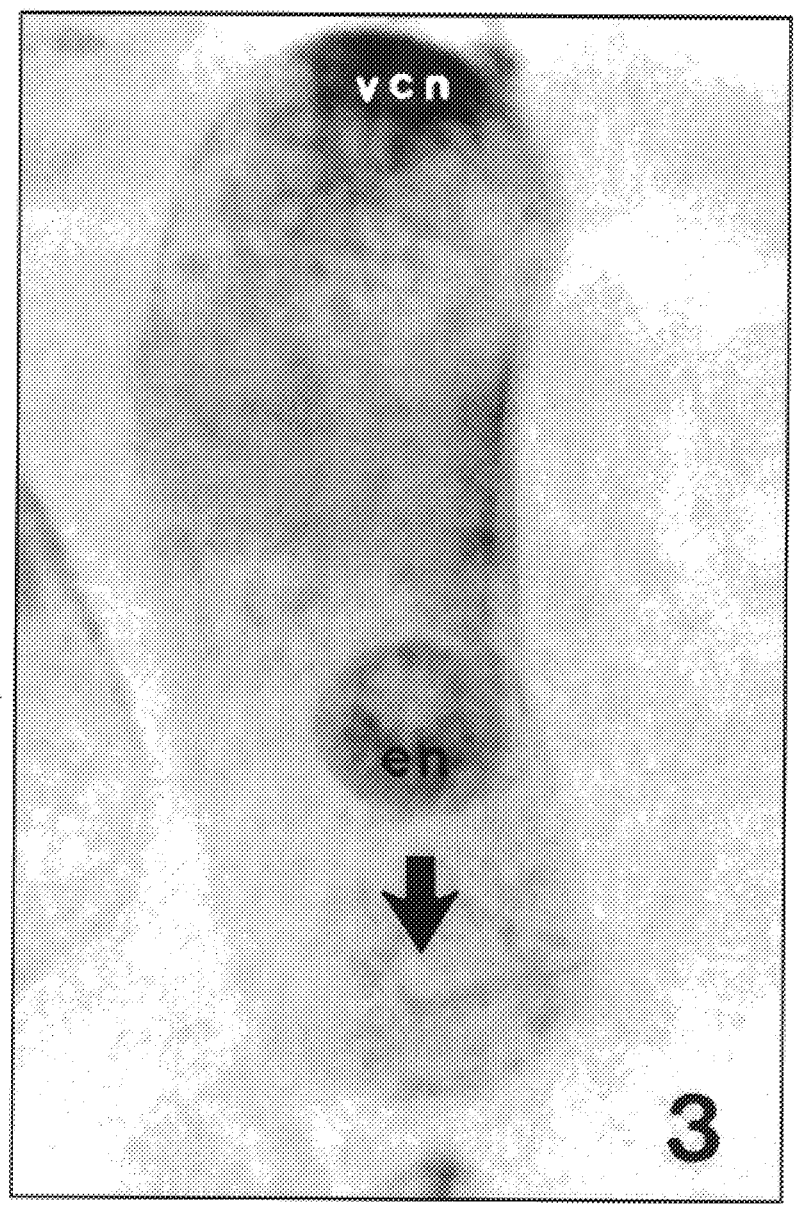
FIG. 3 shows the altered isolated cells from the embryonal tube region of the axial tier of early embryos. The cell is an egg-equivalent with a ventral canal nucleus and egg nucleus.

FIG. 1 is a scheme of variations in the expression of diploid parthenogenesis in cell suspensions of *Picea abies*. FIG. 1A shows that both spruce egg-initial and tubular megakaryocytes putative archegonial central cells derived from isolated embryonal tubes contain a large nucleus which divides to produce a binucleate cell (FIG. 1B). The spruce egg contains an egg nucleus and a ventral canal nucleus that eventually disintegrates. The egg-equivalent nucleus (en) and the ventral canal nucleus (vcn) obtained from putative central cells mimic the behaviors of their counterparts in archegonia, as seen in FIG. 3. Without fertilization, the (en)

migrates to an opposite pole (FIG. 1C). During migration, a neocytoplasm forms around the (en). In the egg-equivalent, the (en), now with its neocytoplasm, forms a thin cell. The walled nucleus is released from the egg-equivalent cytoplasm (FIG. 1D), as further seen in FIG. 6, as a parthenote leader cell ($pE_L$) (FIG. 1E). After the release, the egg-equivalent starts to deteriorate, producing and releasing mucilage into the culture medium. Four ontogenic variations arise. First, in the proembryo and parthenote, a free-nuclear stage occurs in advance of axial tier differentiation as illustrated in FIG. 1 as arrow 1. Second, the cells divide to restore new embryonal tubes in close proximity to deteriorating egg-equivalents without a free-nuclear stage (arrow 2, FIG. 1G). Third, thin-walled $pE_L$ cells are released into the culture medium (arrow 3, FIG. 1F). A new axial tier may be restored with the formation of new embryonal tubes (arrow 5, FIG. 1) before restoring an axial tier (arrow 6, FIG. 1G). Fourth, the binucleate stage in egg-equivalents may continue nuclear cycling to produce coenocytes (FIG. 1H), details seen in FIG. 5, before the release of parthenote leader cells (FIG. 1H, arrow 7).

Figure 2:
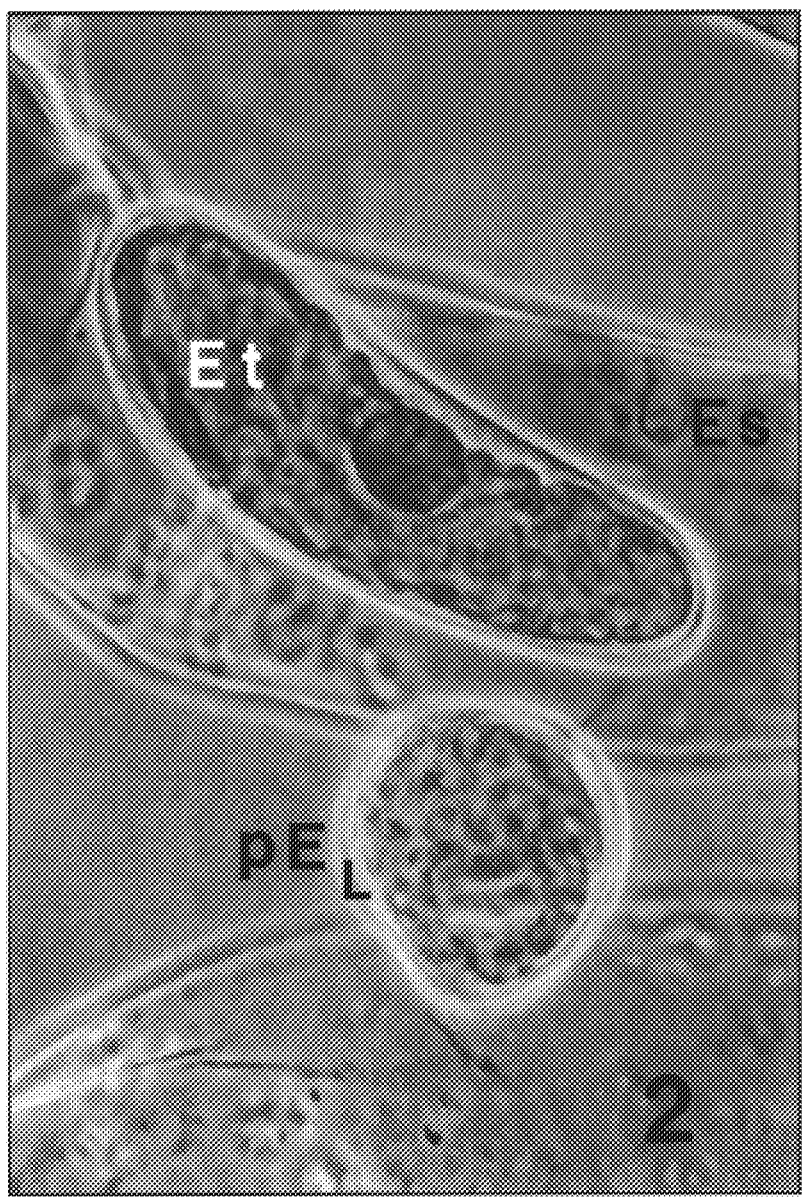
FIG. 2 shows three main individual cell types recovered after density gradient separation aimed at sorting out cells having the capacity for diploid parthenogenesis.

FIG. 2 shows three main individual cell types recovered after density gradient separation of early embryos in suspension culture. Parthenote leader cells $pE_L$, having 15–20 $\mu$M diameter, reconstitute parthenotes with their axial tier. Free embryonal tube cells (tubular megakaryocytes [ET] approximately 80 to 120, sometimes up to 280 $\mu$M in length), pass through binucleate egg-equivalent and multinucleate stages. Large enucleated embryonal-suspensors (Es) are longer than 280 $\mu$M. These cells originate by axial tier differentiation in the early embryo.

The expression of the diploid parthenogenesis behavior and the establishment of diploid parthenogenesis required the isolation of a uniform population of individual embryonal tubes (Et) from cell suspension cultures of rescued early embryos. These Et cells had the appearance of tubular megakaryocytes and were recovered as a light fraction by collecting these cells from the Ficoll density gradient. In the suspensions, Et cells were released from early embryos into the culture medium. When isolated, these cells transdifferentiated into archegonial central cells to produce binucleate egg-equivalents as seen in FIG. 3.

FIG. 3 shows isolated cells from the embryonal tube region of the axial tier of early embryos which become altered to express a sequence of phenotypes. These are initially arbitrarily designated as a tubular proembryonal megakarycytes and later as putative central cells. The large nucleus having approximately 10 $\mu$M diameter in the central cell divided to produce two nuclei. One nuclei was equivalent to the egg nucleus (en) and the other to a ventral canal nucleus (vcn), as seen in FIG. 1. This process is characteristics of normal oogenesis in Norway spruce. The (vcn) may disintegrate at one pole while the (en) may migrate to the other pole and continue to divide. Cells are stained with Feulgen-Giemsa.

Egg-equivalents seen in FIG. 3 developed similarly to their zygotic proembryonal counterparts. The early stages showed considerable plasticity in nuclear cycling as seen in FIGS. 4–6.

Figure 4:
FIG. 4 shows a photograph of the Feulgen-Giemsa cytochemical staining showing the migration and division of the egg with the formation of new cytoplasm around each nucleus.

FIG. 4 shows the migration and division of the (en) with the formation of new cytoplasm around each nucleus which mimics zygotic behaviors. Cells are stained with Feulgen-Giemsa.

FIG. 5 shows that in some cases, up to 8 nuclei (arrows) may be formed within central cells and their egg-equivalents. Cells are stained with acetocarmine.

An 8-nucleate stage was found at a frequency of <0.1% in cell populations harvested between 10 am to 12 noon (FIG. 5). In Norway spruce, egg-equivalents originated from diploid cells in early embryos, predominantly from the tier of Et. FIG. 6 shows a nucleus with a new cytoplasm and cell wall (open arrow) released as a $pE_L$ within the cell (solid arrow), behaving as a fertilized egg. The (vcn) remains within the cytoplasm of the egg-equivalent. The structures were double stained with acetocarmine and Evan's blue.

When Et cells were released from the axial tier into the culture medium, many adopted a phenotype of what were initially identified as tubular proembryonal megakaryocytes (TPMs) because these cells differentiated into epoembryo-like structures. Observations from this study indicated that TPMs behaved as central cells, yielding binucleate egg-equivalents that expressed diploid parthenogenesis. Wall enclosure of free nuclei in binucleate egg-equivalents was followed by release from the egg-equivalent cytoplasm of parthenote leader ($pE_L$) cells (FIGS. 6 and 7).

Figure 7:
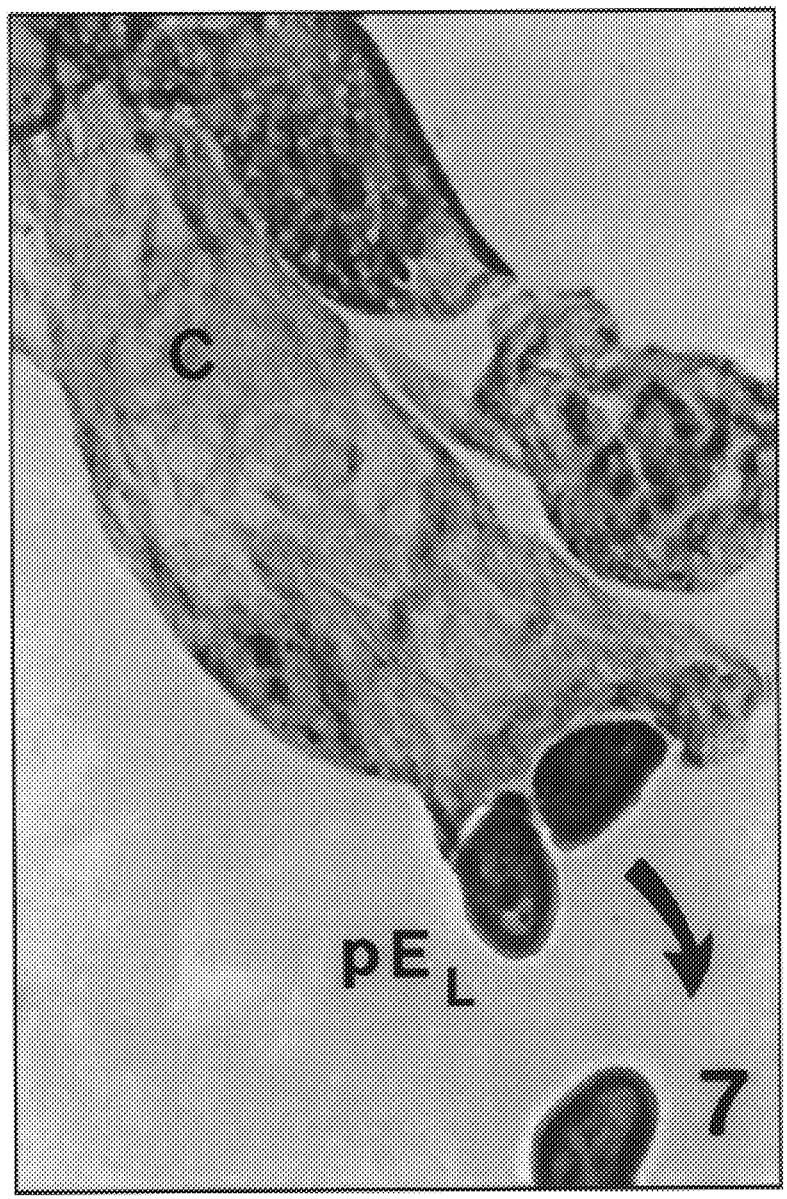
FIG. 7 shows release of individual $pE_L$ cells formed from the nuclei.

FIG. 7 shows individual $pE_L$ cells formed from free nuclei released (arrow) into the culture medium from the cytoplasm (c) of an egg-equivalent. Double-staining with silver nitrate and Giemsa highlights the nucleoli of released $pE_L$ cells. The release of $pE_L$ cells is a unique method of reconstituting parthenotes, equivalent to early embryos, without cleavage.

Egg-equivalents substituted as unreduced eggs by sequentially regenerating $pE_L$ and parthenotes without fertilization (FIG. 7). The mimicked and substituted features were: (1) Hundred micrometers in length the egg-like shape of cells having a large, dense egg-like nucleus. The latter divided to give a binucleate cell. (2) The two nuclei behaved individually much like the egg nucleus and the ventral canal nucleus (vcn); the latter sometimes disintegrated. A wall did not develop around the (vcn) as in some other conifers. Vcn and egg-equivalent nuclei often showed a differential double-staining with acetocarmine and Evan's blue with the vcn being more permeable to the Evan's blue. (3) The formation, without fertilization, of multiple, free nuclei from the egg-like nucleus, and the basal migration of free nuclei that became surrounded first by a neocytoplasm and then a cell wall to yield $pE_L$ cells. In nearly all gymnosperms, the immediate response to the stimulus of fertilization is a characteristic rapid series of free nuclear divisions. In the current cells, neither fertilization nor nuclear fusion occurred even with colchicine. (4) Parthenote formation occurred from $pE_L$ cells within the cytoplasm of the egg-equivalent or by release of $pE_L$ cells into the culture medium as seen in FIGS. 1 and 8–15. The development of parthenotes comprised a variable free nuclear stage (FIG. 11). The free nuclei in a cell at this stage is variable but with enhanced food supply, for example casein hydrolysate and glutamine in the medium, numbers of nuclei can exceed 32 especially in Norway spruce and Araucaria. In pines, the proembryonal stage does not usually have more than 4 free nuclei before cellularization begins to restore the axial tier of the early embryo.

Figure 8:
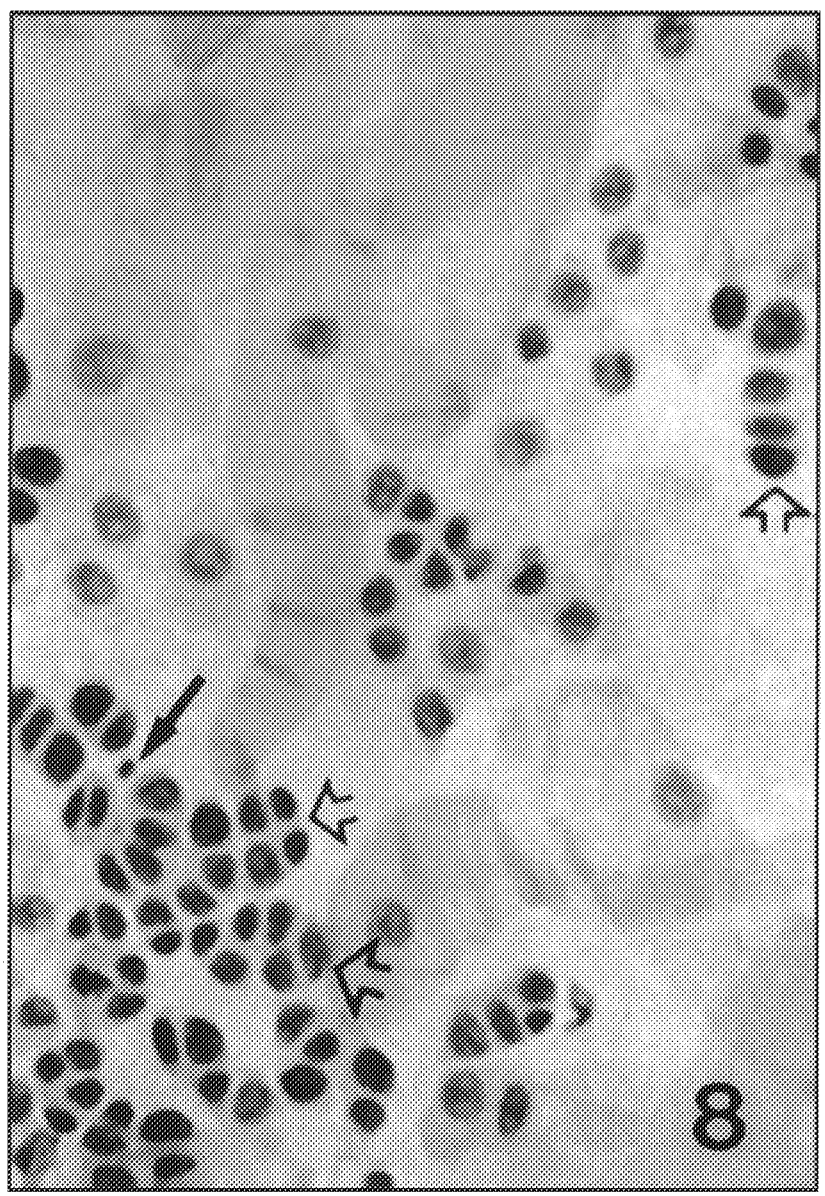
FIG. 8 shows a field of parthenotes and tubular megakaryocytes.

FIG. 8 shows a field parthenotes and tubular megakaryocytes. The parthenotes develop by restoring the axial tier typical of the early embryo (open arrows). Occasionally a micronucleus having approximately 2–3 $\mu$M diameter is found in parthenotes (solid arrow). Cells are stained with Feulgen-Giemsa.

Fate-mapping of cell types showed that the removal of constraints restored the expression of parthenogenic apomixis which confirmed that the capacity for parthenogenesis, albeit undiscovered until now, is inherent and latent in at least two genotypes of Norway spruce (*Picea abies* L. [Karst.]). Under the controlled conditions, fertilization nuclear fusions were avoided and diploid parthenogenesis proceeded.

Specialized individual cells (TPMs) mimic, through alterations in nuclear size and free nuclear stages, both oogenesis and proembryony without fertilization, i.e., they behave as archegonial cells to produce binucleate egg-equivalents. All conditions for diploid parthenogenesis as shown in FIGS. 1 and 20 when coupled with four criteria required for diploid parthenogenesis, were met simultaneously in liter nippled flasks and in a bioreactor having abundant organic and mineral nutrients under the specified levels of plant growth regulators (PRG). Together, these processes lead to parthenotes bearing the same ploidy levels as donors (mother) cells from the early embryo.

Several criteria, based on cytochemical staining and fate-mapping, support the view that TPMs are equivalent in behavior to central cells. Attributes of central cells found in populations of TPMs were: (1) enlarged cell with an elongated shape that continued to the egg or egg-equivalent; (2) highly vacuolate cytoplasm; (3) nucleus divided to form an egg nucleus or cell with or without a ventral canal nucleus; (4) egg nucleus enlarged considerably during cell maturation; and (5) deposition of material occurred on the plasma membrane. Taken together, central cell behavior and free nuclear stages initiated from TPMs mimicked the natural ontogeny of the Norway spruce egg, as described in *Med. Fran Statents Skoforsk,* supra.

The occurrence of multiple nuclei in cells warrants further consideration. The eight-nucleate stage is common in megasporogenesis, in the proembryony of Gnetum and Ephedra. The eight free nuclei of pine proembryony organize with walls only at the bottom of the egg, while in Ephedra they organize with walls before reaching the bottom. In the current case, thin-walled nuclei with neocytoplasm were released as $pE_L$ into the culture medium. No evidence was seen of free nuclei released in the medium. This shows that only walled cells are released, that is that only nuclei have the capacity to form cell walls that comprise parthenotes. Presence of free nuclei in the medium would indicate that cells are ruptured and their contents are spilled.

2. Amplification of Diploid Parthenogenesis by Colchicine

The second step of the investigation was determination whether colchicine would amplify diploid parthenogenesis under the conditions described above. When cell suspensions were exposed to a range of colchicine concentrations from $5 \times 10^{-3}$ to $5 \times 10^{-6}$ M, the number of free nuclei in binucleate egg-equivalents multiplied considerably as seen in FIG. 9.

Figure 9:
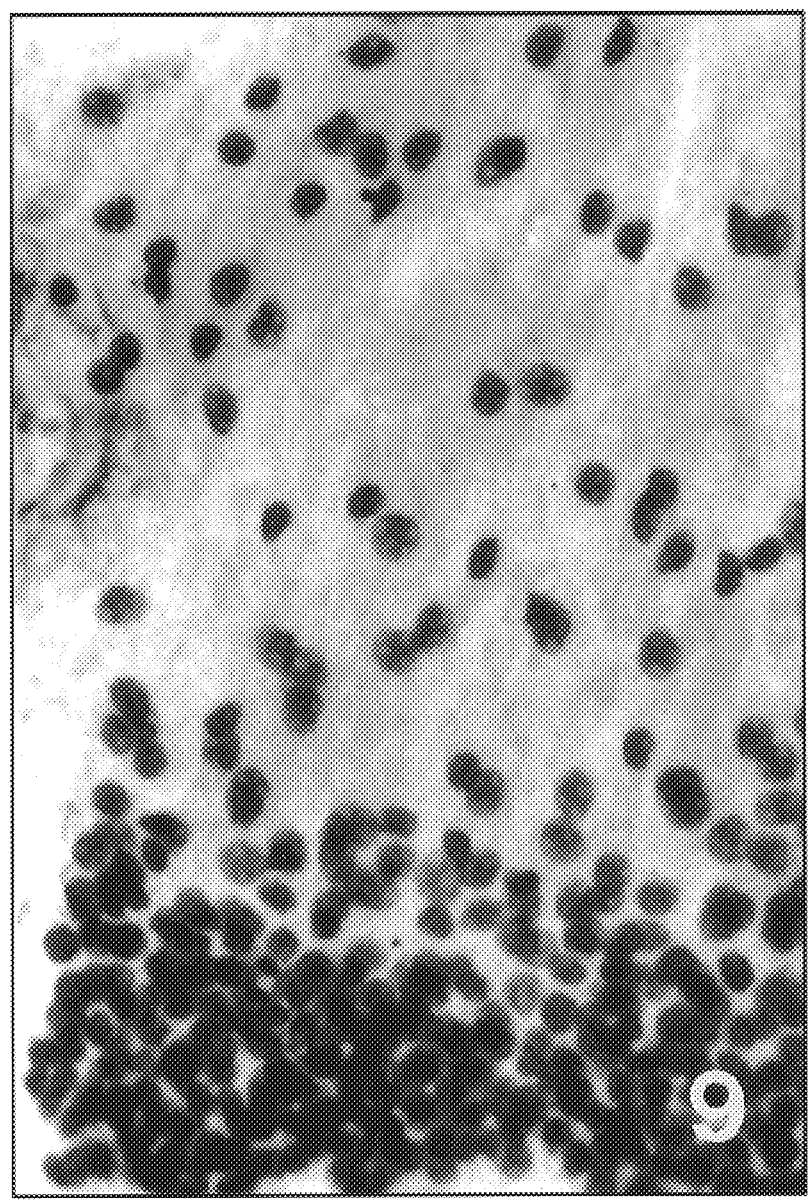
FIG. 9 shows parthenogenesis modified with addition of colchicine.
Figure 10:
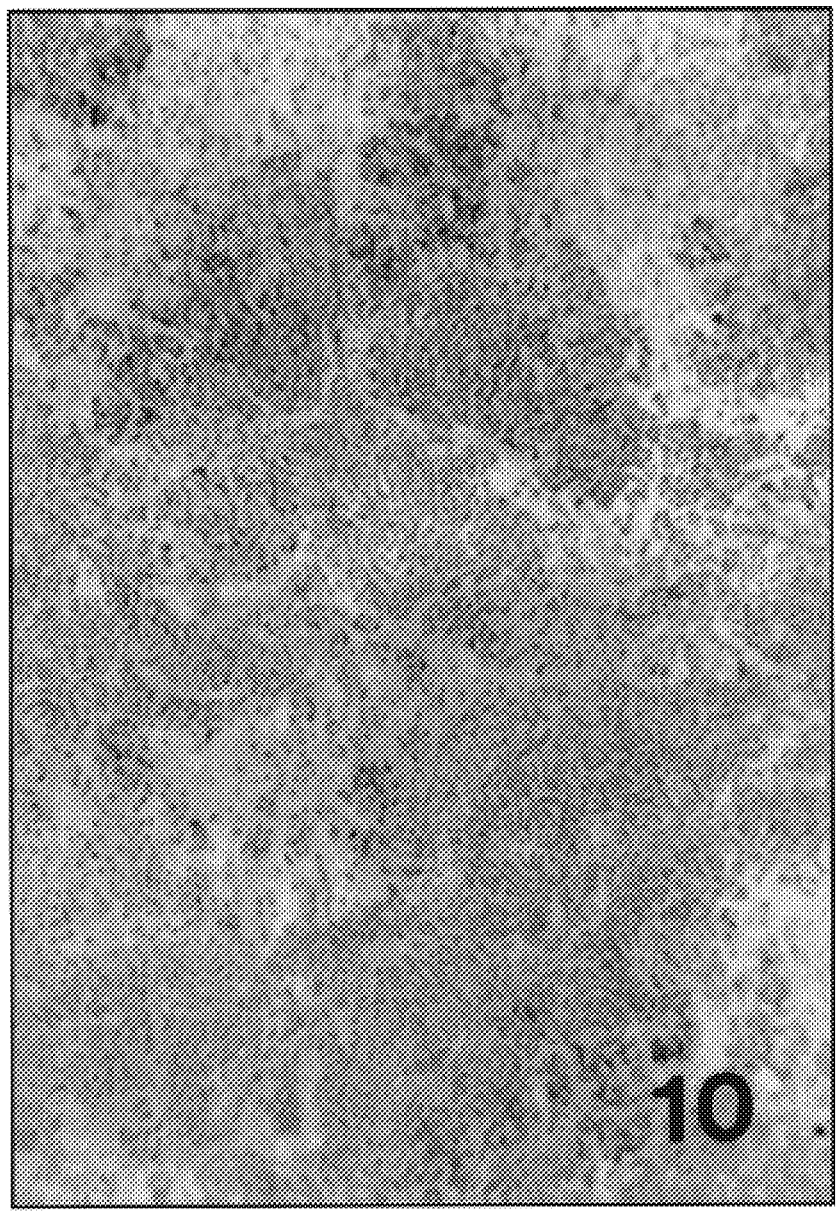
FIG. 10 shows a multiple release of free-$pE_L$ into medium under the influence of colchicine.
Figure 11A:
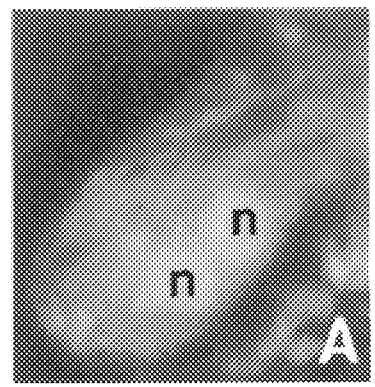
FIG. 11 illustrates free-nuclear behavior in an egg-equivalent and in parthenotes.
Figure 11B:
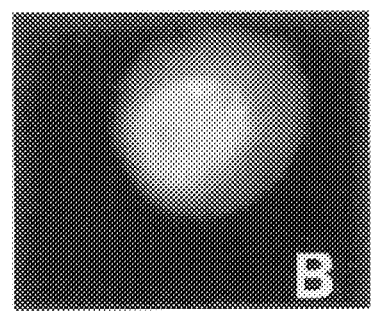
Figure 11C:
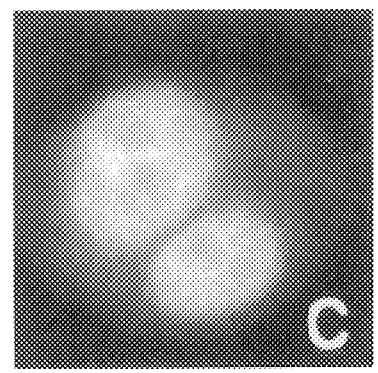
Figure 11D:
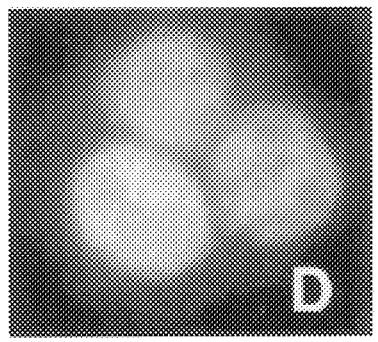
Figure 11E:
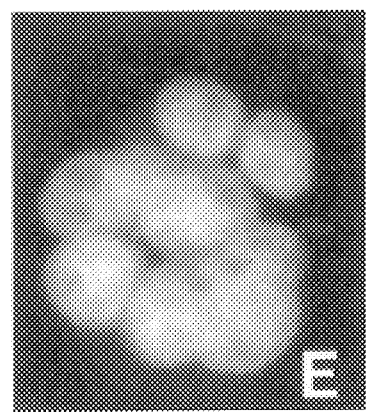
Figure 11F:

FIG. 9 illustrates enhancement of diploid parthenogenesis with colchicine ($5 \times 10^{-3}$ to $10^{-4}$ M), free nuclei (8 to 10 $\mu$M diameter) replicate and pile up at the ends of egg-equivalents undergoing parthenogenesis before being released into the culture medium as $pE_L$ to yield parthenotes. Cultures were stained with Feulgen-Giemsa. FIG. 10 shows thousands of free-$pE_L$ having 10–15 $\mu$M diameter, released simultaneously into the culture medium under the influence of colchicine. Feulgen-Giemsa staining colchicine at $2.5 \times 10^{-4}$M added to the culture medium without plant growth regulators increased the final dry mass by 45±15% over controls and 35% over medium with 2, 4-D and ABA.

Factors studied to optimize parthenogenesis included the effects of plant growth regulators, temperature and colchicine. The results are shown in Table 1. The same conditions were used for the bioreactor scale-up of cell suspensions. Temperatures selected were 14°, 12° and 25°±2° C., with the lowest representing a rough estimate of the mean global temperature or the earth in the Mesozoic and the highest tropical mean annual temperature in the Cretaceous. Factors involved in the recovery of parthenotes have been repeated at least 6 times over a 4-year period.

TABLE 1

Yield of Parthenotes of Norway Spruce

| TREATMENT | CONDITIONS | PERCENT | MG/DRY/WT |
|---|---|---|---|
| Control |  | 100 | 317 |
| PGR | 24–36° C. | 110 | 347 |
|  | 13–15° C. | 60 | 189 |
| Colchicine |  | 145 | 468 |
| ABA |  | 110 | 346 |

Control contained no PGRs/0.5 LP medium
PGR contained BAP 1 mg/l, and 2,4-D 2mg/l
PGRs-plant growth regulators
BAP-$N^6$-benzyladenine
ABA-abscisic acid
Variance around mean values does not exceed ±15%.

Table 1 illustrates yield of early embryos, parthenotes of Norway spruce after one week of subculture.

Most of this dry mass increase was attributed to a chain reaction leading to the multiplication of free nuclear genomes. After formation of a thin layer of neocytoplasm and a cell wall, free nuclei were released as $pE_L$ into the culture medium as seen in FIGS. 7, 8, and 10. Higher concentrations of colchicine were toxic. Numerous cytogenetic aberrations such as micronuclei (FIG. 8) isolated chromosomes, lagging chromosomes in mitosis, and polyploidy were seen.

FIG. 11 shows free-nuclear behavior in an egg-equivalent and in parthenotes, as revealed by diamidinophenylindole (DAPI) fluorescence. FIG. 11A shows binucleate state in an egg-equivalent (n means nucleus). FIG. 11B shows single nucleus having approximately 8 $\mu$M diameter in parthenote. FIGS. 11C to 11E show binucleate, trinucleate and decanucleate stages of nuclear cycling parthenotes before axial tier formation. These stages mimic the free-nuclear stage of the proembryo in Norway spruce seeds. FIG. 11F shows multinucleate parthenote having approximately 20–25 $\mu$M diameter, as new cell walls form, signalling the start of axial tier differentiation.

In all cultures without colchicine, parthenotes restored an axial tier of cells within 1–2 days. Restoration was accompanied by the restitution of new individuals by cleavage in the embryonal group of cells. Cleavage resulted in filamentous ramets of early embryos having elongated suspensors. This mass of parthenotes, seen in FIGS. 12–14, is equivalent to an embryonal-suspensor mass that is normally recovered from rescued early embryos of Norway spruce.

Figure 12:
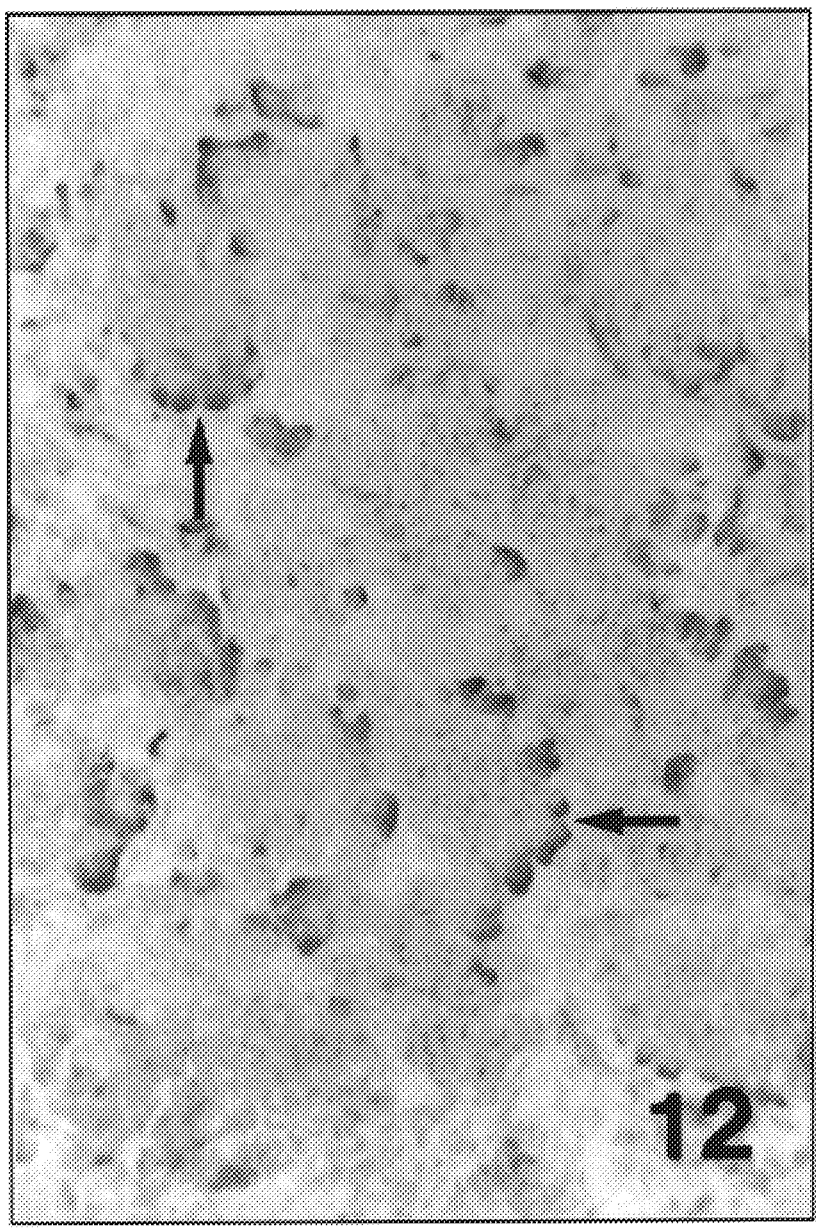
FIG. 12 illustrates axial tier formation and parthenote multiplication accompanied by a cleavage process.

FIG. 12 illustrates that once the proembryonal stage is reached by the parthenotes, axial tier formation begins and further parthenote is accompanied by a cleavage process (arrows). Cells are stained by Feulgen-Giemsa. (Arrow length ca 100 $\mu$M).

Figure 13:
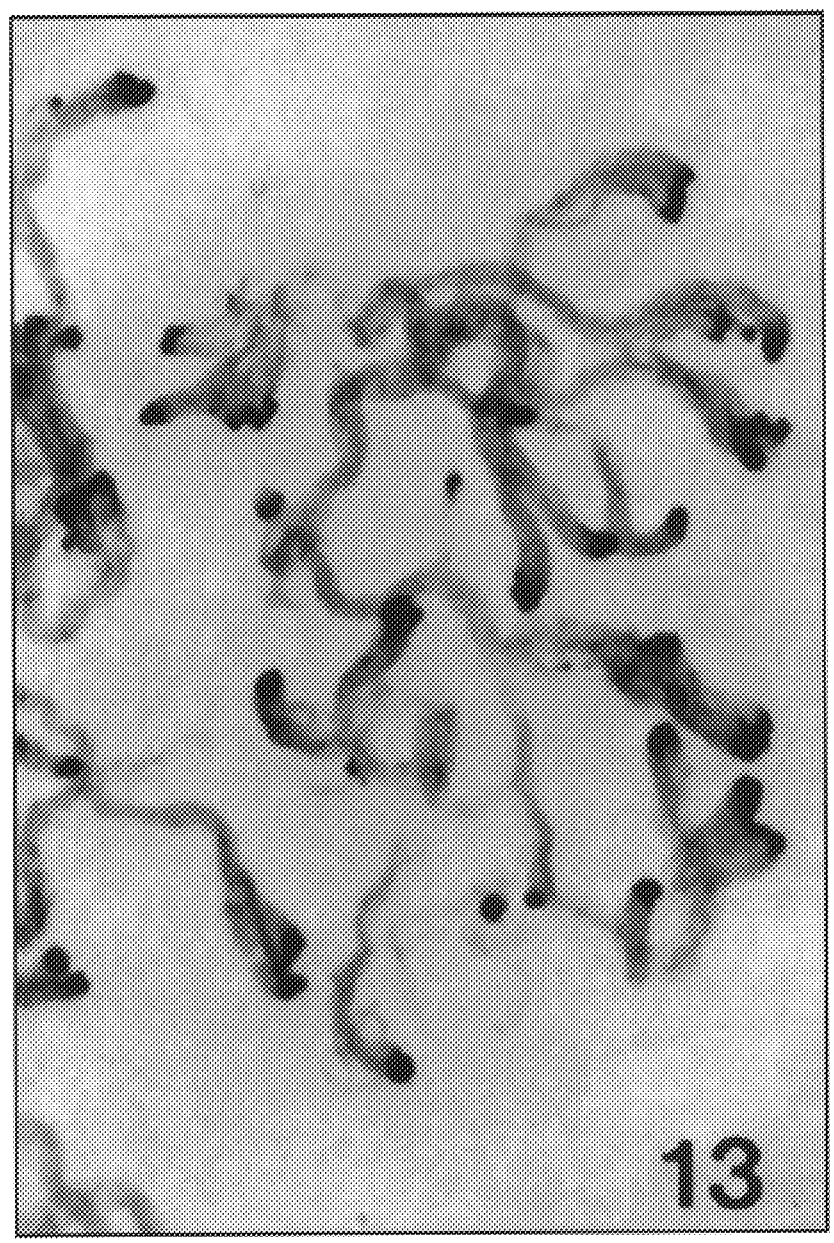
FIG. 13 shows advanced stage of early embryo (parthenote) formation.

FIG. 13 shows advanced stage of early embryo formation (parthenotes) which indicates the development and elongation of suspensors up to 800 $\mu$M long. Cleavage group of early embryos yields a fractal pattern that forms a fabric of clones (ramets) without any evidence of callus formation. The embryonal group of cells is stained red with acetocarmine, the elongated suspensor cells take up Evan's blue. This embryonal-suspensor mass winds around the propeller of a bioreactor.

Figure 14:
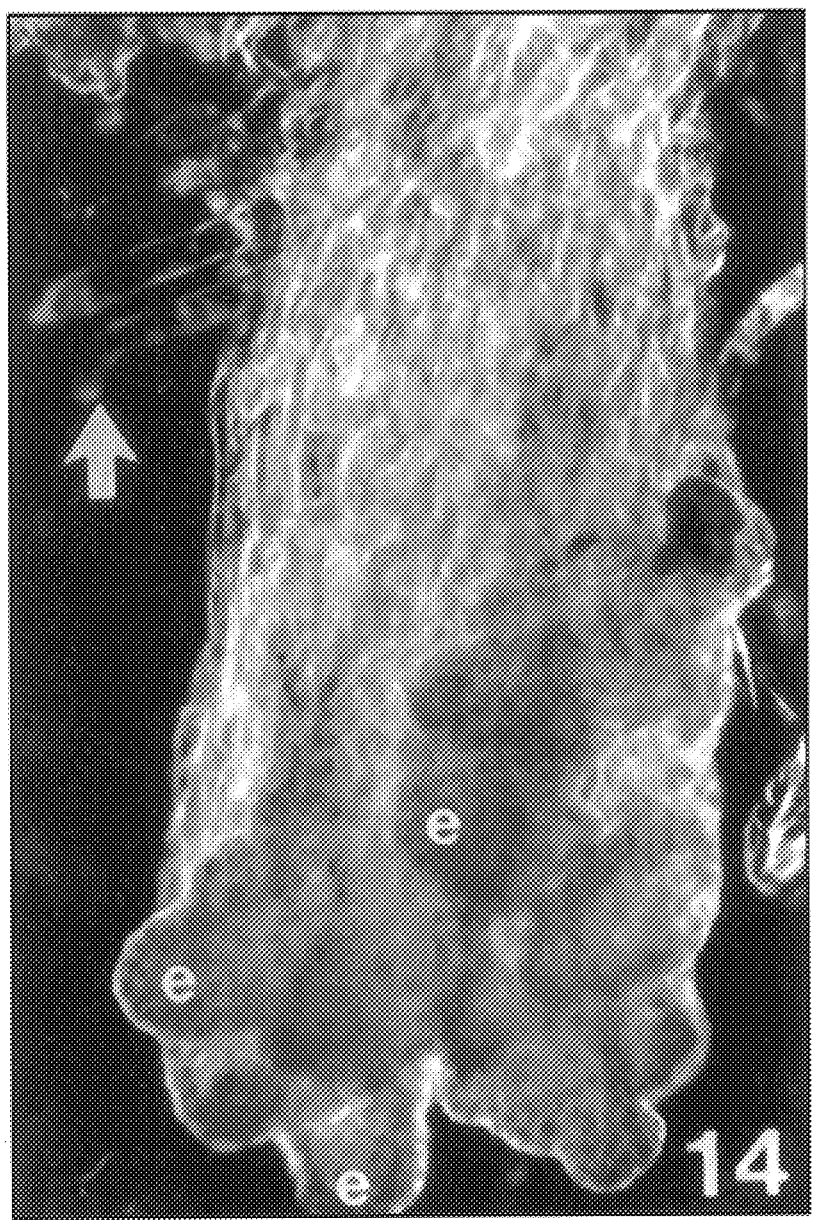
FIG. 14 shows multiple cleavage of parthenotes.

FIG. 14 shows multiple cleavage in a ramet of early embryos (parthenotes). The embryonal group (e) approximately 20–30 $\mu$M long, is stained with acetocarmine. Arrow points to tubular cells leaving the cleaving mass. These cells either become enucleated (Es cells) or become free megakaryocytes, as seen also in FIG. 2.

In cultures treated with short exposures (1 to 3 days) of high levels of colchicine, the release of $pE_L$ and the restoration of the axial tier became aberrant as seen in FIGS. 15–18.

Figure 15:
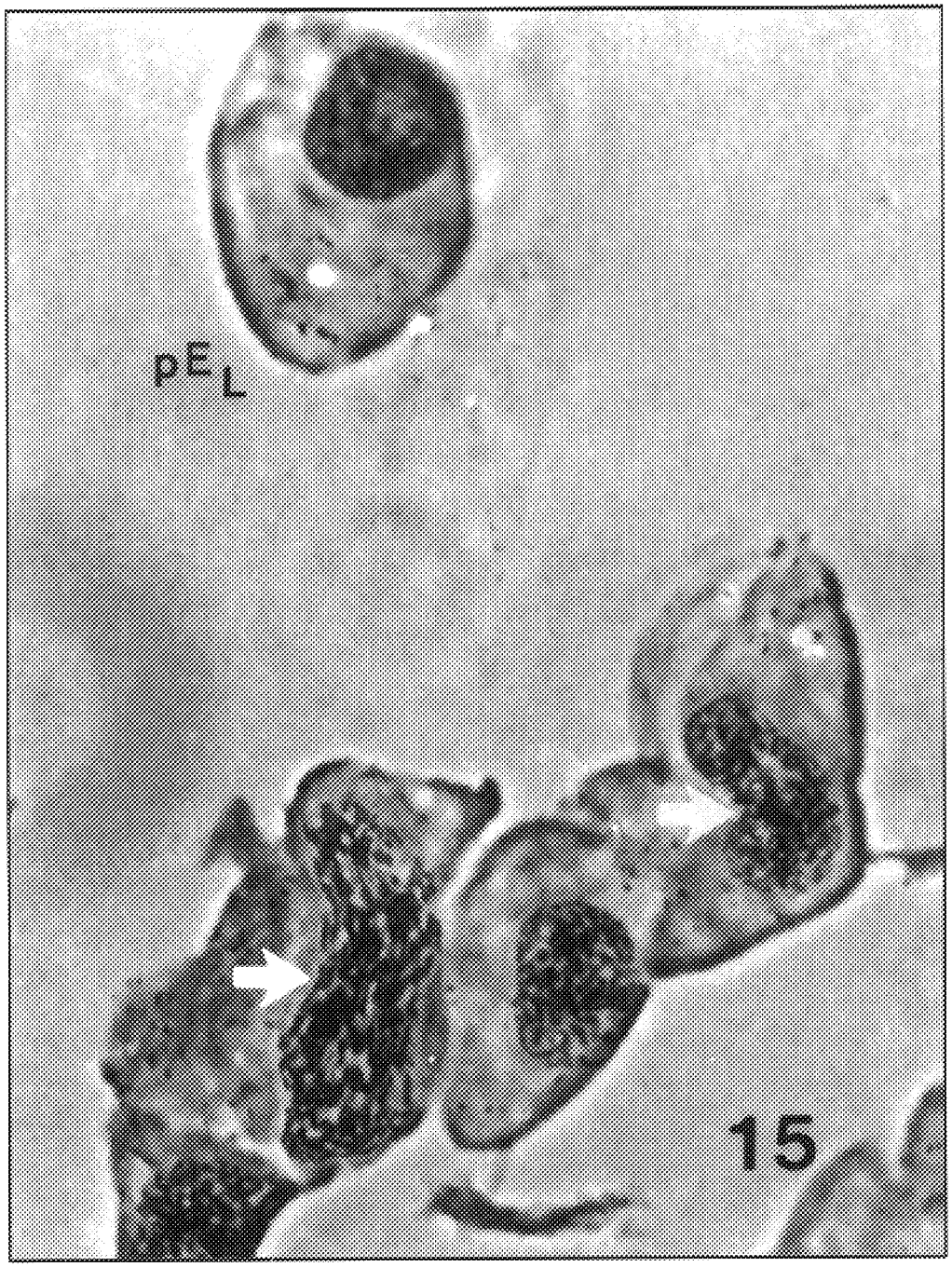
FIG. 15 shows division of $pE_L$ cells by an amitotic process.

FIG. 15 shows $pE_L$ cells having approximately 10–15 $\mu$M diameter which divide (<1%) by an amitotic process (arrows). Feulgen-Giemsa staining.

Figure 16:
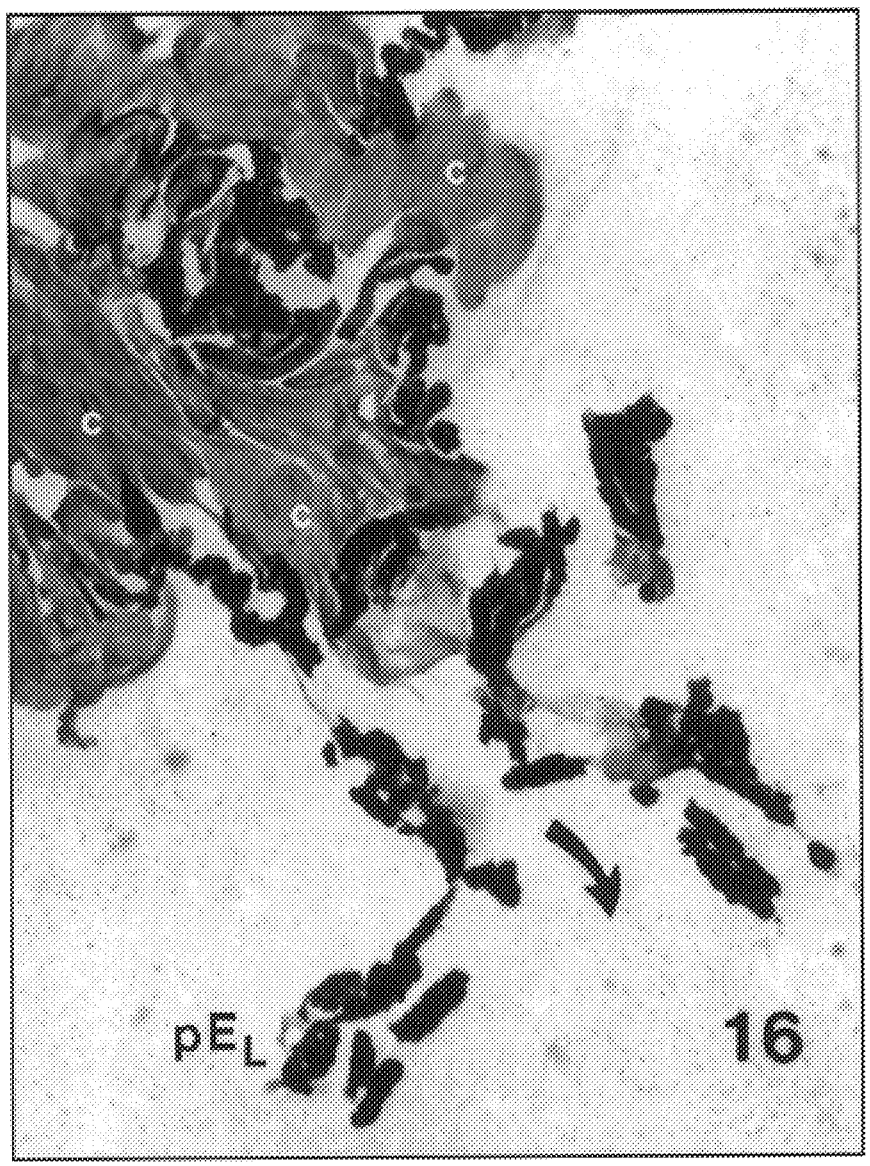
FIG. 16 shows a release of abortive compressed and elongated $pE_L$ cells from the cytoplasm into the culture medium.

FIG. 16 illustrates that when amitosis was evident, the $pE_L$ cells, now heavily stained, compressed and elongated and became abortive when released from the cytoplasm (c) into the medium. Silver-Giemsa staining.

Figure 17:
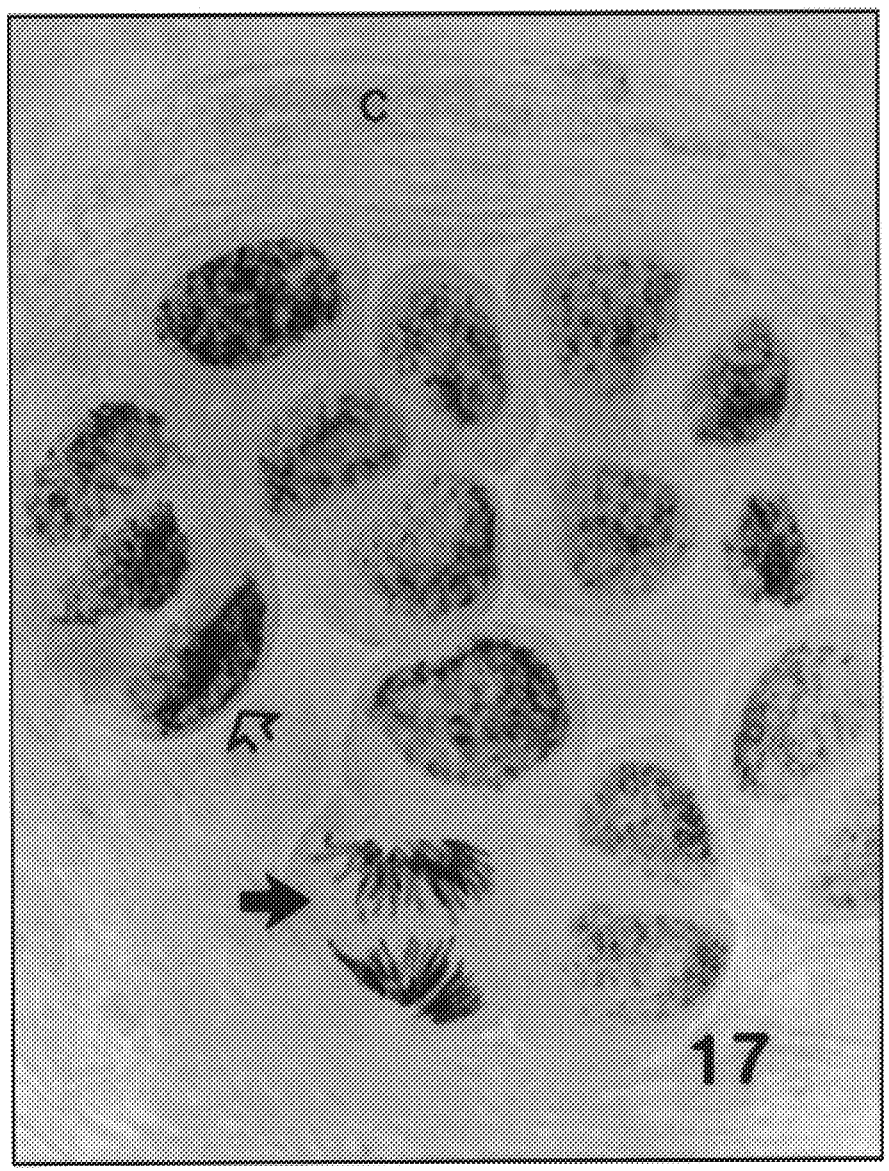
FIG. 17 shows normal mitosis in diploid $pE_L$ cells.

FIG. 17 shows normal mitosis in diploid $pE_L$ cells (arrow). This indicates that parthenotes have the same ploidy as the mother source of cells. Released $pE_L$ cells and parthenotes are surrounded by remnants of a now highly elongated and spent egg-equivalent having undergone diploid parthenogenesis. Cytoplasm (c) was stained with Feulgen. New axial tier restoration (3 cells) in parthenote started (open arrow).

Figure 18:
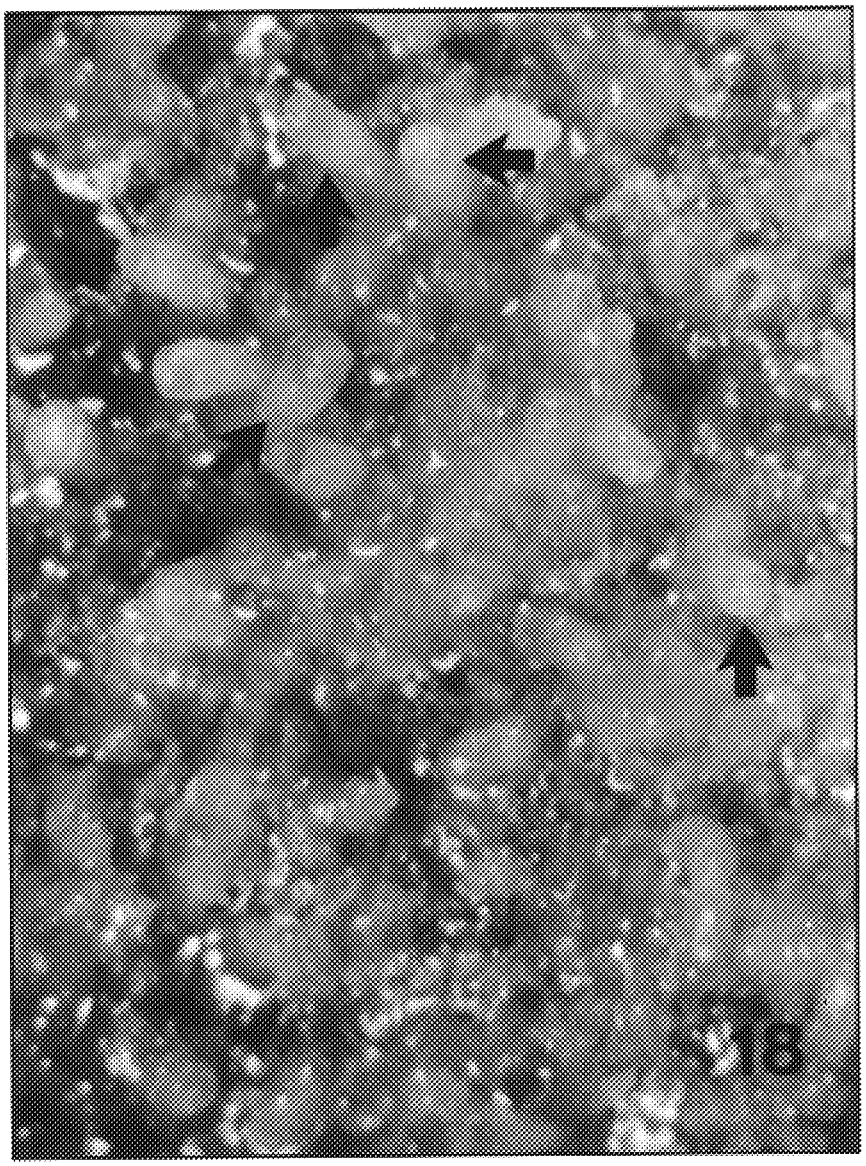
FIG. 18 shows the masses of parthenotes growing into embryos bearing cotyledons.

FIG. 18 illustrates that when plated as described in *Plant Cell Repts.*, 7:134 (1988), the ESM masses grow into embryos, approximately 4 to 5 mm long, bearing cotyledons.

Division of $pE_L$ cells appeared to occur by a restitution-like amitotic process. These divisions led to the deterioration of parthenotes. Restitution also occurs in meiosis and when the diploid cell products are viable, then this will enable diploid parthenogenesis.

A dozen free nuclei were previously found in the proembryo of Araucaria (*Bot. Gaz.*, 59:1 (1995)) and Agathis (*Ann. Bot.*, 27:1 (1913)). These numbers were approached in the current cell cultures of Norway spruce by the addition of low levels of colchicine. In the current study with Norway spruce, neither karyogamy nor nuclear fusion was observed, although colchicine is known to inhibit nuclear fusion.

Coenocytic stages, developed by the repeated division of free nuclei in parthenotes ($pE_L$ daughter cells), restored the early proembryonic development characteristic of Norway spruce.

Latent diploid parthenogenesis in spruce and its coupling to polyembryony have considerable genetic significance. First, the occurrence of free-nuclear stages in early ontogeny of egg-equivalents and parthenotes may be viewed in terms of a developmental hetero- and homokaryotic advantage. One nucleus of the binucleate state in a common cytoplasm was not always equivalent to the other in development fate nor in its affinity for stains. These differences indicate that the studies were performed under a developmentally heterokaryotic condition. However, with colchicine, most daughter nuclei had equivalent volumes and staining behavior except at high concentrations, when aberrations were seen. This shows that a homokaryotic coenocytic condition occurred through a rapid series of nuclear divisions. The repeated free-nuclear divisions acts as a way to enhance the potential equivalent effects of ploidy. Ploidy is regarded as one of the prerequisites or preadaptive conditions for apomixis and precocious parthenogenesis. Ploidy changes may arise by restitution meiosis or by endoreduplication, both yielding 2n progeny. Meiotic restitution occurs naturally in Norway spruce trees showing asyndesis, i.e., abnormalities leading to the avoidance of meiotic reduction. Unreduced eggs have been noted in Tetraclinis (Cupressaceae) as a natural occurrence, and therefore it is not surprising that the meiosis can occur in spruce cell suspensions.

Ploidy correlates geometric increases in DNA with nuclear volumes. Under high concentrations of colchicine, most daughter nuclei generated by the repeated proliferation of the egg-equivalent nuclear genome were subjected to genetic changes and extreme parthenoclonal variation. Changes in ploidy and nuclear volumes in free $pE_L$ cells seen after high colchicine treatments explain the occurrence of abortive $pE_L$ cells and parthenotes.

3. Variations in Free-Nuclear Expression

In the absence of a prior model for conifer parthenogenesis, there are other latent variations in apomictic expression, based on the examination of nuclear cycling and cell fates. Under artificial culture conditions, the nuclear-based ontogenetic program of Norway spruce showed remarkable plasticity beyond that expected for this species. The study of individual cells indicated that nuclear cycling could exceed the eight (FIG. 5) to ten-nucleate stage (FIG. 11) However, recent repetitions of this work has shown larger numbers of free nuclei especially in Araucaria and Norway spruce but not in Pinus species or Douglas fir. The combined set of four critical factors in the culture medium, as seen in FIG. 19, provided the stabilitizing selection to establish the process in bioreactor. This was demonstrated over a four year period.

FIG. 19 illustrates recovery rate of early embryo (parthenote) after 30 days as a percent and based on the mean for 2 batches. Standard deviation around each point does not exceed 26%. FIG. 19 shows recovery rate in the presence of 2,4-dichlorophenoxyacetic acid. FIG. 19B shows recovery rate in the presence of myoinositol. The dotted line from 1000 to 5000 mg/l indicates a preponderance of $pE_L$ cells in the medium. FIG. 19C shows recovery rate the presence of casein acid hydrolysate (low sodium). FIG. 19D shows recovery rate of parthenote in the presence of abscisic acid.

Requirements for the pre-adaptation of cells to express asexual reproduction according to the invention combine the genetic background for parthenogenesis with continual cultural conditions atypical for Norway spruce, such as for example, constant high temperature (22°–25° C.) v. mean temperatures of 16° C. (range 5° C. to 30° C.) after fertilization under field conditions, exposure to natural and synthetic plant growth regulators (colchicine, 2,4-D, BA, abscisic acid), provision of a rich supply of nutrients comprising reduced organic nitrogen phosphorus in casein hydrolysate, and the higher than normal $CO_2$ levels suspected in the rapidly proliferating embryonal-suspensor masses. After 7 days, the dry mass of embryonal-suspensor at 15° C. was approximately 40% below that at 23° C. Abscisic acid alone (3.8 $\mu$M) as seen in FIG. 19D, increased the dry weight over controls without other exogenous plant growth regulators by 10%.

Cultural conditions of the invention approach the mean environmental conditions of the Mesozoic, when gymnosperms were evolving under what are estimated to be conditions of high $CO_2$ (4×) and high temperature (26°–28° C.). The recovery of parthenotes through nuclear cycling at high temperature may have cenogenetic and possibly palingenetic implications. The linkage of both parthenogenesis and polyembryony cleavage shows that free nuclear multiplication in the egg and egg-equivalent is an early and precocious form of cleavage polyembryony leading to asexually multiplied populations. The experimental coupling of parthenogenesis with cleavage polyembryony extends the concept of totipotency, with its emphasis on the special role of the zygote and its built-in capacity to grow to include the origins of latent and non-latent asexuality with palingenetic and cenogenetic expressions under artificial conditions.

The current process demonstrates that a gametophyte comprising a single axial row can be generated in one step and by a change in environment rather than by mutation in a species that normally produces large female gametophytes.

Sequential steps for determining the origin of diploid parthenogenesis. The explant or rescued embryonal suspensor mass is represented as a diploid sporophyte (selected genotype here is diploid as indicated by 2n). For diploid parthenogenesis, the cells should show no reductional meiosis nor the formation of a linear tetrad. These are negative selection markers, that is, if normal meiosis or a linear tetrad forms, diploid parthenogenesis is not achieved. These steps are important if the explant represents the reproductive stages, such as male or female flowering buds, of the mother tree genotype that is selected for diploid parthenogenesis. However, in cell cultures of explanted sporophytic tissues of gymnosperms, diploid parthenogenesis is first seen if the somatic cells pass through a free nuclear stage (FIG. 1) that represents a central cell, for example a progenitor of the egg-equivalent. Archegonial cells are identified by their numbers and fates of free nuclei with reference to the equivalent process of nature. The natural process serves as an important model reference to help identify the diploid parthenogenesis process. The archegonium (central cell) in the center of the chart is equivalent to cell type A in FIG. 1. The egg-equivalent stage is the same as cell type B in FIG. 1. No fertilization is equivalent to cell type C. Parthenote development is the same as cell types D to H. Parthenote and proembryo development are indistinguishable from each other but are usually characteristic of the genotype. This is important because it shows that diploid parthenogenesis gives rise to clonal embryos that are the same as occur in nature by zygotic and somatic embryogenesis and even polyembryogenesis. Karyotype analysis with Feulgen and Giemsa stains as in FIGS. 15 and 27 support the current findings that the products are diploid.

UTILITY

The current invention is useful in horticulture for asexual reproduction of gymnosperm trees. Tree improvement programs can take advantage of this technology primarily to capture genetic gains overt and latent in elite highly heterozygous individual trees. Reproductive plasticity shown by the elite spruce genotypes indicates that, while the clonal variation of the sporophyte may be low, the genotype retains a latent reproductive plasticity that may be recovered under artificial conditions. Should climate change at the planting sites, there is enough latent capacity for the reproductive cells to survive by polyembryony and by introducing new genetic variations in the ontogenetic processes, such as progenesis, palingenesis or cenogenesis.

The advantages of using apomicts relates to their value as being highly heterozygous. The apomictic process fixes the hybrid vigor in true-breeding hybrids. Apomixis increases the opportunity to develop superior gene combinations that would be ready for immediate performance testing in different environments and climates. Fewer fertility problems may be encountered since meiosis is eliminated during the process. Apomixis simplifies hybrid seed production by eliminating the need for isolated plantings to produce F1 hybrids, for example. Fertilization is not involved in clonal production. There is no need to maintain and increase parents of the F1 generation. An apomictic hybrid could be grown as a single line. Apomixis could eliminate outcross contamination and minimize the need for mechanical mixtures of seeds in and fewer lines would be handled. Male sterility and fertility restoration systems would not be needed to produce commercial hybrids.

The invention allows the recovery of the parthenotes of elite genotypes from tree breeding and improvement programs. When grown under selected field conditions, it will be possible to continue the exposure of clonal subpopulations to simulated primitive conditions and to predict future climatic variables. This will establish the viability and fitness of the new generation. Results will allow deeper insight into ontogenetic imprinting and physiological preconditioning by climate at the seed source. This will further enable a novel evaluation of how genotypes may respond in scenarios of global climatic change.

The method further enables the testing of genotypes in today's forest for their reproductive adaptive responses to critical parameters in atmosphere-biosphere models, and of strategies of fitness and survival from one generation to the next. Interpretations are referenced to morphological markers from extant "living fossils" during the cell fate-mapping of the adaptive responses by spruce cells.

EXAMPLE 1

Diploid Parthenogenesis in Norway Spruce

This example illustrates the method and conditions for optimal diploid parthenogenesis for Norway spruce.

Cell suspension cultures of *Picea abies* L. [Karst.] were originally established by Dr. K. Jokinen (Kemira Oy, Helsinki, Finland) in 1988 from Finnish seed sources (ENSO: P27-85-01 lat. 61°–62° N and long. 27°–29° E). Cleaving embryonal-suspensor masses were rescued from individual mature, but fresh seeds, by removing the whole unit without cutting a part of the unit. For example, an explant may involve cutting a bud from a shoot. By contrast, while the ESM is removed from the seed, it is rescued as a whole unit onto a supporting medium. The bud may be considered as a whole unit but its survival depends on correlations and attachment to the tree. The ESM may depend on support from the seed but the dependency on the separated tissue may not be so strong as for an excised bud.

Monozygotic cell lines were cultured on 0.3% (w/v) Gelrite Gellan Gum (Merck Co., Inc.) and transferred every 3 to 4 weeks on a half-strength LP medium, according to *Plant Physiol.*, 127:233 (1987) modified with $NH_4NO_3$ at 15 mM and L-glutamine at 3 mM. Cultures were maintained in darkness at 23°±2° C. since 1989 on a medium containing 2,4-dichlorophenoxyacetic acid (2,4-D) at $9\times10^{-6}M$ and $N^6$-benzyladenine (BA) at $4.4\times10^{-6}M$.

Cell suspensions were established at the University of California at Davis, six months after rescue from two genotypes, in Steward's 1 liter nippled flasks at an inoculation density of 1 g fresh mass per 100 ml medium and rotated vertically at 1 rpm. Suspensions were subcultured every 7 days. Scale-up was achieved in 1.5 l. Multigen stirred tank bioreactor, (New Brunswick, N.J.) had an inoculation density of 1 g fresh weight per 100 ml medium. The recovery of individual somatic embryos and parthenotes with shoot and root meristems from these cultures in Petri dishes was performed by the method described in *Plant Cell Repts.*, 7:134, (1988).

EXAMPLE 2

Cell Fractionation and Fate Mapping

This example illustrates methods used for cell fractionation and fate-mapping.

10 grams fresh weight of cell suspension was recovered from two 1-liter nipple flasks and fractionated through 150

μm sieve. The cellular material (approximately 0.5 gm) passing through the sieve was loaded onto a gradient of liquid 5, 10, 20, 30, and 40% (w/v) Ficoll (M.W. 400,000) in half-strength LP medium in a plastic test tube. After centrifugation at 100×g for 20 minutes, fractions were drawn-off with a Pasteur pipette. Cell fractions were washed in a full-strength medium and inoculated into triplicated plastic multiwell plates. Each well had 5 ml of fresh LP medium with 100–500 mg fresh mass of cells.

The recovered fractions enabled the visual and cytochemical study of populations of individual cells and small clumps for comparison with cell models and events observed in FIGS. 1 and 20. The small size and uniformity of each replicated fraction in multiwell plates enabled fate-mapping of individual cells with and without staining. Fates of cells were followed over an 8-week period, using sequential time-lapse photomicrography (Zeiss M-35 inverted photomicroscope). ontogeny was also model-referenced to what is known in the literature on gymnosperm embryogenesis, as described in *Embryology of Gymnosperms,* 302, Gebruder, Borutraeger, Berlin (1978); *Stud. Forst. Suecica,* 45:1 (1967); *Med. Fran Statens Skogforsk,* 46:1 (1957), *Morphology and Evolution of Vascular Plants,* 626, W. H. Freeman, New York (1989).

EXAMPLE 3

Cytochemical Staining

This example illustrates method for cytochemical staining to determine the occurrence of egg-equivalent cells, parthenotes, the free nuclear stages, and ploidy in cell populations.

Freshly harvested cells and early embryos were stained with acetocarmine with or without Evan's blue according to *Biotechnology,* 5:710 (1987). Cells were also fixed in a mixture of 96% methanol and glacial acetic acid (3:1 v/v) for 24 hours. After a short rinse in distilled water, the cells were kept in 70% ethanol. This step was followed with hydration in 35% and 17.5% ethanol and water in 2-minute steps. Cells were stained with silver according to *Experimentia,* 36:1014 (1980), Giemsa according to *Cytologia,* 54:553 (1989), Feulgen according to *Chromosome Techniques, Theory and Practice,* 121, Frankenhaun Press Ltd., Norfolk), Feulgen-Giemsa according to *Hereditas,* 104:321, (1986), and 4'6-diamidino-2-phenylindole dihydrochloride (DAPI) according to *Exptl. Cell Res.,* 142:455, alone or in combinations. Permanent slides were prepared with permanent synthetic resin (Cover Bond, Scientific Products). The results were evaluated by reference to model criteria for the same developmental and morphological and cytochemical stages typical for the genotype and as expressed in nature. Matching sequences of developmental events were pattern matched to see if results comply with what is expected of development.

EXAMPLE 4

Diploid Parthenogenesis, Somatic Embryogenesis and Plantlet Regeneration from Norway Spruce (*Picea abies*) Embryos This example illustrate diploid parthenogenesis and somatic embryogenesis and plantlet regeneration from Norway spruce (*Picea abies*) embryos.

Seeds were collect (DDR Thuringerwald Streudorf, Lot No. 4-1347B and were provided by Dr. Peter Krogstrup). They were stored for two years at 4° C. For both diploid parthenogenesis and somatic polyembryogenesis, fresh seeds are ideal but stored seeds can be used with a reduction of success. For example, 5 year old seeds of sugar pine may be usable with a success rate of 1 in a thousand as opposed to immature fresh seed where nearly every seed is useful if not damaged in collection. Individual seeds were surface sterilized and imbibed for twenty-four hours in sterile water.

ESMs, early embryos and embryos were removed as products from a single fertilization event such as, for example, from a single archegonium to assure that the they are monozygotic, from individual seeds and inoculated directly on a semisolid agar or gelrite Gellan Gum medium. For diploid parthenogenesis the aseptic cultures were subcultured every 3 to 4 weeks on half-strength LP medium modified to have ammonium nitrate at 15 mM and L-glutamine at $3 \times 10^{-3}$M. Cultures were maintained in darkness at 20 to 25 degrees centigrade with 2,4-dichlorophenoxyacetic acid at $9 \times 10^{-6}$M and benzyladenine at $4.4 \times 10^{-6}$M. Cell suspensions were established from several genotypes in 1 liter nippled flasks at an inoculation density of 1 g fresh weight per 100 ml of medium and rotated at 1 rpm. Inoculation density and rotation are flexible and found empirically for the genotypes but the above values are the general values.

Cell suspensions were scaled up in 250 ml nipple flask and/or in a bioreactor, such as 1.5 L Multigen (New Brunswick, N.J.) stirred tank bioractor. At this time cells were exposed to higher temperatures (above 25° C. to 35° C. but preferably 25° C.–28° C.) and/or exposed to higher levels of humidity and carbon dioxide simply by sealing the neck of the flask tightly so no gas escapes for the subculture time of once every 2–3 weeks. Various concentrations of carbon dioxide was controlled and introduced into the bioreactor with gas levels being 3 to 5 times above that found in normal air.

Cytological examination of individual cells was followed by removal cells and by microscopic and cytochemical examination. If cells were subcultured in small plastic multiwell plates the cells could be observed directly by an inverted tissue culture microscope. The range of cells types and behavior as found by time lapse study is shown in FIG. 1. These observations were referenced to what is known in the literature on gymnosperm embryogenesis. The parthenotes appeared after tubular megakaryocytes, central cells and egg-equivalents (FIG. 1, cell type A) were first detected free in the culture medium. The terms used for cell type A depends on how they develop in a sequential way as shown. The terms are for practical purposes referring to the same progenitor cell type as long as the sequence in FIG. 1 occurs. This process has now been repeated over a period of several years with cultures established in 1988.

Within thirty days, visually two distinct types of cell masses were produced. On BM-2, 5–6% of the excised embryos developed two types of visually distinct tissue masses. One type was a callus because daughter cells contributed to the growth of a nondescript mass of cells with some cells having the capacity to produce embryos. The second type of cell mass was called an embryonal-suspensor mass or ESM because no callus cells were observed and the mass contained already embryos at various stages of development, for example, there was no need to induce embryony because it was already there. By contrast with a callus, no embryony was present and embryony had to be induced by further subculture. Callus developing from the cotyledons was green and compact. Callus from the radicals was white, translucent and embedded in a viscous mucilaginous matrix. This callus contained remnants of the ESM that mixed with the callus because the embryo normally grows out of the ESM and subculture can lead to a callus in this region. For this reason cytochemical verification of the fate of the cells in the mass types becomes more important as distinguishing the origins of the different possible processes. Diploid parthenogenesis may be occurring in the ESM but this can only be determined by observations if cells behave as in FIG. 1.

The formation of the embryonal-suspensor mass was not dependent upon having an intact embryo as the initial explant. The non-embryonic callus and proliferation EMS were subcultured with low cytokinin and 2,4-D. Within ten–fifteen days, numerous somatic embryos emerged from the white mucilaginous embryonal-suspensor mass derived from the radical. Embryos in this mass developed in networks of polyembryonic clusters. Each embryo consisted of a linear array of elongated cells at one end (like suspensors) and a small highly dense cluster of cells with large nuclei typical of developing embryos at the other end. These polyembryonic somatic structures were strikingly similar to those seen during the early stages of zygotic embryogenesis. Somatic embryos were not evident among calli originating from cotyledons under these experimental conditions.

Aberrant development, involving the amplification of shoot and root development, was observed at longer subculture rates when embryogenic cells developed more as a callus and polyembryonic clusters were not separated and dispersed from one another. Embryogenic cell masses were maintained at several (about ten–twelve) day intervals by subculture on the same medium. Embryonic growth beyond the globular stage was always arrested in the BM-3 medium. For this reason, proliferating embryonal-suspensor masses with their polyembryonic clusters were transferred to a low concentration of 2,4-D ($1 \times 10^{-6}$M) medium (BM-4). Within fifteen days, enlarged globular stages of development were observed. By fourteen days, some (ca. >25%) of these numerous globular structures produced chlorophyll even when maintained in darkness. Morphogenesis of embryos continued on the same medium up to the torpedo stage of late embryonic development.

Within twenty–five to thirty days, embryos developed into complete plantlets when transferred to basal medium (BM-1) with 0.25% (w/v) activated charcoal and without organic nitrogen (CH and glyc). These plantlets were then established in soil.

In addition, subcultures over 8 years were carried out on BM-3 at ten-to-twelve day intervals without reduction of embryogenic potential. However, incubation periods longer than approximately ten to twelve days on BM-3 or BM-4 inhibited embryo development and induced aberrant embryogenesis and true callus formation. Both characteristics are undesirable for mass clonal propagation. Approximately 40±10 somatic spruce embryos representing the phenotype of the new generation were recovered within 150 days for each embryonal-suspensor mass (approximately 50 mg fresh weight). The yield of somatic embryos were improved about 100±10 with the use of ABA (see Example 5). This is relevant to diploid parthenogenesis in the sense that parthenotes or embryo equivalents go through the same process, but diploid parthenogenesis has a different cell type origin.

EXAMPLE 5

*Araucaria Augustifolia* Diploid Parthenogenesis

This example illustrates the method and conditions for optimal diploid parthenogenesis for *Araucaria Angustifolia*.

The same method and formulations can be used as in Norway spruce. Modifications of plant growth regulators are needed for some genotypes. These modifications are genotype specific.

Monozygotic cell lines from Santa Catarina, Brazil, were provided in 1993 by Dr. Guerra. Araucaria is one of the few conifers that does not show overt cleavage polyembryony in vitro although some cleavage occurs under the conditions used in Example 4 for Norway spruce.

EXAMPLE 6

Diploid Parthenogenesis and Somatic Polyembryogenesis in Douglas Fir

This example illustrates diploid parthenogenesis in Douglas-fir (*Pseudotsuga menziesii*). For diploid parthenogenesis the protocol for Norway spruce is used and cells showing behavior as in FIG. 1 are selected. Douglas fir passes through the stages in FIG. 1 but does not show more than 4 to 8 free nuclei at the proembryonal stage. Douglas fir gives the same results as Norway spruce with the release of parthenotes into the culture medium.

Genetically improved seed of Douglas-fir (*Pseudotsuga menziesii*) were collected in June 1985 and obtained as gifts of Weyerhaeuser's forest seed orchard. Seed cones were stored at 4° C. until used for this study. Seeds from cones were removed and surface sterilized. Female gametophytes with attached suspensors and proembryos were excised from seeds every week just after fertilization (June 15) until seeds reached full maturity (September 15).

Each week, tissues were inoculated on two culture media as described in Example 1. Factors evoking somatic polyembryogenesis SPE from over 500 explants were established using five-fold replicated treatments.

DMH media were used. Medium was supplemented with 2,4-D, KN and BAP at an initial pH of 5.7 before autoclaving. Media can also be filter-sterilized. Cultures were maintained in dark at 23° C.±2° C.

After three-four weeks, a white slimy proliferating embryonal-suspensor mass (ESM) was obtained from 20–25% culture embryos on BM1, with 2,4-D ($5 \times 10^{-5}$M), KN, BAP each at ($2 \times 10^{-5}$M). At this stage, ESM was subcultured to DCR1 with 2,4-D ($5 \times 10^{-6}$M) KN, BAP each at ($2 \times 10^{-6}$M). ESM consisted of embryonal cells (smaller cells with large nuclei and dense cytoplasm) which stained red with acetocarmine and suspensor cells (large vacuolated cells) which stained blue with Evan's blue. Subcultures were done every ten to twelve days intervals.

EXAMPLE 7

Effect of Abscisic Acid (ABA) on Diploid Parthenogenesis Somatic Embryogenesis and Polyembryogenesis This example illustrates affect of abscisic acid (ABA) on somatic embryogenesis and polyembryogenesis. For diploid parthenogenesis, the addition of abscisic acid (Table 1) enhances the dry weight of cells showing diploid parthenogenesis as does the other plant growth regulators. Colchicine is the best among these. The main effect of these compounds is to enhance the free nuclear cycling so that more free nuclei are formed in the egg-equivalent cytoplasm (FIG. 1). This contributes to the release of more parthenotes into the culture medium and to formation of more clones.

For somatic polyembryogenesis, embryonal-suspensor masses growing on suspension culture on 2,4-D ($5 \times 10^{-6}$M), and KN, BAP (each $2\times10^{-6}$M) (BM-3, as described in Example 2, without agar) were transferred to basal medium (BM-1 in Example 2) with ABA ($1\times10^{-6}$M) without 2,4-D, KN and BAP. This consisted of five ml packed cell volume in 40 ml medium in 250 ml Erlenmeyer flasks rotating on 50 rpm in the dark at approximately 22° C. Subcultures were carried out by removal of old medium and the addition of fresh basal medium with ABA at every seven day intervals. The osmolality of culture media at 20°–20° C. that was considered optimal was between 149 and 235 mOsm.

Polyembryogenesis was inhibited after four–five subcultures with ABA. ABA inhibited the polyembryogenesis and encouraged the complete development of individual somatic embryos. After four–five subcultures, complete embryos started growing on basal medium after the removal of ABA. This was observed in Picea abies, Pinus taeda and Douglas fir.

EXAMPLE 8

Somatic Polyembryogenesis and Diploid Parthenogenesis in Loblolly Pine (Pinus taeda L.)

This example illustrates somatic polyembryogenesis and diploid parthenogenesis in Loblolly Pine (Pinus taeda L.)

For diploid parthenogenesis in loblolly pine, the selection of cell type A in FIG. 1 is critical. Diploid parthenogenesis occurs in conjunction with somatic polyembryogenesis and under the same conditions of culture. This is verifiable by sorting and searching cells in the population for callus, diploid parthenogenesis and somatic polyembryogenic types of cells, such as for example, cells of the proembryo, early embryonal axial tier, etc., using what is known about early development in loblolly pine and about the genotype that is under investigation.

Improved seed of loblolly pine Pinus taeda L. were collected on June 1985 and obtained as gifts of Weyerhaeuser's forest seed orchard (Lyons, Ga.). Seed cones were stored at 4° C. Seeds from cones were excised and surface sterilized. Female gametophytes with attached suspensors and proembryos were excised from seeds every week just after fertilization (June 10–15) until seeds reached full maturity (September 30).

Initially each week tissues were inoculated on two culture media. Factors evoking SPE and associated with these media were established from over 1000 explants using five-fold replicated treatments. Based on this work, the MS basal medium with modification of $NH_4NO_3$ (550 mg/l), $KNO_3$ (4674 mg/l), and thiamine●HCl (1.0 mg/l) was used. Half-strength modified MS medium was supplemented with myo-inositol (1000 mg/l), sucrose (3%), L-glutamine (450 mg/l), casein hydrolysate (500 mg/l), 2, 4-D ($5\times10^{-5}$M), kinetin, and $N^6$-benzyladenine (each at $2\times10^{-5}$M) at an initial pH of 5.7 before autoclaving. Cultures were maintained on 0.6% agar (Difco Bacto) plates in darkness at 23°±2° C.

To complete early embryony the proliferating embryonal-suspensor mass bearing the early stages of SPE was subcultured to the same medium as described above, except that 2, 4-D ($5\times10^{-6}$M), KN and BAP (each at $2\times10^{-6}$M) were added. After three or four subcultures, the globular stage of embryogenesis was fully evident. Embryos elongated and developed cotyledons within eighth to ten weeks at 25°±2° C. when transferred to a sterile-filtered liquid medium with filter papers support without growth regulators and under continuous white light (5.0, 2.0, 0.5 $\mu$W cm$^{-2}$ nm$^{-1}$ in blue, red and far-red, respectively). Complete plants were developed in a half-strength basal medium containing 0.25% w/v activated charcoal (E. Merck), myo-inositol (100 mg/l) and sucrose (2%). Casein hydrolysate and glutamine were removed. This subcultured sequence completed the recovery of plantlets from embryonal-suspensor mass on agar plates.

For cell-suspension culture, embryonal-suspensor masses (~2 g in 50 mls) were placed in shaking (120 rpm) 250 ml Erlenmeyer flasks with fluted bases. The culture medium was 0.5 strength MS (as described above with 2,4-D ($5\times10^{-6}$M), KN and BAP (each $1\times10^{-6}$)). Cell suspensions formed rapidly in darkness when maintained and subcultured every five to six days. Repeated subculture produced well-dispersed suspensions of single cells, aggregates of two to five cells and larger embryonal-suspensor masses. Packed cell volume was measured after centrifugation of cell suspension of each flask at 250×g for ten minutes.

Histological and Cytochemical Staining for Diploid Parthenogenesis and Polyembryogenesis Cells in suspension cultures or in embryonal-suspensor mass or callus were stained as follows. Cells in suspension culture showing binucleate and multinucleate conditions with light microscopy were reexamined by cytochemical methods for diploid parthenogenesis, as shown in FIGS. 1 and 20, and for subsequent development as embryonal-suspensor masses. Samples of cells (packed-cell volume of 5–10 $\mu$l) were suspended in liquid medium to which 2% acetocarmine (1:1 v/v) as described in Example 1, was added. Cultures were heated slightly for fifteen seconds, and filtered to remove excess stain. 0.5% Evan's blue (1:1 v/v) was added in acetocarmine stained cell suspension and washed with medium to remove excess of stain and filtered. After double-staining, cultures were resuspended in 100% glycerol to improve optical clarity of cells on slides for microscopic inspection and the distribution of dyes followed microphotographically. The process was repeated with Feulgen and Evan's blue. The stains were also used to follow somatic polyembryogenesis from cell masses that developed by diploid parthenogenesis.

Repetive conifer-type SPE was obtained as follows. Within three to four weeks after inoculation on half-strength modified MS medium with supplements containing 2,4-D ($5\times10^{-5}$M) and KN and BAP ($2\times10^{-5}$M), a white mucilaginous cellular mass was obtained in darkness from around the female gametophytes of the seeds four to five weeks after fertilization. This embryonal-suspensor mass (ESM) was similar to the ESM described for Norway Spruce in Example 1.

Mucilaginous embryonal-suspensor masses were found in 9 to 10% of the total explants cultured. Light microscopic examination of the masses egg-equivalent revealed proembryonic stages and early embryonic stages. This proliferating embryonal-suspensor mass are not called a callus because of its origin, cellular composition and developmental potential is different from proliferating EMS. Cells derived from friable and non-friable embryonic callus under identical culture conditions are distinctively different in shape and growth pattern in that they do not incorporate acetocarmine or exhibit the red stain resulting from absorption of acetocarmine characteristic of the proliferating embryonal-suspensor mass cells.

TABLE 2

Affinity of Organelles in Suspension Cultures

|   |   | Nucleus | | Cytoplasm | |
|---|---|---|---|---|---|
|   |   | Aceto-carmine & Feulgen | Evan's Blue | Aceto-carmine & Feulgen | Evan's Blue |
| A. | Embryonal-suspensor Mass* | | | | |
|   | Proembryonal Cells | 5 | 0 | 3*** | 0 |
|   | Suspensors | 1 | 4 | 0 | 2 |
|   | Callus | 2 | 2 | 1 | 2 |
|   | Free-nuclear stage*** (egg-equivalent) | 5 | 3–4 | 1 | 1 |
| B. | Nonembryogenic Callus | 2 | 2 | 0 | 2 |

*Callus is not observed in the explant of the original embryonal-suspensor mass.
**Some transvacuolar strands strongly reactive.
***Individual nuclei differ in their ability to accept stain.

As shown in Table 2, two extreme major types of nuclei in the egg-equivalents and embryonal-suspensor masses are easily distinguished by the double staining method. First there are the large nuclei having approximately >10 microns dia.). These are egg nuclei that become proembryonal cells in diploid parthenogenesis. In nonegg-equivalent cell, these nuclei give rise to a free nuclear stage typical of a proembryo. Further embryo development shows embryo multiplication by cleavage. Nuclei in a free nuclear state stain intensively with acetocarmine and Feulgen. Strands in the cytoplasmic show an affinity for acetocarmine and may represent cytoplasmic fibers. Elongated cells from embryonal-suspensor mass which have been subcultured in the half-strength modified MS medium with supplements and 2,4-D ($5\times10^{-6}$M) KN and BAP (each at $2\times10^{-6}$M) exhibit noticeable acetocarmine-reactive protoplasmic strands and nuclei after the double staining procedure. Acetocarmine and Feulgen are stains normally used to detect glycoproteins, chromatin and DNA in cytochemical studies.

Second, smaller nuclei (ventral canal) may deteriorate as egg-equivalents mature. Small nuclei in proembryonal stages of parthenote or somatic embryo development react with Evan's blue to further differentiate the overall steps in the process. Exclusion of Evan's blue and a strong DAPI or fluorescein diacetate reaction indicates a high viability state of the nucleus and/or cell. Less viable cells and nuclei permit more Evan's blue to enter. By contrast, nonembryogenic cells do not stain as strongly by the double-staining procedures (see Table 2).

The proembryonal stage of parthenote and somatic embryo development was characterized by a typical four free-nuclear stage. During the late free-nuclear stage the red staining proembryonal nucleus migrated to the cell wall to form the early embryonal group of cells of the early embryo. These are red-staining cells. The blue-staining nuclei of the free nuclear stage contributed to the formation of the axial tier. This process is consistent with the early development (basal plan) in pine species. Some suspensors of the early embryo has nuclei which retained an affinity for acetocarmine. These had the potential of producing somatic embryos by cleavage or by release of cells into the culture medium to reinitiate the process of diploid parthenogenesis. The direct production of nonembryonic callus from the proliferative embryonal-suspensor mass was not evident. However, some cells (greater than 10%) in the ESM did not fall into an easily classified category and could possibly represent the tendency to form callus as they did not stain intensely with either or both of the red and blue dyes (Table 2). Alterations of the process selected removed these colonies on semisolid media plates.

Diploid parthenogenesis involves the migration and segregation of nuclei in egg-equivalent cells as in nature. Actual migration of the nuclei was observed. Wherever a new somatic proembryo emerged, the red staining nuclei was always very closely associated with the cell wall at one pole of the initially multinuclear egg-equivalent cell. Mitosis may split off new proembryonal cells with large nuclei thereby contributing to the vivid red color of the prospective embryo.

The origin of the blue-staining nuclei was evident after freezing the ESM in liquid nitrogen ($-196°$ C.) for 30 minutes and recovering the mass by rapid thawing. The thawed ESM was placed on a modified half-strength MS basal medium with 2,4-D ($5\times10^{-6}$M) and KN and BAP ($2\times10^{-6}$M) medium. Upon recovery of cells, nearly all of the suspensor cells of the blue staining nuclei were killed to leave viable embryonal cells with large nuclei. After three weeks, these cells divided with the production of the suspensor with nuclei having a typical affinity for Evan's blue. Several rooted plantlets were recovered from these revived embryonal cells.

Early embryogeny was produced repetitively over one year by subculture on agar every ten to twelve days on the half-strength modified MS medium with supplements and 2,4-D ($5\times10^{-5}$M) and KN and BAP (each $2\times10^{-5}$M). Delaying the rate of subculture caused browning of cells, the loss of embryogenic potential, the proliferation of nonembryogenic callus and death. Further growth and development of all cells were arrested on the initial medium.

Further embryonic development, cotyledons, shoots and root primordia and plantlet stage was evoked by sequential subculturing. Longitudinal sections of elongated somatic embryos with multiple cotyledons revealed shoot and root apices. Within nine to ten weeks, complete plantlets developed. Plantlets were grown to plants in a mixture containing peat moss, vermiculite and pearlite with a ratio of 1:2:1.

The above somatic embryogenic developmental sequence was repeated to the early embryonal stage with embryonal-suspensor mass derived cell suspensions cultured in the 0.5 strength MS with 2,4-D ($5\times10^{-6}$M), KN and BAP (ea. $2\times10^{-6}$M). Growth and development of homogenous cell suspensions was encouraged by subculturing to growth regulator free medium. After thirty days, globular embryos ($0.43\pm0.02$ mm dia.) with suspensors ($4.5\pm0.23$ mm length) were recovered at a level of $1040\pm200$ embryos per 100 ml of medium. In somatic and zygotic embryogenesis, while subsequent divisions with blue and red staining nuclei, many cells ($45\pm20\%$) in the ESM retained nuclei with dominant red-staining properties. The division of the later contributed to the efficiency of the conifer-type somatic polyembryogenesis. From zero to ten days, the osmolality of the medium was increased from 190 to over 220 mOsm as the pH at $23°\pm1°$ C. dropped from 5.7 to 4.6. At lower pH, the cell suspensions deteriorated rapidly.

Histological inspection of the suspension cultured embryos revealed shoot and root apical meristems. This contrasted sharply with the unorganized growth and histological patterns obtained from nonembryogenic callus and suspension culture under the same treatments. By coupling the double staining procedure with fluorescence microscopy, the liquidification of suspensor could be observed at the onset of late embryogeny. Results with ESM and cell suspensions with and without 2,4-D indicated that 2,4-D is significant for the induction and maintenance of a proliferating ESM. After removal of 2,4-D, the addition of NAA ($0.5\times10^{-6}$M) improved the growth and development of somatic embryos. White light (2.8, 2.0, 0.5 µW cm$^{-2}$ nm$^{-1}$ in blue, red and far-red spectrum respectively) was inhibitory to the early stages of SPE but stimulated late embryogeny and plantlet formation.

Somatic embryos with cotyledons were separated and encapsulated in an alginate. Over fifteen capsulated somatic embryos were stored in darkness at 4° C.±2° C. for four months. All encapsulated embryos returned to 20° C. produced chlorophyll upon transfer to light. Their survival rate was not affected. Plantlets in soil were obtained from these stored embryos.

In the model for the zygotic proembryo of pine, the free-nuclear stage initiated by the first zygotic division produced the axial tier of cells in the early embryo. This first division resulted in two and then four free-nuclei. The nuclei migrated or were pulled to the base of the archegonia where they partially walled-off and initiated the proembryo. In somatic embryos, the same type divisions were shown to give the initial free-nuclear stage. Mitosis in the embryonal-suspensor mass contributed to the multiplicity of embryos in the polyembryogenic process. For Loblolly pine, somatic polyembryogenesis was repeated for over fourteen months. These observed developmental patterns were consistent with zygotic pine polyembryony in vitro.

Staining with Evan's blue indicated that organelles were leaky or at least permeable to the dye. Alternation in the cell wall and/or in plasmalemma and nuclear membrane organization facilitates rapid and intense staining behavior. This was demonstrated by enzymic removal of the cell walls to prepare protoplast. Protoplasts of highly acetocarmine-reactive embryonal cells stained strongly with Evans' blue. Acetocarmine staining indicated a concentration and enrichment of unidentified materials.

The origin of the repetitive or cleavage phenomenon was related to nuclear divisions and the fate of acetocarmine and Feulgen-positive nuclei in cells in cell suspension cultures.

Based on the staining results, it was determined that the embryonal-suspensor mass was not a callus but a cellular array of significant true-to-type developmental potential provided that the cultural conditions resemble the true environment of the egg. Nonembryogenic callus shows none of the observed staining or developmental properties under the same conditions. The staining and developmental nuclei characteristics described in this example have also been repeated with Douglas fir, Norway spruce and sugar pine.

When red and blue stains were combined sequentially, a useful nuclear-cytoplasmic diagnostic method was provided for determining the sequential stages of diploid parthenogenesis and conifer-type somatic and zygotic polyembryogenesis. The end result was a diagnostic method that identified types cells from stages of the life-cycle of a tree which may be suitable for mass true-to-type clonal propagation by this technology. Double staining may be followed through artificial seed formation and associated with low-temperature storage for assessment of embryonic potential until the field-testing of progeny can be completed.

It was determined that the suspensor provides the connection and much of the nourishment for the developing embryo based on the fact that embryos were pushed into the air from embryonal-suspensor mass supports. The development of one to five plantlets per gram of fresh cell mass on paper bridges is due presumably to competition, and to the depletion of nutrients in the ESM and possibly to the formation of substances by the suspensors that inhibit development of other somatic embryos. In contrast, over 1000 acetocarmine staining embryos were recovered from 100 mls of cell suspensions.

Lignification of early embryos was also observed. Since lignification provides structural stability, the lignification of a suspensor cells provided structural stability to the developing ESM. Lignification facilitated the hydrodynamic handling for embryos in bioreactors. If polyembryonic masses were not kept separate, a fabric was quickly formed by the proliferant and interweaving suspensions that make subsequent mechanical separations very difficult. However, the recovery of fully-developed somatic embryos from self-suspension cultures again fell-off dramatically even though the early stages of polyembryogenesis were maintained indefinitely. The repetive nature of SPE reflects the cleavage process in zygotic polyembryogenesis. SPE was distinct from somatic embryogenesis. Observed and diploid parthenogenesis repetive and conifer-type SPE therefore paralleled true-to-type zygotic development.

EXAMPLE 9

Somatic Polyembryogenesis from Embryo Suspensor-mass of Sugar Pine (*Pinus lambertiana*) Embryos This example illustrates somatic polyembryogenesis from embryo suspensor-mass of sugar pine (*pinus lambertiana*) embryos.

Seeds from specific crosses in 1980 were provided by B. Kinlock, U.S. Forest Service, Berkeley, Calif. They were collected at the Institute of Forest Genetics, Placerville, Calif. and were maintained at 20° C. Seed coats were removed, surface-sterilized and the embryos excised aseptically before being paced on a range of modifications for two culture media described in *Physiol. Plant.*, 15:473–493 (1962).

Excised embryos developed callus in all media within four to five weeks. By ten to twelve weeks for five-year old seeds and three–four weeks for immature seeds, an unusually white mucilaginous ESM was obtained from explants around the radicle on a variation of the DCR basal medium. In addition, the basal medium contained 30.0, 50 and 500 mg/l of 2,4-dichlorophenoxyacetic acid (2,4-D), L-glutamine and casein hydrolysate, respectively. The clear mucilage surrounding the white embryonal-suspensor mass retained at 23° C. the same osmolality of the medium (~125 mOsm). The mucilaginous embryonal-suspensor mass was found in only four–five percent of the total 200 embryos cultured under these conditions. Microscopic examination of the embryonal-suspensor mass revealed early and late torpedo-shaped embryos at various states of development with large suspensors protruding from the embryonal-suspensor mass. Cross-sections revealed that the somatic embryos contained shoot and root apices. Cells at the embryonal end were densely cytoplasmic with large nuclei. Development time and morphology were much like early stages of zygotic embryogenesis in conifers. Observations of free nuclear stages were observed. Other types of callus did not reveal signs or organized growth for the same medium.

The embryogenic embryonal-suspensor mass has been maintained indefinitely so far on a 2,4-D supplemented medium. However, the development of the somatic embryos did not proceed beyond twelve weeks unless they were transferred to a medium lacking 2,4-D and containing 0.1 mg/l N$^6$-benzyladenine (BAP). Transfer of embryos encouraged elongation of the embryonic axis and the true-to-type development of six–eight cotyledons in all cases.

The embryogenic-suspensor mass originated from suspensor cells which remained attached to the radicle of the zygotic embryos. Embryos induced in the embryonal-suspensor mass of suspensor cells stained bright red with 0.10% (w/v) acetocarmine. When unstained callus and embryonal-suspensor mass were viewed under UV light, embryonic cells exhibited a characteristic green fluorescence. Moribund cells gave a bright yellow fluorescence. Suspensor cells revealed a weak fluorescence. This display permitted determination of the developmental fates in the callus and embryonal-suspensor mass. The acetocarmine staining and fluorescence of cells has revealed that numerous embryonic cells are present initially in the mucilaginous matrix of elongated suspensor cells. This was the natural result of simple and cleavage polyembryony. In seeds of these seed lots only one embryo developed completely in the mature seed.

True-to-type developmental stages equivalent to zygotic embryogenesis were recapitulated within six weeks of culturing suspensor cells from immature seeds. The temporal processional stages of development occurred on the DCR basal medium supplemented with casein hydrolysate (500 mg/l) L-glutamine (200 mg/l), beta-indoleacetic acid (IAA) (0.2 mg/l), kinetin (0.1 mg/l) and myo-inositol (500 mg/l) at pH 5.9 (23° C.).

Transfer of embryos to a filter paper support in liquid medium lacking growth regulators promoted embryo elongation and the greening of cotyledons over 30 days. At this stage, the embryos were transferred to a basal medium without supplements and with 0.25% (w/v) activated charcoal under continuous light (2.8, 2.0, 0.5 $\mu$W cm$^2$ nm$^{-1}$) in the blue, red, and far-red range.

The embryonal cells are derived from zygotic proembryo and therefore contain the genotype of the new generation, not the mother plant. This occurs in somatic polyembryogenesis since the origin of the adventive embryos are from the suspensor tissue. The somatic polyembryogenesis is extremely true-to-type in temporal and developmental terms with the production of a large array of suspensor cells and embryos with multiple cotyledons.

The recovery of healthy and totipotent egg-equivalents and suspensor tissue from five year old seeds is difficult and unpredictable. The success often depends upon how seeds were stored and their origin. To overcome such a problem, a much higher percentage of totipotent cells was obtained by culturing the suspensor tissue from immature sees (two-four weeks after fertilization). This observation was supported by the increased number of cytoplasmically dense cells with large nuclei that stain with acetocarmine. Among these were the binucleate egg-equivalents characteristic of diploid parthenogenesis.

In explants from immature seeds the presence of the female gametophytes attached to the suspensor cells aided the establishment of the embryonal-suspensor mass and the development of somatic polyembryogenesis. Further improvement in the performance of the embryogenic process was seen by removal of the dominant embryo. Removal released the growth of smaller embryos. The somatic polyembryogenesis remained repetitive as long as the ESM was maintained on the 2,4-D medium.

Embryos transferred to the basal medium without supplements and with activated charcoal under continuous light produced complete plantlets within forty days at a low (one-two percent) conversion in the blue, red and far-red range.

The original initial physiological state of the explant, nutritional factors in the medium, sequential relationships among growth regulators is applied exogenously and competitive influences among embryos all contributed to the overall control of the developmental process.

EXAMPLE 10

Diploid Parthenogenesis in *Cupressus Sempervirens*

This example illustrates the method and conditions for optimal diploid parthenogenesis for *Cupressus sempervirens* cell suspensions were established exactly as for Norway spruce but medium improvements are possible. Genotypes were obtained from seeds on trees on the Davis campus and later from Ms. T. Scorano from trees in Firenze, Italy. ESMs of Cuopressus genotypes responded to half-strength LP and to modified B5 medium as described for other gymnosperms. The free nuclear stages compare with FIG. 1 and especially to H type cells and step 7. Early embryo development and cleavage was spontaneously expressed.

Although the foregoing invention has been described in some detail by the way of illustration and example for the purposes of clarity and understanding, it should be recognized that changes and modifications may be practiced within the scope of the appended claims.

What is claimed is:

1. A method for inducing asexual reproduction of hybrid seeds and plants having identical genetic characteristics by providing environmental conditions leading to diploid parthenogenesis and somatic polyembryogenesis, said method comprising the steps:

(a) selecting a genotype for asexual reproduction from a group consisting of Norway spruce, Sugar pine, *Cupressus sempervirens,* Douglas fir, Loblolly pine, and *Araucaria angustifolia;*

(b) obtaining a seed from the selected genotype;

(c) rescuing a tissue containing a proembryo, embryo and suspensor from the seed in time period from immediately after the seed fertilization to about three months after the fertilization and incubating rescued tissues on a half strength modified Murashige-Skoog or DCR basal medium supplemented with organic nitrogen sources, cyclitols, sucrose, and plant growth regulators present in amount from about 2–15×10$^{-5}$M, in darkness at from about 20° C. to about 30° C. for about 3 to 6 weeks until a white embryonal suspensor mass develops;

(d) determining a presence of an egg-equivalent binucleate stage in cells of the white embryonal suspensor mass;

(e) incubating the embryonal suspensor mass cells having said egg-equivalent binucleate stage on the medium, in darkness at 23° C. to about 26° C. for about three to about four weeks until they develop into parthenotes;

(f) subculturing a parthenot of step (e) on the same medium every ten–twelve days three or more times under the same conditions as in step (e);

(g) incubating said culture in darkness at 23° C. to about 26° C. for about three to about four weeks to develop into an early embryo;

(h) subculturing the early embryo on medium every ten to twelve days three or more times under the same conditions as in step (g);

(i) incubating the early embryo on basal medium MS-1 or DCR-1 containing reduced amount of inositol to about 100 mg/L, in a continuous light for about seven to eight weeks at about 23° C. to about 26° C. to convert the early embryos to somatic embryos developing multiple cotyledons;

(j) culturing the developed somatic embryo on the basal MS-1 or DCR-1 medium lacking an organic nitrogen source, for about five to six weeks until a plantlet develops;

(k) growing the plantlet into a plant; and (l) recovering hybrid seeds having the identical genetic characteristics from the plant.

2. The method of claim 1 wherein the medium in step (c) is MS-2 or DCR-2 medium, the medium in steps (e) and (f) is MS-3 or DCR-3 medium supplemented with plant growth regulators present in amount from about $2$–$15 \times 10^{-6}$M, the medium in steps (g) and (h) is MS-4 or DCR-4 medium supplemented with plant growth regulators present in amount from about $1 \times 10^{-6}$ to about $2 \times 10^{-5}$M, and medium in step (i) is modified basal MS-1 or DCR-1.

3. The method of claim 2 wherein the basal MS-1 medium comprising a half strength Murashige-Skoog medium, said MS-1 medium consisting essentially of

|  | mg/L |
|---|---|
| $NH_4NO_3$ | 200 |
| KCl | 32.5 |
| $KNO_3$ | 40 |
| $Ca(NO_3)_3.4H_2O$ | 72 |
| $KH_2PO_4$ | 6.25 |
| $MgSO_4.7H_2O$ | 36 |
| $H_3BO_3$ | 1.6 |
| $MnSO_4.H_2O$ | 6.5 |
| $ZnSO_4.H_2O$ | 2.7 |
| KI | 0.75 |
| NaFeEDTA | 25 |
| Kinetin | 0.2 |
| 3-Indoleacteic acid | 2 |
| Thiamine.HCl | 0.1 |
| Pyridoxine.HCl | 0.5 |
| Nicotinic Acid | 0.5 |
| Glycine | 2 |
| myo-inositol | 1000 |
| Edamin | 500 |
| Casein hydrolysate | 500 |
| L-glutamine | 450 |
| Sucrose | 30 g/L |
| adjusted to pH about 5.7 to about 6.0. | |

4. The method of claim 3 wherein the medium is MS-2 comprising medium MS-1 containing about $2 \times 10^{-5}$M kinetin and additionally containing about $15 \times 10^{-6}$M 2,4-dichlorophenoxyacetic acid and about $2 \times 10^{-5}$M $N^6$-benzyladenine.

5. The method of claim 4 wherein the medium is MS-3 comprising medium MS-1 containing about $2 \times 10^{-5}$M kinetin and additionally containing about $15 \times 10^{-6}$M 2,4-dichlorophenoxyacetic acid and about $2 \times 10^{-5}$M $N^6$-benzyladenine.

6. The method of claim 5 wherein the medium is MS-4 comprising medium MS-1 containing about $2 \times 10^{-5}$M kinetin and additionally containing about $1 \times 10^{-6}$M napthalene-2-acetic acid and about $2 \times 10^{-5}$M $N^6$-benzyladenine.

7. The method of claim 2 wherein the medium is DCR-1 medium comprising a half strength basal DCR medium, said DCR-1 medium consisting essentially of

|  | mg/L |
|---|---|
| $NH_4NO_3$ | 200 |
| $KNO_3$ | 170 |
| $Ca(NO_3)_3.4H_2O$ | 278 |
| $KH_2PO_4$ | 85 |
| $MgSO_4.7H_2O$ | 185 |
| $CaCl_2.2H_2O$ | 43 |
| $H_3BO_3$ | 3.1 |
| $MnSO_4.H_2O$ | 11.2 |
| $ZnSO_4.H_2O$ | 4.3 |
| $CuSO_4.5H_2O$ | 0.125 |
| Kinetin | 0.42 |
| $FeSO_4.7H_2$ | 13.9 |
| $Na_2EDTA$ | 18.65 |
| $CoCl_26H_2O$ | 0.012 |
| $NiCl_2$ | 0.012 |
| $NaMoO_4.2H_2O$ | 0.125 |
| Thiamine.HCl | 0.5 |
| Pyridoxine.HCl | 0.25 |
| Nicotinic Acid | 0.25 |
| Glycine | 1 |
| myo-inositol | 100 |
| casein hydrolysate | 500 mg/L |
| L-glutamine | 450 mg/L |
| myo-inositol | 1000 mg/L |
| sucrose | 30 g/L |
| adjusted to pH about 5.7 to about 6.0. | |

8. The method of claim 7 wherein the medium is DCR-2 medium comprising medium DCR-1 additionally containing about $5 \times 10^{-5}$M 2,4-dichlorophenoxyacetic acid, about $2 \times 10^{-5}$M kinetin and about $2 \times 10^{-5}$M $N^6$-benzyladenine.

9. The method of claim 8 wherein the medium is DCR-3 medium comprising DCR-1 medium additionally containing about $5 \times 10^{-6}$M 2,4-dichlorophenoxyacetic acid, about $2 \times 10^{-6}$M kinetin and about $2 \times 10^{-6}$M $N^6$-benzyladenine.

10. The method of claim 9 wherein the medium is DCR-4 medium comprising medium DCR-1 additionally containing about $1 \times 10^{-6}$M napthalene-2-acetic acid, and about $2 \times 10^{-5}$M kinetin and about $2 \times 10^{-5}$M $N^6$-benzyladenine.

11. The method of claim 2 wherein the plant growth regulator is selected from the group consisting of 2,4-dichlorophenoxyacetic acid, abscisic acid, $N^6$-benzyladenine, kinetin, thidiazuron, and indolebutyric acid, and the organic nitrogen source is selected from the group consisting of amino acids and casein hydrolysate, and cyclitols are selected from the group consisting of inositol and myo-inositol.

12. The method of claim 3 wherein the medium is modified MS-1 or DCR-1 medium, said modified medium selected from the group consisting of Loblobby pine LP or LPH medium, Douglas fir DMH medium and *Picea Abies* BMH medium.

13. The method of claim 12 wherein said modified medium comprises one or more stock solutions selected from

| Macro Salt - 4% Stock | |
|---|---|
| $NH_4NO_3$ | 8.812 g |
| $KNO_3$ | 74.784 g |
| $CaCl_2$ | 7.040 g |
| $MgSO_4$—$7H_2O$ | 5.920 g |
| $KH_2PO_4$ | 2.720 g |
| Water | up to 4000 ml; |
| Micro Salts - 1000% Stock | |
| $H_3BO_3$ | 0.620 g |
| $MnSO_4$—$H_2O$ | 1.690 g |
| $ZnSO_4$—$7H_2O$ | 0.860 g |
| Potassiumiodide (KI) | 0.083 g |

-continued

| | | |
|---|---|---|
| NaMoO$_4$—H$_2$O | 0.025 g | |
| CuSO$_4$—5H$_2$O | 0.0025 g | |
| CaCl$_2$—6H$_2$O | 0.0025 g | |
| Water | up to 100 ml; | |
| Nitrate - 50% Stock | | |
| NH$_4$NO$_3$ | 20.0 g | |
| Ca(NO$_3$)$_2$—4H$_2$O | 27.8 g | |
| KNO$_3$ | 17.0 g | |
| Water | up to 1000 ml; | |
| Sulfate - 50% Stock | | |
| MgSO$_4$—7H$_2$O | 18.5 g | |
| MnSO$_4$—H$_2$O | 1.115 g | |
| ZnSO$_4$—7H$_2$O | 0.43 g | |
| CaSO$_4$—5H$_2$O | 0.0125 g | |
| Water | up to 1000 ml; | |
| Halide - 50% Stock | | |
| CaCl—2H$_2$O | 5.5 g | |
| KI | 0.0415 g | |
| CaCl—6H$_2$O | 0.00125 g | |
| NiCl | 0.00125 g | |
| Water | up to 1000 ml; | |
| PBMO Stock 50% Stock | | |
| KH$_2$PO$_4$ | 8.5 g | |
| H$_3$BO$_3$ | 0.31 g | |
| Na$_2$MoO$_4$ | 0.0125 g | |
| Water | up to 1000 ml; | |
| BAP Stock-1 μmole/ml | | |
| BAP | 22.25 mg | |
| HCl 0.1N | 2 ml | |
| Water | up to 100 ml; | |
| Kinetin Stock | | |
| Kinetin | 22.54 mg | |
| KOH 0.1N | 2 ml | |
| Water | up to 100 ml; | |
| 2,4-D Stock-1 μmole/ml | | |
| 2,4-D | 22.1 mg | |
| Ethanol 70% | 2 ml | |
| Water | up to 100 ml; | |
| NAA Stock Solution | | |
| NAA | 20 mg | |
| Ethanol | 5 ml | |
| Water | up to 100 ml; | |
| FeEDTA 100% stock | | |
| FeSO$_4$—7H$_2$O | 2.780 g | |
| Na$_2$EDTA—2H$_2$O | 3.723 g | |
| Water | up to 100 ml; | |
| Vitamin Stock 1000% stock | | |
| Thiamine-HCl | 0.10 g | |
| Nicotine Acid | 0.05. g | |
| Pyridoxine-HCl | 0.05 g | |
| Glycine | 0.20 g | |
| Water | up to 1000 ml; | | and

| | | |
|---|---|---|
| LP Medium Stock (10×) | | |
| NH$_4$NO$_3$ | 16.5 g | |
| KNO$_3$ | 19.0 g | |
| MgSO$_4$—7H$_2$O | 18.5 g | |
| KH$_2$PO$_4$ | 3.4 g | |
| CaCl—2H$_2$O | 0.22 g | |
| H$_3$BO$_3$ | 0.31 g | |
| MnSO$_4$ | 0.21 g | |
| ZnSO$_4$ | 0.43 g | |
| NaMoO$_4$ | 0.0125 g | |
| CuSO$_4$—H$_2$O | 0.005 g | |
| CoCl$_2$—H$_2$O | 0.00125 g | |
| KI | 0.0415 g | |

-continued

| | | |
|---|---|---|
| FeEDTA Stock | 5.0 ml/l | |
| Vitamin Stock | 1.0 ml/l | |
| Water up to | 1000 ml. | |

14. The method of claim 13 wherein the plant is Douglas fir and the medium is modified DCR medium containing

| | | |
|---|---|---|
| Nitrate | (50% Stock) | 10 ml |
| Sulfate | (50% Stock/) | 10 ml |
| PBMO | (50% Stock) | 10 ml |
| Halide | (50% Stock) | 10 ml |
| FeEDTA | (1000% Stock) | 5 ml |
| Vitamin | (1000% Stock) | 1 ml |
| Sucrose | (3%) | 1 ml |
| Inositol | | 1000 mg |
| Casein Hydrolysate | | 500 mg |
| L-glutamine | | 450 mg |
| 2,4-D | (1 μmole/ml stock) | 5 ml |
| Kinetin | (1 μmole/ml stock) | 2 ml |
| BAP | (1 μmole/ml stock) | 2 ml |
| Water adjusted to pH 5.75. | | up to 1000 ml |

15. The method of claim 14 wherein the plant is Loblolly pine and the medium is LP medium consisting of

| | | |
|---|---|---|
| LP Medium | 10% Stock | 50 ml |
| FeEDTA | 100% Stock | 5 ml |
| Vitamin | 100% Stock | 1 ml |
| Sucrose | | 3% |
| Inositol | | 1000 mg |
| Casein acid hydrolysate | | 500 mg |
| L-glutamine | | 450 mg |
| 2,4-D | 1 μmole/ml Stock | 5 ml |
| Kinetin | 1 μmole/ml Stock | 2 ml |
| BAP | 1 μmole/ml Stock | 2 ml |
| Water adjusted to pH 5.7. | | up to 1000 ml |

16. The method of claim 13 wherein the plant is Douglas fir or Loblolly Pine and the medium is suitable for subculture of shoots, said medium comprising

| | | |
|---|---|---|
| BMO | 50% Stock | 10 ml |
| Halide | 50% Stock | 10 ml |
| Nitrate | 50% Stock | 10 ml |
| Sulfate | 50% Stock | 10 ml |
| Myo-inositol | | 0.10 g |
| FeEDTA | 100% Stock | 5.0 ml |
| Vitamin | 1000% Stock | 0.5 ml |
| Sucrose | | 2.0% |
| BAP | 0.2 mg/ml stock | 0.25 ml |
| NAA | 0.1 mg/ml stock | 0.10 ml |
| Water adjusted to pH 5.8–5.9. | | up to 1000 ml |

17. The method of claim 13 wherein the plant is *Picea Abies* and the medium is modified MS medium (BMH) consisting of

| | | |
|---|---|---|
| Macro salts | 4% Stock | 125 ml |
| FeEDTA | 100% Stock | 5 ml |
| Vitamin | 1000% Stock | 1 ml |
| Micro Salts | 1000% Stock | 0.5 ml |
| Sucrose | | 3% |
| Inositol | | 1000 mg |
| Casein hydrolysate | | 500 mg |
| L-glutamine | | 450 mg |
| 2,4-D 1 | 1 μmole/ml stock | 5 ml |

| | | |
|---|---|---|
| Linetin | 1 μmole/ml stock | 2 ml |
| BAP | 0.2 mg/ml stock | 2 ml |
| Water | | up to 1000 ml |
| adjusted to pH 5. | | |

18. The method of claim 17 wherein the medium is suitable for expression of *Picea Abies* embryos, said medium comprising modified medium of claim 17 containing 0.5% KNO$_3$, further supplemented with

| | |
|---|---|
| Arginine | 40 mg and |
| Asparagine | 100 mg. |

19. The method of claim 13 wherein the medium is nutrient medium (DMH) suitable for rescued embryonal suspensor masses of Douglas-Fir, said medium comprising

| | mg/1000 ml |
|---|---|
| Nitrates | |
| NH$_4$NO$_3$ | 220 |
| Ca(NO$_3$)$_2$.4H$_2$O | 278 |
| KNO$_3$ | 170 |
| Sulfates | |
| MgSO$_4$.7H$_2$O | 185 |
| MnSO$_4$.H$_2$O | 11.2 |
| ZnSO$_4$.7H$_2$O | 4.3 |
| CuSO$_4$.5H$_2$O | 0.013 |
| Halides | |
| CaCl.2H$_2$O | 55 |
| KI | 0.41 |
| CoCl$_2$.6H$_2$O | 0.012 |
| NiCl | 0.012 |
| Phosphate, Borate, Molybdenate | |
| KH$_2$PO$_4$ | 85 |
| H$_3$BO$_3$ | 3.1 |
| NaMnO$_4$ | 0.12 |
| Fe.EDTA | |
| FeSO$_4$.7H$_2$O | 13.96 |
| Na$_2$EDTA.2H$_2$O | 18.62 |
| Vitamins | |
| Thiamine.HCl | 1.00 |
| Nicotinic acid | 0.5 |
| Pyridoxine.HCl | 0.50 |
| Carbon and Nitrogen Sources | |
| myo-inositol | 1,000 |
| Casein hydrolysate | 500 |
| L-glutamine | 450 |
| Glycine | 2 |
| L-tryptophan | 1 |
| Sucrose | 30 g/L |
| Water | up to 1000 ml |
| adjusted to pH 5.8 before autoclaving. | |

20. The method of claim 13 wherein the plant is Norway spruce.

21. The method of claim 13 wherein the plant is *Araucaria angustifolia*.

22. The method of claim 13 wherein the plant is Sugar pine.

23. The method of claim 13 wherein the plant is Douglas fir.

24. The method of claim 13 wherein the plant is *cupressus sempervirens*.

25. The method of claim 1 wherein the diploid parthenogenesis conditions include culturing the rescued tissues of step (c) at humidity greater than 60%.

26. The method of claim 25 wherein the temperature is between about 18° C. and about 28° C.

27. The method of claim 26 wherein the embryonal suspensor mass in step (e) is developed by incubating the rescued embryo on MS-1 or DCR-1 medium supplemented with essential macronutrients, micronutrients, vitamins, plant growth regulators, carbon and nitrogen sources at about 20° C. to 26° C., in darkness for about 3–6 weeks.

28. The method of claim 27 wherein the embryonal suspensor mass of step (d), identified as a white proliferating mass of cells emerging from a zygotic proembryo is distinguished from a nonembryonic callus, and isolated.

29. The method of claim 28 wherein the presence of the egg-equivalent binucleate stage in the embryonal suspensor mass cells is determined by a double staining diagnostic method.

30. The method of claim 29 wherein the diagnostic method comprises staining the embryonal suspensor mass cells first with acetocarmine followed with staining with an Evan's blue.

31. The method of claim 30 wherein the embryonal suspensor mass cells having two or more nuclei with at least one nuclei staining red are identified, separated from cells staining blue, isolated as parthenotes, and subcultured according to step (f) into an early embryo.

32. The method of claim 31 wherein the parthenotes are transferred and subcultured on MS-2 or DCR-2 medium supplemented with one or more plant growth regulators.

33. The method of claim 32 wherein the early embryo is transferred to MS-3 or DCR-3 medium supplemented with one or more plant growth regulators.

34. The method of claim 33 wherein the plant growth regulator is selected from a group consisting of kinetin, abscisic acid, 2,4-dichlorophenoxyacetic acid, colchicine and thidiazuron.

35. The method of claim 34 wherein the plant growth regulator is abscisic acid.

36. The method of claim 34 wherein the plant growth regulator is colchicine.

37. The method of claim 34 wherein the plant growth regulator is 2,4-dichlorophenoxyacetic acid.

* * * * *